US012559449B2

(12) United States Patent
Guo et al.

(10) Patent No.: US 12,559,449 B2
(45) Date of Patent: Feb. 24, 2026

(54) AROMATIC RING OR HETEROAROMATIC RING DERIVATIVES, PREPARATION METHOD THEREFOR AND USE THEREOF

(71) Applicants: ZHEJIANG HISUN PHARMACEUTICAL CO., LTD., Zhejiang (CN); SHANGHAI ARYL PHARMTECH CO., LTD., Shanghai (CN)

(72) Inventors: Yanghui Guo, Zhejiang (CN); Weiwei Liao, Zhejiang (CN); Lichen Meng, Zhejiang (CN); Taishan Hu, Zhejiang (CN); Lei Chen, Zhejiang (CN); Guoping Jiang, Zhejiang (CN)

(73) Assignees: ZHEJIANG HISUN PHARMACEUTICAL CO., LTD., Zhejiang (CN); SHANGHAI ARYL PHARMTECH CO., LTD., Shanghai (CN)

( * ) Notice: Subject to any disclaimer, the term of this patent is extended or adjusted under 35 U.S.C. 154(b) by 1048 days.

(21) Appl. No.: 17/610,162

(22) PCT Filed: Apr. 1, 2020

(86) PCT No.: PCT/CN2020/082714
§ 371 (c)(1),
(2) Date: Nov. 10, 2021

(87) PCT Pub. No.: WO2020/228436
PCT Pub. Date: Nov. 19, 2020

(65) Prior Publication Data

US 2022/0227699 A1 Jul. 21, 2022

(30) Foreign Application Priority Data

May 10, 2019 (CN) ........................ 201910386712.4

(51) Int. Cl.

| | |
|---|---|
| ***C07C 233/55*** | (2006.01) |
| ***A61P 25/02*** | (2006.01) |
| ***C07D 223/16*** | (2006.01) |
| ***C07D 267/14*** | (2006.01) |
| ***C07D 413/04*** | (2006.01) |
| ***C07D 413/10*** | (2006.01) |
| ***C07D 413/14*** | (2006.01) |

(52) U.S. Cl.
CPC ............ *C07C 233/55* (2013.01); *A61P 25/02* (2018.01); *C07D 223/16* (2013.01); *C07D 267/14* (2013.01); *C07D 413/04* (2013.01); *C07D 413/10* (2013.01); *C07D 413/14* (2013.01)

(58) Field of Classification Search
CPC .. C07C 233/55; C07D 223/16; C07D 267/14; C07D 413/04; C07D 413/10; C07D 413/14; C07D 417/04; C07D 495/04; C07D 401/04; C07D 403/04; C07D 471/04; C07H 13/10
See application file for complete search history.

(56) References Cited

U.S. PATENT DOCUMENTS

| | | | |
|---|---|---|---|
| 2004/0180892 A1 | 9/2004 | Wu et al. | |
| 2006/0035882 A1 | 2/2006 | Koga et al. | |
| 2011/0053912 A1 | 3/2011 | Matsushima et al. | |
| 2013/0096121 A1 | 4/2013 | Wang et al. | |
| 2014/0371201 A1 | 12/2014 | Weiss et al. | |
| 2018/0221363 A1 | 8/2018 | Wang et al. | |

FOREIGN PATENT DOCUMENTS

| | | | | |
|---|---|---|---|---|
| CN | 103958508 A | 7/2014 | | |
| DE | 19624155 A1 * | 1/1998 | ........... C07C 233/54 | |
| JP | WO2010113834 A1 | 10/2012 | | |
| WO | 9323378 A1 | 11/1993 | | |
| WO | WO-2004073634 A2 * | 9/2004 | ............. A61K 31/16 | |
| WO | 2006006741 A1 | 1/2006 | | |
| WO | 2013110135 A1 | 8/2013 | | |
| WO | WO-2014113620 A2 * | 7/2014 | ............. A61P 35/00 | |
| WO | 2014201173 A1 | 12/2014 | | |
| WO | 2015003223 A1 | 1/2015 | | |
| WO | 2016113668 A1 | 7/2016 | | |

OTHER PUBLICATIONS

Tsai et al., High Perform Polym, 1989, 1:179-189 (Year: 1989).*
International Search Report for PCT/CN2020/082714 mailed Jun. 29, 2020, ISA/CN.
Tsai, Tsu Tzu et al., Rigid-rod Benzobisazole Polymers Containing Benzothiazole Pendent Groups, High Performance Polymers, Dec. 31, 1989, vol. 1, No. 3, pp. 179-189.
The 1st Office Action dated May 25, 2023 for the Chinese Patent Application No. CN202080034694.4. English Translation of the 1st Office Action Provided by http://globaldossier.uspto.gov.

* cited by examiner

*Primary Examiner* — Andrew D Kosar
*Assistant Examiner* — Jonathan D Mahlum
(74) *Attorney, Agent, or Firm* — Yue (Robert) Xu; Apex Attorneys at Law, LLP

(57) ABSTRACT

The present invention relates to aromatic ring or heteroaromatic ring derivatives, a preparation method therefor and applications thereof in medicine. Specifically, the present invention relates to aromatic ring or heteroaromatic ring derivatives represented by general formula (I), a preparation method therefor and pharmaceutically acceptable salts thereof, as well as a use thereof as therapeutic agents, especially uses as angiotensin II type 2 receptor ($AT_2R$) antagonists, wherein the definition of each substituent in the general formula (I) is the same as the definition thereof in the description.

13 Claims, No Drawings

AROMATIC RING OR HETEROAROMATIC RING DERIVATIVES, PREPARATION METHOD THEREFOR AND USE THEREOF

The present application is the national phase of International Application No. PCT/CN2020/082714, titled "AROMATIC RING OR HETEROAROMATIC RING DERIVATIVES, PREPARATION METHOD THEREFOR AND USE THEREOF", which claims the priority to Chinese Patent Application No. 201910386712.4, titled "AROMATIC RING OR HETEROAROMATIC RING DERIVATIVES, PREPARATION METHOD THEREFOR AND USE THEREOF", filed on May 10, 2019 with the China National Intellectual Property Administration, the entire disclosures thereof are incorporated herein by reference.

FIELD

The present disclosure relates to new aromatic ring or heteroaromatic ring derivatives, a preparation method therefor, a pharmaceutical composition containing the derivative and use thereof as therapeutic agents, especially as angiotensin II type 2 receptor ($AT_2R$) antagonists.

BACKGROUND

Neuropathic pain is a chronic pain disease caused by primary injury or dysfunction of the nervous system. According to the location of the disease, it may be divided into peripheral neuropathic pain and central neuropathic pain. Trauma, inflammation, infection or compression all may cause neuropathic pain, such as diabetic neuralgia (DNP), postherpetic neuralgia (PHN), primary neuropathy, secondary neuropathy, peripheral neuropathy, and neurological diseases caused by mechanical nerve damage or biochemical nerve damage. At present, the drugs used in clinical treatment of neuropathic pain mainly include antiepileptic drugs, antidepressants and narcotic analgesics, such as gabapentin, pregabalin, tricyclic antidepressants and so on. However, these drugs are untargeted with very limited therapeutic effects but serious side effects, including cognitive changes, sedative effects, nausea, tolerance and dependence, which are far from meeting the needs of clinical medication. Therefore, it is necessary to study the pathogenesis of neuropathic pain, find a clear target of drug action, and develop new drugs that can effectively treat neuropathic pain with few adverse reactions.

Angiotensin II receptor is a G protein-coupled receptor with angiotensin II as a ligand, and it is an important part of the renin-angiotensin system. The main subtypes of angiotensin II receptors include type 1 receptor ($AT_1R$) and type 2 receptor ($AT_2R$). $AT_1R$ and $AT_2R$ share only about 30% of the same amino acid sequence, but angiotensin II, as their main ligand, has similar affinities to the both.

$AT_1R$ is the most clearly studied angiotensin receptor. Activation of $AT_1R$ receptor may cause smooth muscle contraction, aldosterone and vasopressin secretion, increased renal tubular reabsorption of sodium, central and peripheral sympathetic nerve activation, and myocardial hypertrophy. Therefore, antagonizing angiotensin II at the receptor level has become a research hotspot for a new type of antihypertensive drugs, and a series of sartan antihypertensive drugs were born from this.

$AT_2R$ is abundantly expressed in various embryonic tissues, and less distributed in adult normal tissues, but after tissue injury, its expression increases. $AT_2R$ is related to blood pressure regulation, nerve growth, pain control and myocardial regeneration. Drugs targeting $AT_2R$ can improve cardiovascular function and relieve neuropathic pain. The compound olodanrigan (EMA401) developed by Spinifex in Australia is a highly selective $AT_2R$ antagonist and is currently in clinical phase II. This candidate drug has good therapeutic effect on neuropathic pain such as diabetic neuralgia and postherpetic neuralgia. At the same time, Spinifex is also developing the $AT_2R$ antagonist EMA-400. Both olodanrigan and EMA-400 can be prepared by the method disclosed in WO 93/23378 and their structure are as follows:

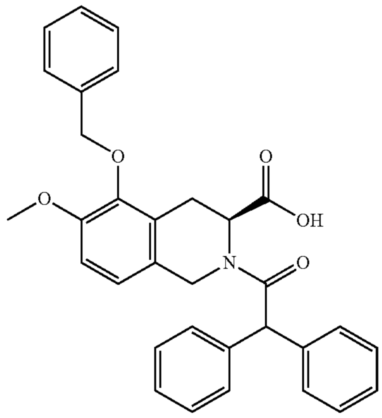

olodanrigan

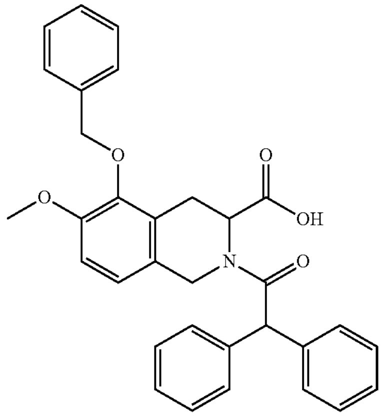

EMA-400

At present, a series of patent applications about $AT_2R$ antagonist have been published, including WO 2016113668, WO 2015003223 and WO 2013110135. Although the research and application of $AT_2R$ antagonists have made certain progress, there is still huge room for improvement, and there is still a need for new $AT_2R$ antagonist compounds with better effects. Thus, it is still necessary to continue research and development of new $AT_2R$ antagonists.

SUMMARY

The objective of the present disclosure is to provide a new $AT_2R$ antagonist with better effects, which is realized by providing a new class of aromatic ring or heteroaromatic ring derivatives as shown in general formula (I):

(I)

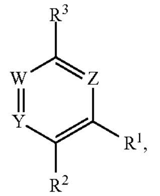

including a stereoisomer, a tautomer or a pharmaceutically acceptable salt thereof, wherein W, Y and Z are each independently selected from $CR^n$ and N, and there are at most 2 N atoms contained among W, Y, and Z;

$R^1$ is selected from —$COOR^a$ and tetrazolyl;

$R^2$ is selected from 8- to 10-membered heteroaryl and —$NR^bR^c$, wherein the heteroaryl is optionally further substituted with one or more substituents selected from $R^d$.

$R^3$ is selected from —$NR^eR^f$ and the group

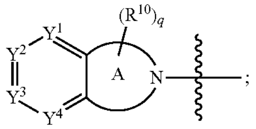

$Y^1$, $Y^2$, $Y^3$ and $Y^4$ are each independently selected from $CR^j$ and N, and there is at most 3 N atoms contained among $Y^1$, $Y^2$, $Y^3$ and $Y^4$;

ring A is selected from 6- to 8-membered monocyclic heterocyclyl and 5-membered heteroaryl, wherein the monocyclic heterocyclyl contains one or more N, O or $S(O)_n$ therein, and the 6- to 8-membered heterocycle is optionally further substituted by one or more $R^{10}$;

$R^a$ is selected from hydrogen atom and alkyl, wherein the alkyl is optionally further substituted with one or more halogens;

$R^b$ is the group:

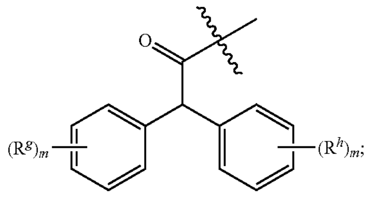

$R^c$ is alkyl, preferably methyl;

$R^e$ is selected from hydrogen atom and alkyl, wherein the alkyl is optionally further substituted with one or more substituents selected from hydroxyl, alkoxy, and halogen;

$R^f$ is selected from -L-$R^k$;

L is selected from $C_{1-6}$ alkylene, and preferably is propylidene;

$R^g$ and $R^h$ are each independently selected from hydrogen atom, alkyl, alkoxy, halogen and cyano, wherein the alkyl or alkoxy is optionally further substituted with one or more halogen or alkoxy;

$R^k$ is selected from aryl and heteroaryl, wherein the aryl or heteroaryl is optionally further substituted with one or more $R^m$;

$R^d$, $R^j$, $R^m$, $R^n$ and $R^{10}$ are the same or different, and are each independently selected from hydrogen atom, hydroxyl, halogen, nitro, cyano, alkyl, alkoxy, cycloalkyl, heterocyclyl, aryl, heteroaryl, —$C(O)R^4$, —$C(O)OR^4$, —$OC(O)R^4$, —$NR^5R^6$, —$C(O)NR^5R^6$, —$S(O)_nNR^5R^6$ and —$NR^5C(O)R^6$, wherein the alkyl, alkoxy, cycloalkyl, heterocyclyl, aryl or heteroaryl is optionally further substituted with one or more substituent selected from hydroxyl, halogen, nitro, cyano, alkoxy, cycloalkyl, heterocyclyl, aryl, heteroaryl, =O, —$C(O)R^4$, —$C(O)OR^4$, —$OC(O)R^4$, —$NR^5R^6$, —$C(O)NR^5R^6$, —$SO_2NR^5R^6$ or —$NR^5C(O)R^6$;

$R^4$, $R^5$ and $R^6$ are each independently selected from hydrogen atom, hydroxyl, halogen, nitro, cyano, alkyl, alkoxy, cycloalkyl, heterocyclyl, aryl and heteroaryl, wherein the alkyl, alkoxy, cycloalkyl, heterocyclyl, aryl or heteroaryl is optionally further substituted with one or more substituents selected from hydroxyl, halogen, nitro, cyano, alkyl, alkoxy, cycloalkyl, heterocyclyl, aryl, heteroaryl, —$C(O)R^7$, —$C(O)OR^7$, —$OC(O)R^7$, —$NR^8R^9$, —$C(O)NR^8R^9$, —$SO_2NR^8R^9$ and —$NR^8C(O)R^9$;

or, $R^5$ and $R^6$, together with the N atom connected thereto, form a 4- to 8-membered heterocyclyl, wherein the 4- to 8-membered heterocycle contains one or more N, O or $S(O)_n$, and 4- to 8-membered heterocycle is optionally further substituted with one or more substituents selected from hydroxyl, halogen, nitro, cyano, alkyl, alkoxy, cycloalkyl, heterocyclyl, aryl, heteroaryl, =O, —$C(O)R^7$, —$C(O)OR^7$, —$OC(O)R^7$, —$NR^8R^9$, —$C(O)NR^8R^9$, —$SO_2NR^8R^9$ and —$NR^8C(O)R^9$;

$R^7$, $R^8$ and $R^9$ are each independently selected from hydrogen, alkyl, cycloalkyl, heterocyclyl, aryl and heteroaryl, wherein the alkyl, cycloalkyl, heterocyclyl, aryl or heteroaryl is optionally further substituted with one or more substituents selected from hydroxyl, halogen, nitro, cyano, alkyl, alkoxy, cycloalkyl, heterocyclyl, aryl, heteroaryl, carboxyl and carboxylic ester groups;

m is selected from 0, 1, 2, 3, 4 and 5;

n is selected from 0, 1 and 2; and q is 0, 1, 2, 3, 4 or 5.

In the definition of the above-mentioned compound of general formula (I), preferably the heteroaryl in the definition of $R^2$ is selected from the groups as shown below:

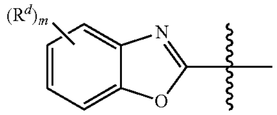
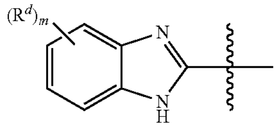
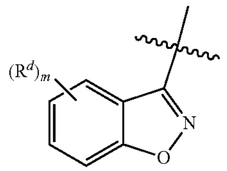
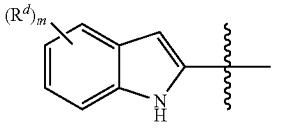
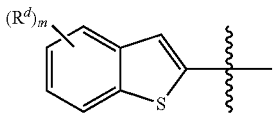
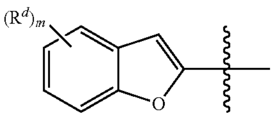

-continued

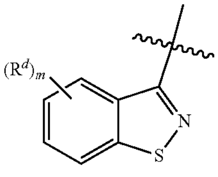
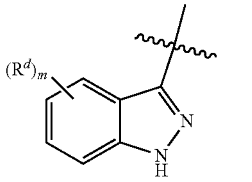
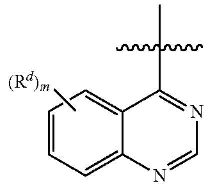
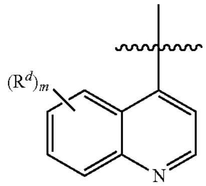
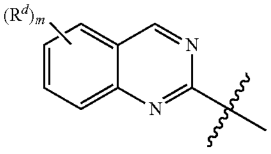
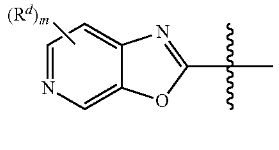
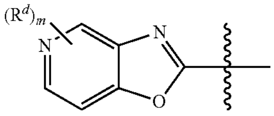
or
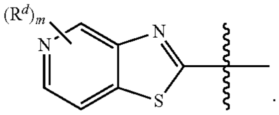
.

In the definition of the above-mentioned compound of general formula (I), preferably for the definition of $R^3$, when $R^3$ is selected from —$NR^eR^f$, $R^2$ is selected from —$NR^bR^c$.

In the definition of the above-mentioned compound of general formula (I), the ring A in the definition of $R^3$ may be selected from 6- to 8-membered monocyclic heterocyclyl and 5-membered heteroaryl, wherein the monocyclic heterocyclyl contains one or more N, O or $S(O)_n$ therein, and the 6- to 8-membered heterocycle is optionally further substituted by one or more $R^{10}$.

In the definition of the above-mentioned compound of general formula (I), the ring A in the definition of $R^3$ preferably is selected from 7- to 8-membered monocyclic heterocyclyl, wherein the monocyclic heterocyclyl contains one or more N, O or $S(O)_n$ therein, and the 7- to 8-membered heterocycle is optionally further substituted with one or more $R^{10}$.

The definitions of the above-mentioned variables (including their preferred embodiments) may be combined with any other variable definitions (including the definitions of their preferred embodiments).

In the definition of the above-mentioned compound of general formula (I), preferably, $R^1$ is selected from —$COOR^a$, $R^2$ is selected from 8- to 10-membered heteroaryl, $R^3$ is selected from the group

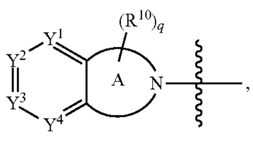
, wherein $R^a$, $Y^1$, $Y^2$, $Y^3$, $Y^4$, ring A, $R^{10}$ and q are defined as above.

In the definition of the above-mentioned compound of general formula (I), preferably, $R^1$ is selected from —$COOR^a$, $R^2$ is selected from —$NR^bR^c$; $R^3$ is selected from the group

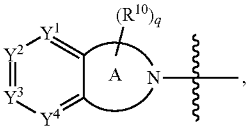
, wherein $R^a$, $R^b$, $R^c$, $Y^1$, $Y^2$, $Y^3$, $Y^4$, ring A, $R^{10}$ and q are defined as above.

In the preferred embodiments of the present disclosure, there is provided a compound represented by general formula (I) or a stereoisomer, a tautomer or a pharmaceutically acceptable salt thereof, which is a compound represented by general formula (II) or a stereoisomer, a tautomer or a pharmaceutically acceptable salt thereof, (II)

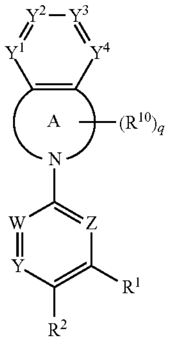

wherein W, Y and Z are each independently selected from CH and N, and there is at most 1 N atom contained among W, Y, and Z;

$Y^1$, $Y^2$, $Y^3$ and $Y^4$ are each independently selected from $CR^j$ and N, and there is at most 1 N contained among $Y^1$, $Y^2$, $Y^3$ and $Y^4$;

ring A is selected from 6- to 8-membered monocyclic heterocyclyl and 5-membered heteroaryl, wherein the monocyclic heterocyclyl contains one or more N, O or $S(O)_n$ therein, and the 6- to 8-membered heterocycle is optionally further substituted by one or more $R^{10}$;

$R^{10}$ are the same or different, and are each independently selected from halogen, alkyl, alkoxy, and =O, wherein the alkyl or alkoxy is optionally further substituted with halogen, wherein the halogen is preferably fluorine;

$R^j$ are the same or different, and are each independently selected from hydrogen atom, alkyl, alkoxy and halogen, wherein the alkyl or alkoxy is optionally further substituted with halogen, wherein the halogen is preferably fluorine, wherein the alkoxy is preferably methoxy;

q is 0, 1, 2 or 3;

$R^1$, $R^2$ and n are defined as described in general formula (I).

In the definition of the above-mentioned compound of general formula (II), the ring A in the definition of $R^3$ is selected from 6- to 8-membered monocyclic heterocyclyl and 5-membered heteroaryl, wherein the monocyclic heterocyclyl contains one or more N, O or $S(O)_n$ therein, and the 6- to 8-membered heterocycle is optionally further substituted by one or more $R^{10}$.

In the definition of the above-mentioned compound of general formula (II), the ring A in the definition of $R^3$ is preferably selected from 7- to 8-membered monocyclic heterocyclyl, wherein the monocyclic heterocyclyl contains one or more N, O or $S(O)_n$ therein, and the 7- to 8-membered heterocycle is optionally further substituted with one or more $R^{10}$.

In the definition of the above-mentioned compound of general formula (II), the alkoxy in the definition of $R^j$ is preferably methoxy.

In the preferred embodiments of the present disclosure, there is provided a compound represented by general formula (I) or a stereoisomer, a tautomer or a pharmaceutically acceptable salt thereof, which is a compound represented by general formula (III) or a stereoisomer, a tautomer or a pharmaceutically acceptable salt thereof,

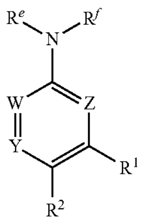

(III)

wherein W, Y and Z are each independently selected from CH and N, and there is at most 1 N atom contained among W, Y, and Z;

$R^e$ is selected from hydrogen atom and alkyl, and preferably methyl;

$R^f$ is selected from -L-$R^k$;

L is selected from $C_{1-6}$ alkylene, and preferably propylidene;

$R^k$ is selected from aryl, wherein the aryl is preferably phenyl; wherein the aryl is optionally further substituted with one or more substituents selected from halogen, alkyl and alkoxy, wherein the alkyl or alkoxy is optionally further substituted with one or more halogen;

$R^1$ and $R^2$ are defined as described in general formula (I).

In the preferred embodiments of the present disclosure, there is provided a compound as represented by general formula (I), (II) or (III), or a stereoisomer, a tautomer or a pharmaceutically acceptable salt thereof, wherein $R^2$ is selected from the groups:

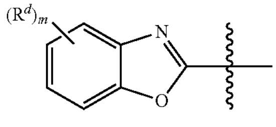

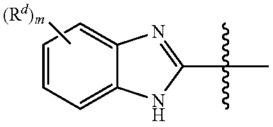

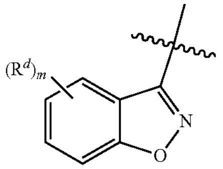

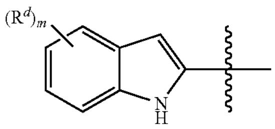

-continued

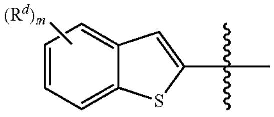

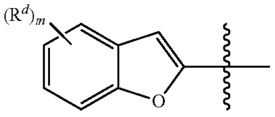

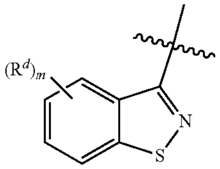

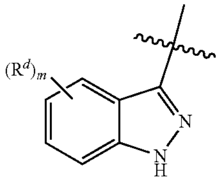

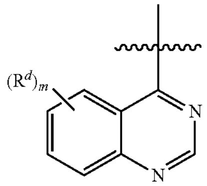

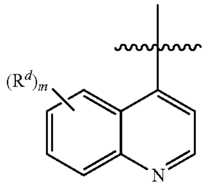

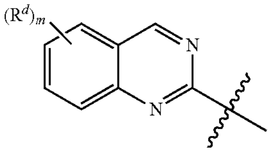

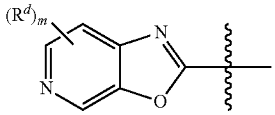

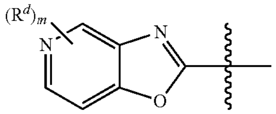

or

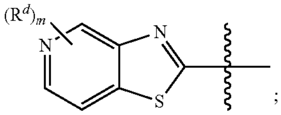

;

$R^d$ are the same or different, and are each independently selected from hydrogen atom, alkyl, cyano, alkoxy and halogen, wherein the alkyl or alkoxy is optionally further substituted with halogen; wherein the halogen is preferably fluorine or chlorine;

m is 0, 1, 2, 3 or 4.

For the above-mentioned compound as represented by general formula (I), (II) or (III), or the stereoisomer, the tautomer or the pharmaceutically acceptable salt thereof of the present disclosure, preferably, $R^d$ in the definition are the same or different, and are each independently selected from hydrogen atom, alkyl, cyano, alkoxy or halogen, wherein the alkyl or alkoxy is optionally further substituted with halogen, wherein the halogen is preferably fluorine or chlorine.

In the preferred embodiments of the present disclosure, there is provided a compound as represented by general formula (I), (II) or (III) or a stereoisomer, a tautomer or a pharmaceutically acceptable salt thereof, wherein $R^2$ is selected from the group:

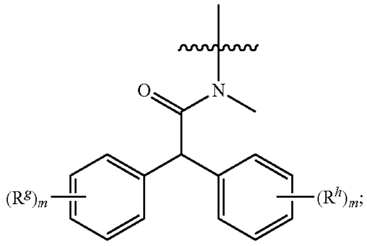

wherein $R^g$, $R^h$ and m are defined as described in general formula (I).

In the preferred embodiments of the present disclosure, there is provided a compound as represented by general formula (I), (II) or (III), or a stereoisomer, a tautomer or a pharmaceutically acceptable salt thereof, wherein $R^2$ is selected from the groups:

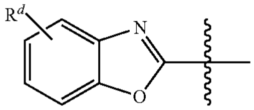
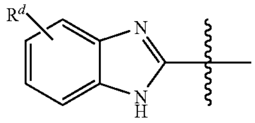
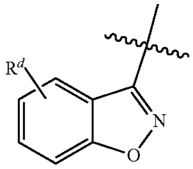
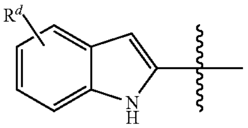
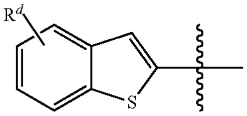
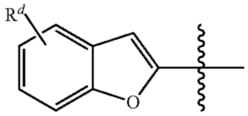
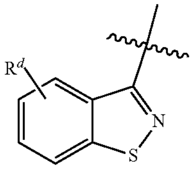
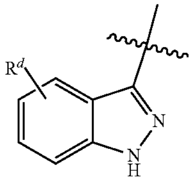
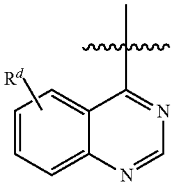
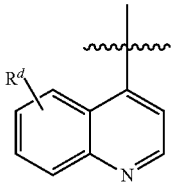
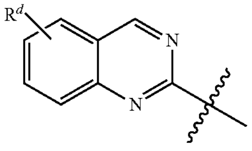
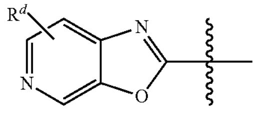
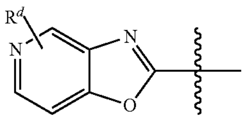
or
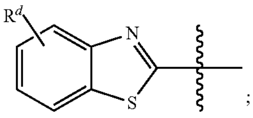
;

$R^d$ is selected from hydrogen atom, fluorine, chlorine, cyano, methyl, ethyl, isopropyl, difluoromethyl, trifluoromethyl and trifluoromethoxy.

In the preferred embodiments of the present disclosure, there is provided a compound as represented by general formula (I), (II) or (III), or a stereoisomer, a tautomer or a pharmaceutically acceptable salt thereof, wherein $R^2$ is selected from the group:

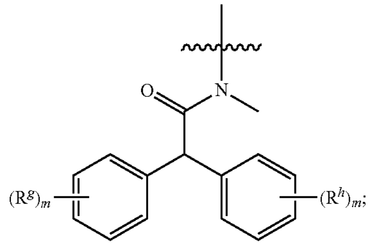

$R^g$ and $R^h$ are each independently selected from hydrogen atom, fluorine, chlorine, cyano, methyl, ethyl, isopropyl, difluoromethyl, trifluoromethyl and trifluoromethoxy; and preferably, $R^g$ and $R^h$ are each independently a hydrogen atom or fluorine; and m is 1.

In the preferred embodiments of the present disclosure, there is provided a compound as represented by general formula (II), or a stereoisomer, a tautomer or a pharmaceutically acceptable salt thereof, wherein

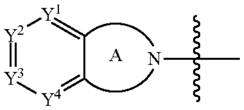

is selected from the groups:

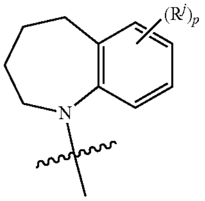
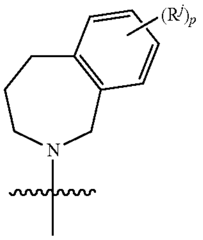
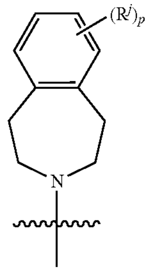
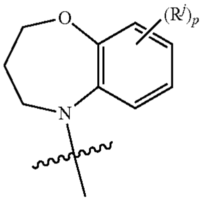
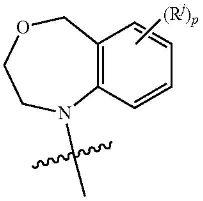
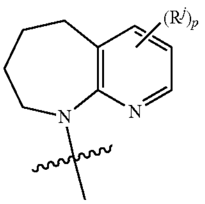
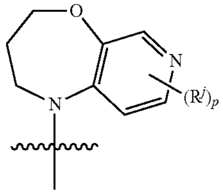
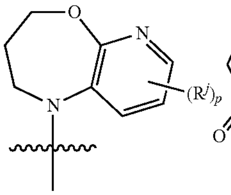
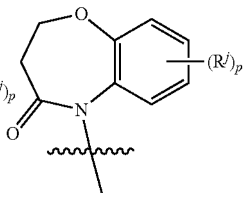

-continued

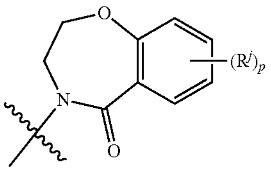

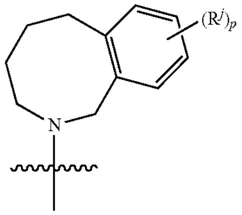

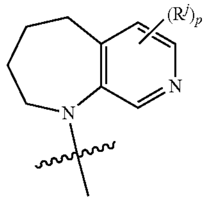

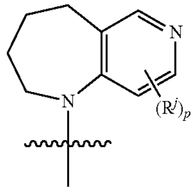

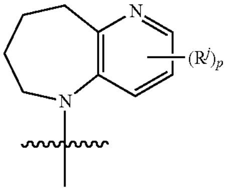

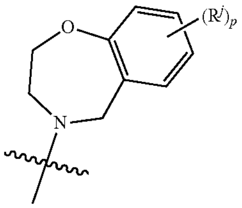

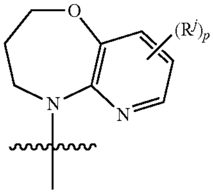

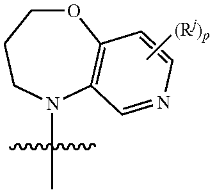

-continued

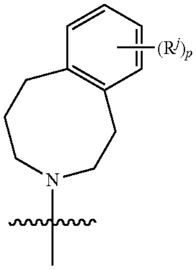

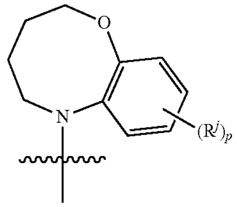

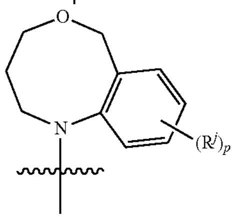

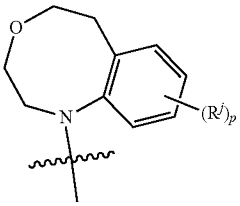

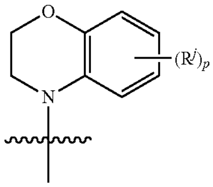

or

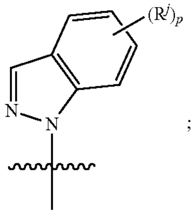

;

$R^j$ are the same or different, and are each independently selected from hydrogen atom, alkyl, alkoxy and halogen, wherein the alkyl or alkoxy is optionally further substituted with halogen, wherein the halogen is preferably fluorine, wherein the alkoxy is preferably methoxy; and p is 0, 1, 2, 3 or 4.

Typical compounds of the present disclosure include, but are not limited to:

| compound number | structure | name |
|---|---|---|
| 1 | 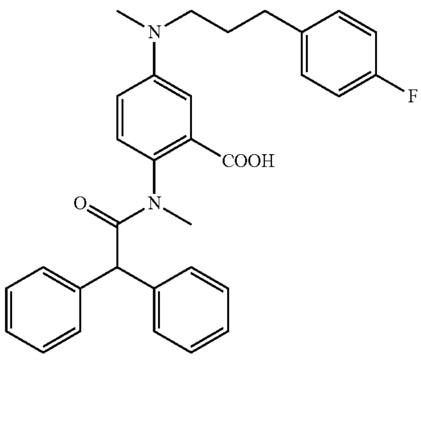 [SMILES: CN(CCCc1ccc(F)cc1)c1ccc(N(C)C(=O)C(c2ccccc2)c2ccccc2)c(C(=O)O)c1] | 5-((3-(4-fluorophenyl)propyl)(methyl)amino)-2-(N-methyl-2,2-diphenylacetamido)benzoic acid |

-continued
| compound number | structure | name |
|---|---|---|
| 2 | 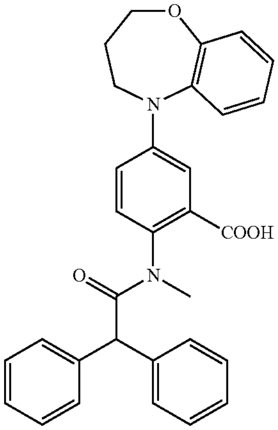 [SMILES: CN(C(=O)C(c1ccccc1)c1ccccc1)c1ccc(N2CCCOc3ccccc32)cc1C(=O)O] | 5-(3,4-dihydrobenzo[b][1,4]oxazepine-5(2H)-yl)-2-(N-methyl-2,2-diphenylacetamido)benzoic acid |
| 3 | 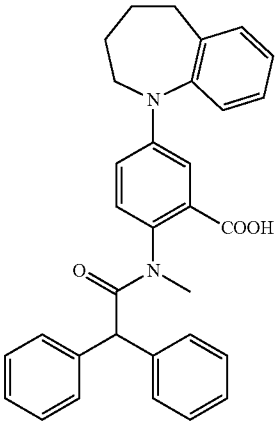 [SMILES: CN(C(=O)C(c1ccccc1)c1ccccc1)c1ccc(N2CCCCc3ccccc32)cc1C(=O)O] | 2-(N-methyl-2,2-diphenylacetamido)-5-(2,3,4,5-tetra-hydro-1H-benzo[b]azepin-1-yl)benzoic acid |
| 4 | 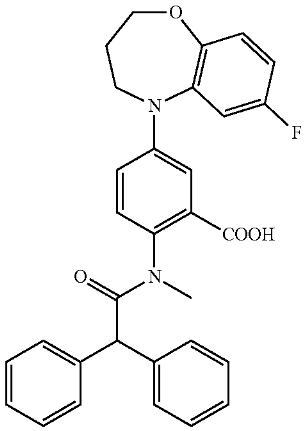 | 5-(7-fluoro-3,4-dihydrobenzo[b][1,4]oxazepine-5(2H)-yl)-2-(N-methyl-2,2-diphenylacetamido)benzoic acid |

-continued
| compound number | structure | name |
|---|---|---|
| 5 | 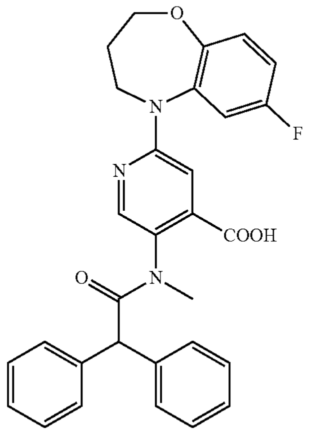 [SMILES: CN(C(=O)C(c1ccccc1)c1ccccc1)c1cnc(N2CCCOc3ccc(F)cc32)cc1C(=O)O] | 2-(7-fluoro-3,4-dihydrobenzo[b][1,4]oxazepine-5(2H)-yl)-5-(N-methyl-2,2-diphenylacetamido)isonicotinic acid |
| 6 | 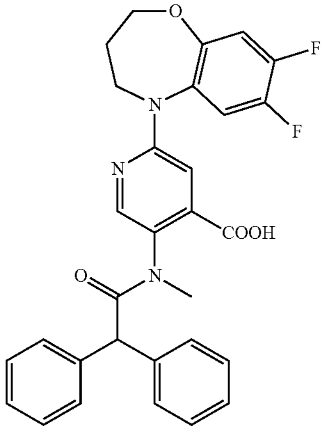 [SMILES: CN(C(=O)C(c1ccccc1)c1ccccc1)c1cnc(N2CCCOc3cc(F)c(F)cc32)cc1C(=O)O] | 2-(7,8-difluoro-3,4-dihydrobenzo[b][1,4]oxazepine-5(2H)-yl)-5-(N-methyl-2,2-diphenylacetamido) isonicotinic acid |
| 7 | 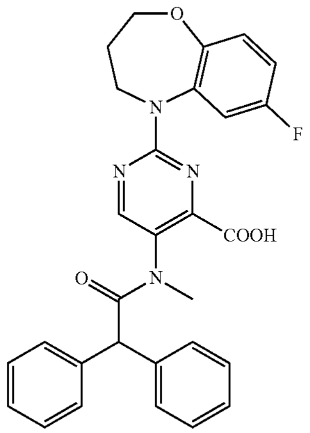 [SMILES: CN(C(=O)C(c1ccccc1)c1ccccc1)c1cnc(N2CCCOc3ccc(F)cc32)nc1C(=O)O] | 2-(7-fluoro-3,4-dihydrobenzo[b][1,4]oxazepine-5(2H)-yl)-5-(N-methyl-2,2-diphenylacetamido)pyrimidyl-4-carboxylic acid |

-continued
| compound number | structure | name |
|---|---|---|
| 8 | 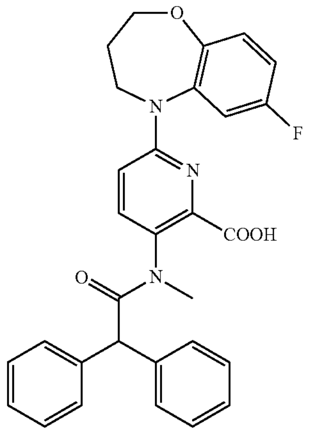 [SMILES: CN(C(=O)C(c1ccccc1)c1ccccc1)c1ccc(N2CCCOc3ccc(F)cc32)nc1C(=O)O] | 6-(7-fluoro-3,4-dihydrobenzo[b][1,4]oxazepine-5(2H)-yl)-3-(N-methyl-2,2-diphenylacetamido)picolinic acid |
| 9 | 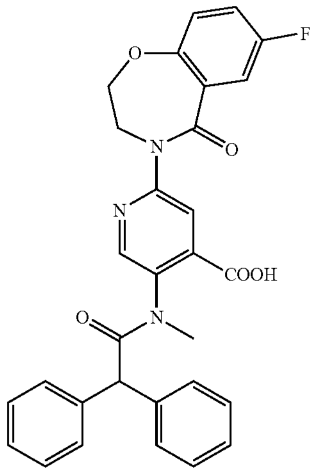 [SMILES: CN(C(=O)C(c1ccccc1)c1ccccc1)c1cnc(N2CCOc3ccc(F)cc3C2=O)cc1C(=O)O] | 2-(7-fluoro-5-oxo-2,3-dihydrobenzo[f][1,4]oxazepine-4(5H)-yl)-5-(N-methyl-2,2-diphenyl-acetamido)isonicotinic acid |
| 10 | 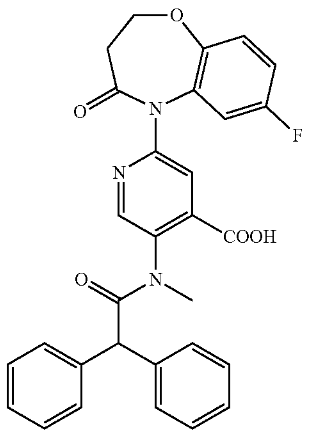 [SMILES: CN(C(=O)C(c1ccccc1)c1ccccc1)c1cnc(N2C(=O)CCOc3ccc(F)cc32)cc1C(=O)O] | 2-(7-fluoro-4-oxo-3,4-dihydrobenzo[b][1,4]oxazepine-5(2H)-yl)-5-(N-methyl-2,2-diphenyl-acetamido)isonicotinic acid |

-continued
| compound number | structure | name |
|---|---|---|
| 11 | 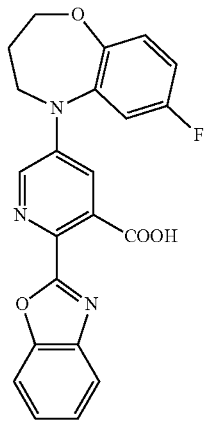 | 2-(benzo[d]oxazol-2-yl)-5-(7-fluoro-3,4-dihydrobenzo [b][1,4]oxazepine-5(2H)-yl)nicotinic acid |
| 12 | 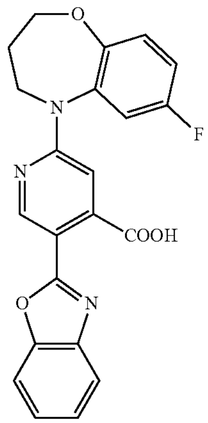 [SMILES: O=C(O)c1cc(N2CCCOc3ccc(F)cc32)ncc1-c1nc2ccccc2o1] | 5-(benzo[d]oxazol-2-yl)-2-(7-fluoro-3,4-dihydrobenzo [b][1,4]oxazepine-5(2H)-yl)isonicotinic acid |
| 13 | 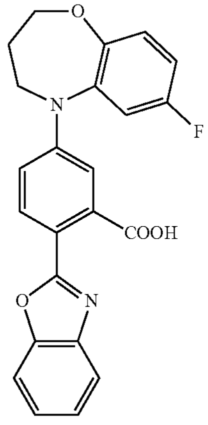 [SMILES: O=C(O)c1cc(N2CCCOc3ccc(F)cc32)ccc1-c1nc2ccccc2o1] | 2-(benzo[d]oxazol-2-yl)-5-(7-fluoro-3,4-dihydrobenzo [b][1,4]oxazepine-5(2H)-yl)benzoic acid |

-continued
| compound number | structure | name |
| --- | --- | --- |
| 14 | 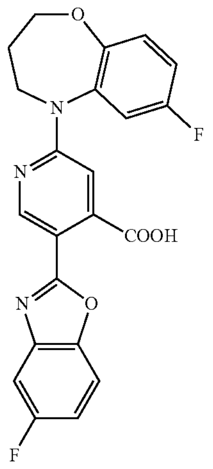 [SMILES: O=C(O)c1cc(N2CCCOc3ccc(F)cc32)ncc1-c1nc2cc(F)ccc2o1] | 2-(7-fluoro-3,4-dihydrobenzo[b][1,4]oxazepine-5(2H)-yl)-5-(5-fluorobenzo[d]oxazol-2-yl)isonicotinic acid |
| 15 | 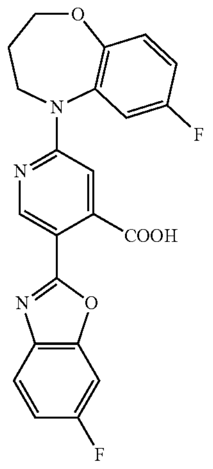 | 2-(7-fluoro-3,4-dihydrobenzo[b][1,4]oxazepine-5(2H)-yl)-5-(6-fluorobenzo[d]oxazol-2-yl)isonicotinic acid |
| 16 | 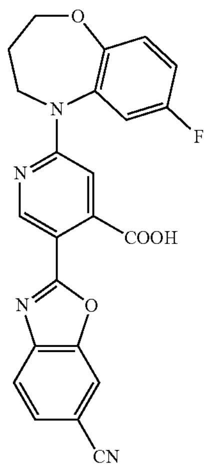 | 5-(6-cyanobenzo[d]oxazol-2-yl)-2-(7-fluoro-3,4-dihydro-benzo[b][1,4]oxazepine-5(2H)-yl)isonicotinic acid |

-continued
| compound number | structure | name |
| --- | --- | --- |
| 17 | 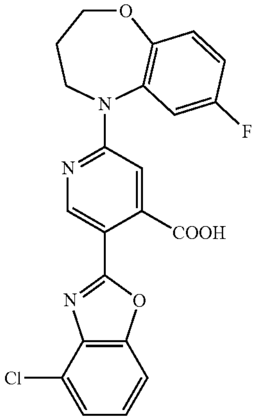 [SMILES: O=C(O)c1cc(N2CCCOc3ccc(F)cc32)ncc1-c1nc2c(Cl)cccc2o1] | 5-(4-chlorobenzo[d]oxazol-2-yl)-2-(7-fluoro-3,4-dihydro-benzo[b][1,4]oxazepine-5(2H)-yl)isonicotinic acid |
| 18 | 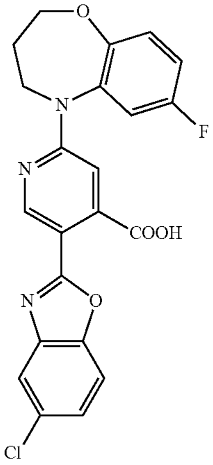 [SMILES: O=C(O)c1cc(N2CCCOc3ccc(F)cc32)ncc1-c1nc2cc(Cl)ccc2o1] | 5-(5-chlorobenzo[d]oxazol-2-yl)-2-(7-fluoro-3,4-dihydro-benzo[b][1,4]oxazepine-5(2H)-yl)isonicotinic acid |
| 19 | 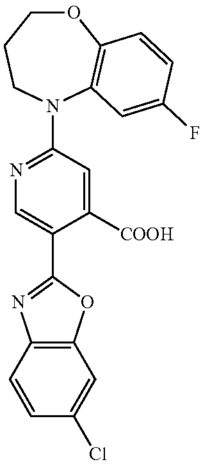 [SMILES: O=C(O)c1cc(N2CCCOc3ccc(F)cc32)ncc1-c1nc2ccc(Cl)cc2o1] | 5-(6-chlorobenzo[d]oxazol-2-yl)-2-(7-fluoro-3,4-dihydro-benzo[b][1,4]oxazepine-5(2H)-yl)isonicotinic acid |

-continued
| compound number | structure | name |
|---|---|---|
| 20 | 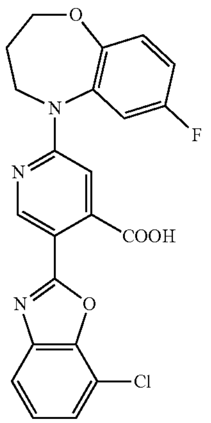 [SMILES: O=C(O)c1cc(N2CCCOc3ccc(F)cc32)ncc1-c1nc2cccc(Cl)c2o1] | 5-(7-chlorobenzo[d]oxazol-2-yl)-2-(7-fluoro-3,4-dihydro-benzo[b][1,4]oxazepine-5(2H)-yl)isonicotinic acid |
| 21 | 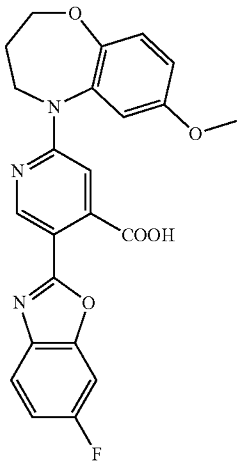 [SMILES: COc1ccc2c(c1)N(c1cc(C(=O)O)c(-c3nc4ccc(F)cc4o3)cn1)CCCO2] | 5-(6-fluorobenzo[d]oxazol-2-yl)-2-(7-methoxy-3,4-dihydro-benzo[b][1,4]oxazepine-5(2H)-yl)isonicotinic acid |
| 22 | 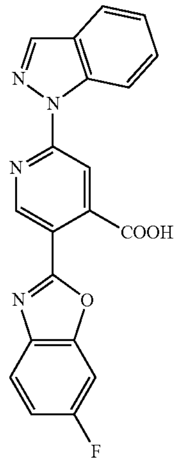 | 5-(6-fluorobenzo[d]oxazol-2-yl)-2-(1H-indazol-1-yl) isonicotinic acid |

-continued
| compound number | structure | name |
|---|---|---|
| 23 | 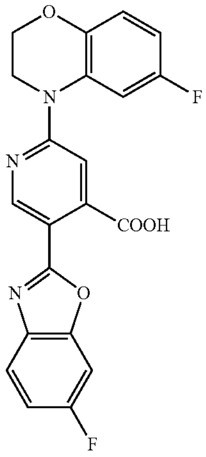 [SMILES: O=C(O)c1cc(N2CCOc3ccc(F)cc32)ncc1-c1nc2ccc(F)cc2o1] | 2-(6-fluoro-2,3-dihydro-4H-benzo[b][1,4]oxazin-4-yl)-5-(6-fluorobenzo[d]oxazol-2-yl)isonicotinic acid |
| 24 | 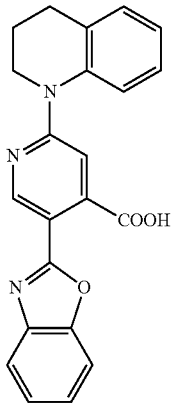 | 5-(benzo[d]oxazol-2-yl)-2-(3,4-dihydroquinoline-1(2H)-yl)isonicotinic acid |
| 1f | 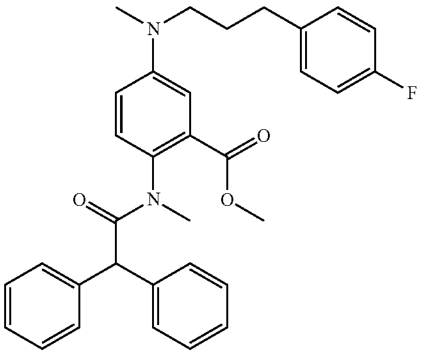 [SMILES: COC(=O)c1cc(N(C)CCCc2ccc(F)cc2)ccc1N(C)C(=O)C(c1ccccc1)c1ccccc1] | methyl 5-((3-(4-fluorophenyl)propyl)(methyl)amino)-2-(N-methyl-2,2-diphenylacetamido)benzoate |

-continued
| compound number | structure | name |
|---|---|---|
| 2b | 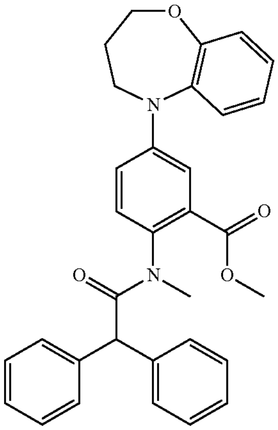 [SMILES: COC(=O)c1cc(N2CCCOc3ccccc32)ccc1N(C)C(=O)C(c1ccccc1)c1ccccc1] | methyl 5-(3,4-dihydrobenzo[b][1,4]oxazepine-5(2H)-yl)-2-(N-methyl-2,2-diphenylacetamido) benzoate |
| 3b | 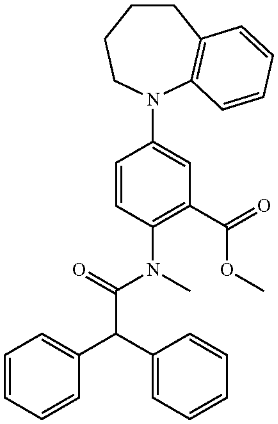 [SMILES: COC(=O)c1cc(N2CCCCc3ccccc32)ccc1N(C)C(=O)C(c1ccccc1)c1ccccc1] | methyl 2-(N-methyl-2,2-diphenylacetamido)-5-(2,3,4,5-tetrahydro-1H-benzo[b]azepin-1-yl)benzoate |
| 4b | 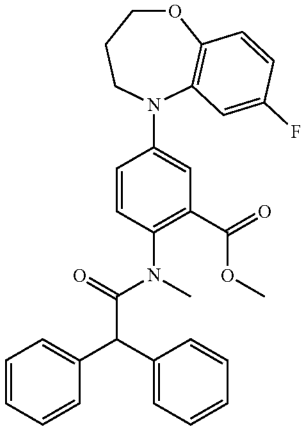 [SMILES: COC(=O)c1cc(N2CCCOc3ccc(F)cc32)ccc1N(C)C(=O)C(c1ccccc1)c1ccccc1] | methyl 5-(7-fluoro-3,4-dihydrobenzo[b][1,4]oxazepine-5(2H)-yl)-2-(N-methyl-2,2-diphenylacetamido) benzoate |

-continued
| compound number | structure | name |
|---|---|---|
| 5d | 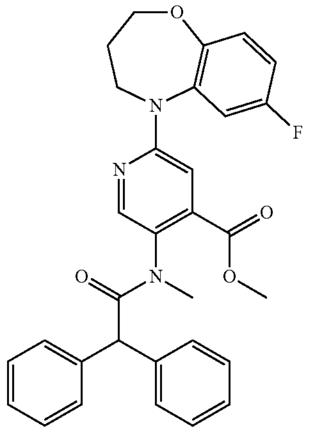 [SMILES: COC(=O)c1cc(N2CCCOc3ccc(F)cc32)ncc1N(C)C(=O)C(c1ccccc1)c1ccccc1] | methyl 2-(7-fluoro-3,4-dihydrobenzo[b][1,4]oxazepine-5(2H)-yl)-5-(N-methyl-2,2-diphenylacetamido)isonicotinate |
| 6b | 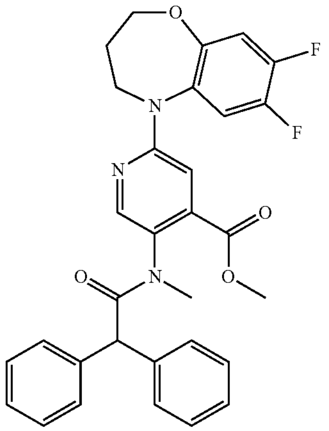 [SMILES: COC(=O)c1cc(N2CCCOc3cc(F)c(F)cc32)ncc1N(C)C(=O)C(c1ccccc1)c1ccccc1] | methyl 2-(7,8-difluoro-3,4-dihydrobenzo[b][1,4]oxazepine-5(2H)-yl)-5-(N-methyl-2,2-diphenylacetamido) isonicotinate |
| 7e | 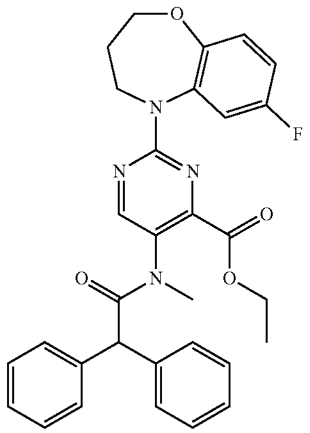 [SMILES: CCOC(=O)c1nc(N2CCCOc3ccc(F)cc32)ncc1N(C)C(=O)C(c1ccccc1)c1ccccc1] | ethyl 2-(7-fluoro-3,4-dihydrobenzo[b][1,4]oxazepine-5(2H)-yl)-5-(N-methyl-2,2-diphenylacetamido)pyrimidine-4-carboxylate |

-continued
| compound number | structure | name |
|---|---|---|
| 8d | 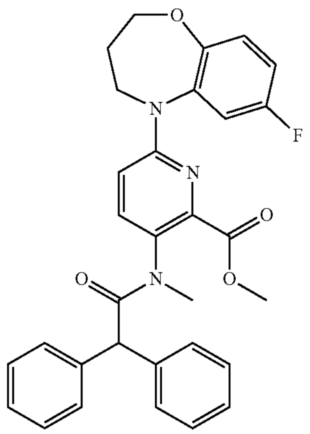 [SMILES: COC(=O)c1nc(N2CCCOc3ccc(F)cc32)ccc1N(C)C(=O)C(c1ccccc1)c1ccccc1] | methyl 6-(7-fluoro-3,4-dihydrobenzo[b][1,4]oxazepine-5(2H)-yl)-3-(N-methyl-2,2-diphenylacetamido)picolinate |
| 9e | 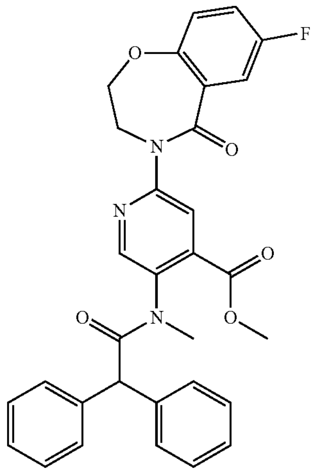 [SMILES: COC(=O)c1cc(N2CCOc3ccc(F)cc3C2=O)ncc1N(C)C(=O)C(c1ccccc1)c1ccccc1] | methyl 2-(7-fluoro-5-oxo-2,3-dihydrobenzo[f][1,4]oxazepine-4(5H)-yl)-5-(N-methyl-2,2-diphenylacetamido) isonicotinate |
| 10f | 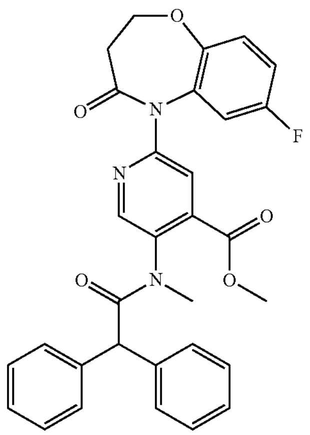 [SMILES: COC(=O)c1cc(N2C(=O)CCOc3ccc(F)cc32)ncc1N(C)C(=O)C(c1ccccc1)c1ccccc1] | methyl 2-(7-fluoro-4-oxo-3,4-dihydrobenzo[b][1,4]oxazepine-5(2H)-yl)-5-(N-methyl-2,2-diphenylacetamido) isonicotinate |

-continued
| compound number | structure | name |
| --- | --- | --- |
| 11d | 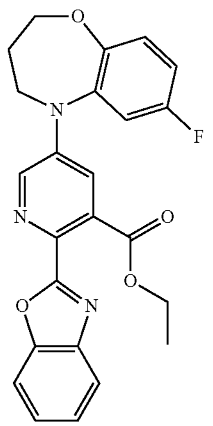 [SMILES: CCOC(=O)c1cc(N2CCCOc3ccc(F)cc32)cnc1-c1nc2ccccc2o1] | ethyl 2-(benzo[d]oxazol-2-yl)-5-(7-fluoro-3,4-dihydrobenzo [b][1,4]oxazepine-5(2H)-yl)nicotinate |
| 12f | 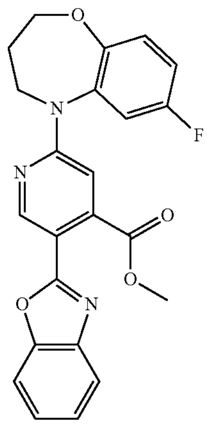 | methyl 5-(benzo[d]oxazol-2-yl)-2-(7-fluoro-3,4-dihydrobenzo [b][1,4]oxazepine-5(2H)-yl)isonicotinate |
| 13c | 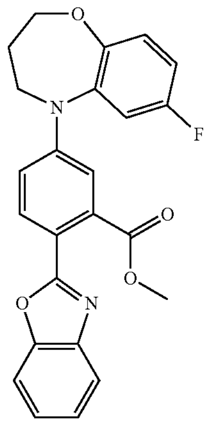 [SMILES: COC(=O)c1cc(N2CCCOc3ccc(F)cc32)ccc1-c1nc2ccccc2o1] | methyl 2-(benzo[d]oxazol-2-yl)-5-(7-fluoro-3,4-dihydrobenzo [b][1,4]oxazepine-5(2H)-yl)benzoate |

-continued
| compound number | structure | name |
| --- | --- | --- |
| 14d | 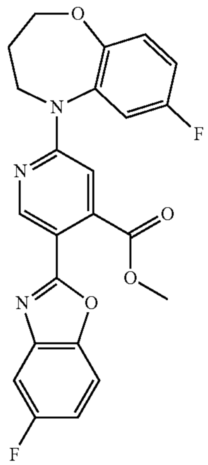 [SMILES: COC(=O)c1cc(N2CCCOc3ccc(F)cc32)ncc1-c1nc2cc(F)ccc2o1] | methyl 2-(7-fluoro-3,4-dihydrobenzo[b][1,4]oxazepine-5(2H)-yl)-5-(5-fluorobenzo[d]oxazol-2-yl)isonicotinate |
| 15d | 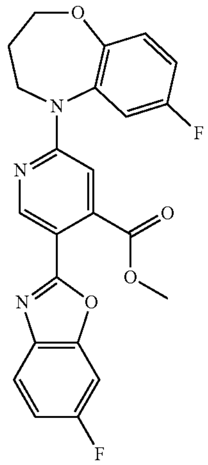 [SMILES: COC(=O)c1cc(N2CCCOc3ccc(F)cc32)ncc1-c1nc2ccc(F)cc2o1] | methyl 2-(7-fluoro-3,4-dihydrobenzo[b][1,4]oxazepine-5(2H)-yl)-5-(6-fluorobenzo[d]oxazol-2-yl)isonicotinate |
| 16d | 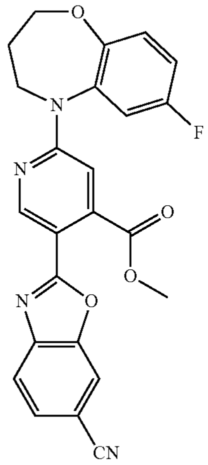 [SMILES: COC(=O)c1cc(N2CCCOc3ccc(F)cc32)ncc1-c1nc2ccc(C#N)cc2o1] | methyl 5-(6-cyanobenzo[d]oxazol-2-yl)-2-(7-fluoro-3,4-dihydro-benzo[b][1,4]oxazepine-5(2H)-yl)isonicotinate |

-continued
| compound number | structure | name |
|---|---|---|
| 17d | 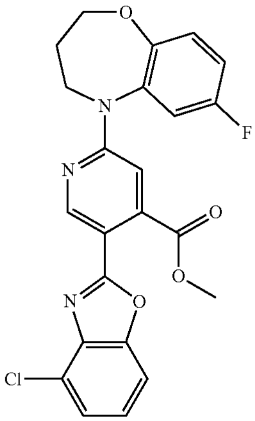 [SMILES: COC(=O)c1cc(N2CCCOc3ccc(F)cc32)ncc1-c1nc2c(Cl)cccc2o1] | methyl 5-(4-chlorobenzo[d]oxazol-2-yl)-2-(7-fluoro-3,4-dihydro-benzo[b][1,4]oxazepine-5(2H)-yl)isonicotinate |
| 18d | 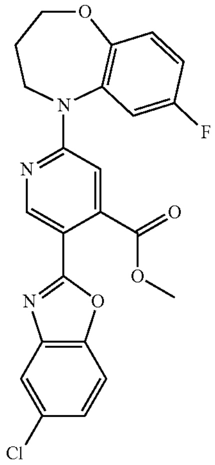 [SMILES: COC(=O)c1cc(N2CCCOc3ccc(F)cc32)ncc1-c1nc2cc(Cl)ccc2o1] | methyl 5-(5-chlorobenzo[d]oxazol-2-yl)-2-(7-fluoro-3,4-dihydro-benzo[b][1,4]oxazepine-5(2H)-yl)isonicotinate |
| 19d | 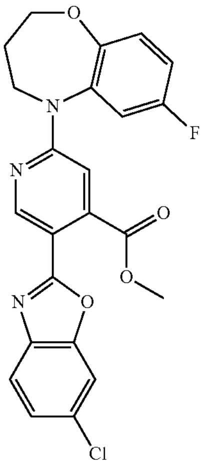 | methyl 5-(6-chlorobenzo[d]oxazol-2-yl)-2-(7-fluoro-3,4-dihydrobenzo[b][1,4]oxazepine-5(2H)-yl) isonicotinate |

-continued
| compound number | structure | name |
| --- | --- | --- |
| 20d | 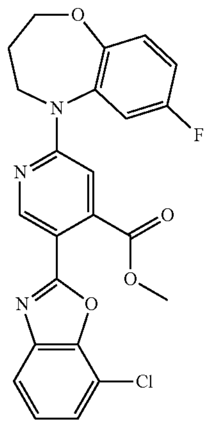 [SMILES: COC(=O)c1cc(N2CCCOc3ccc(F)cc32)ncc1-c1nc2cccc(Cl)c2o1] | methyl 5-(7-chlorobenzo[d]oxazol-2-yl)-2-(7-fluoro-3,4-dihydrobenzo[b][1,4]oxazepine-5(2H)-yl) isonicotinate |
| 21d | 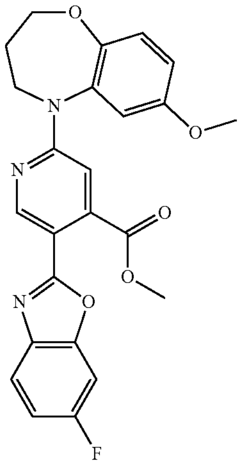 [SMILES: COC(=O)c1cc(N2CCCOc3ccc(OC)cc32)ncc1-c1nc2ccc(F)cc2o1] | methyl 5-(6-fluorobenzo[d]oxazol-2-yl)-2-(7-methoxy-3,4-dihydrobenzo[b][1,4]oxazepine-5(2H)-yl) isonicotinate |
| 22b | 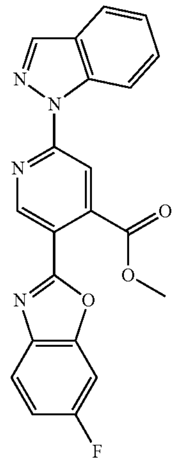 | methyl 5-(6-fluorobenzo[d]oxazol-2-yl)-2-(1H-indazol-1-yl) isonicotinate |

-continued

| compound number | structure | name |
|---|---|---|
| 23b | 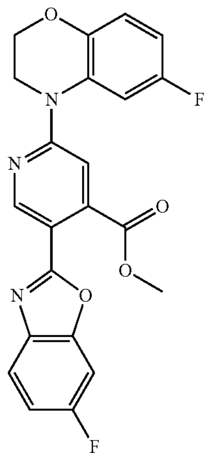 [SMILES: COC(=O)c1cc(N2CCOc3ccc(F)cc32)ncc1-c1nc2ccc(F)cc2o1] | methyl 2-(6-fluoro-2,3-dihydro-4H-benzo[b][1,4]oxazin-4-yl)-5-(6-fluorobenzo[d]oxazol-2-yl) isonicotinate |
| 24b | 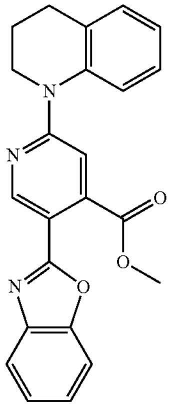 [SMILES: COC(=O)c1cc(N2CCCc3ccccc32)ncc1-c1nc2ccccc2o1] | methyl 5-(benzo[d]oxazol-2-yl)-2-(3,4-dihydroquinoline-1(2H)-yl)isonicotinate |

or a stereoisomer, a tautomer or a pharmaceutically acceptable salt thereof.

Note: If there is a difference between the structure drawn and the name of the structure given, it should be based on the drawn structure.

In another aspect, the present disclosure provides a method for preparing the compound of general formula (I) or the stereoisomer, the tautomer or the pharmaceutically acceptable salt thereof. This method comprises:

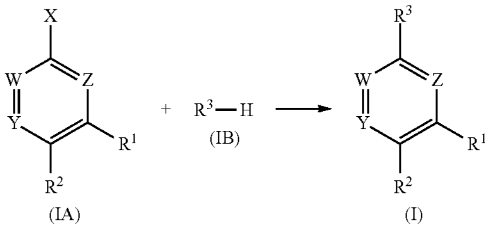

(IA) (IB) (I)

reacting a compound of general formula (IA) with a compound of general formula (IB), to obtain a compound of general formula (I);

when $R^1$ is $COOR^a$ and $R^a$ is alkyl, reacting a compound of general formula (IA) with a compound of general formula (IB), to obtain a compound of general formula (I) with $R^a$ being alkyl;

and optionally further subjecting the compound of general formula (I) with $R^a$ being alkyl to a hydrolysis reaction, to obtain a compound of general formula (I) with $R^a$ being a hydrogen atom;

wherein X is a leaving group which is preferably halogen, and more preferably bromine;

W, Y, Z, $R^1$, $R^2$ and $R^3$ are defined as described in general formula (I).

Furthermore, provided is a method for preparing the compound of general formula (II), or a stereoisomer, a tautomer or a pharmaceutically acceptable salt thereof, which comprises:

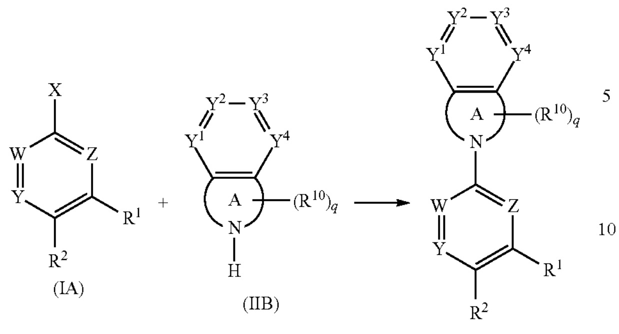

(IA) (IIB) (I)

reacting a compound of general formula (IA) with a general formula (IIB), to obtain a compound of general formula (II);

when $R^1$ is $COOR^a$ and $R^a$ is alkyl, reacting a compound of general formula (IA) with a compound of general formula (JIB), to obtain a compound of general formula (II) with $R^a$ being alkyl;

and optionally further subjecting the compound of general formula (II) with $R^a$ being alkyl to a hydrolysis reaction, to obtain a compound of general formula (II) with $R^a$ being a hydrogen atom;

wherein X is a leaving group which is preferably halogen, and more preferably bromine;

W, Y, Z, $Y^1$, $Y^2$, $Y^3$, $Y^4$, $R^1$, $R^2$, $R^{10}$, q and ring A are defined as described in general formula (II).

Furthermore, provided is a method for preparing the compound of general formula (III) or a stereoisomer, a tautomer or a pharmaceutically acceptable salt thereof, which comprises:

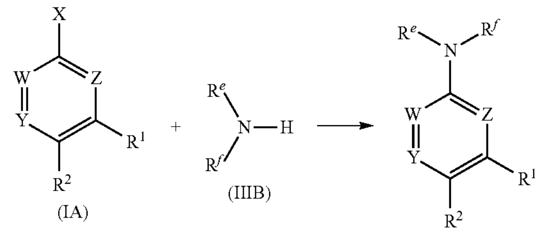

(IA) (IIIB) (III)

reacting a compound of general formula (IA) with a compound of general formula (IIB), to obtain a compound of general formula (III);

when $R^1$ is $COOR^a$, and $R^a$ is alkyl, reacting a compound of general formula (IA) with a compound of general formula (IIIB), to obtain a compound of general formula (III) with $R^a$ being alkyl;

and optionally further subjecting the compound of general formula (III) with $R^a$ being alkyl to a hydrolysis reaction, to obtain a compound of general formula (III) with $R^a$ being a hydrogen atom;

wherein X is a leaving group which is preferably halogen, and more preferably bromine; and W, Y, Z, $R^1$, $R^2$, $R^e$ and $R^f$ are defined as described in general formula (III).

In another aspect, the present disclosure provides a pharmaceutical composition, which comprises an effective dose of compound as represented by general formula (I), (II) or (III) or a stereoisomer, a tautomer or a pharmaceutically acceptable salt thereof, and a pharmaceutically acceptable carrier, excipient or combinations thereof.

In another aspect, the present disclosure provides a method for antagonizing $AT_2R$, comprising contacting the $AT_2R$ receptor with the compound as represented by general formula (I), (II) or (III), or the stereoisomer, the tautomer or the pharmaceutically acceptable salt thereof, or the pharmaceutical composition thereof.

In another aspect, the present disclosure provides use of the compound as represented by general formula (I), (II) or (III), or the stereoisomer, the tautomer or the pharmaceutically acceptable salt thereof, or the pharmaceutical composition thereof in the manufacture of a medicament for treating or preventing a disease mediated by $AT_2R$, wherein the disease mediated by $AT_2R$ is preferably neuropathy or neuropathic pain, wherein the neuropathy or neuropathic pain is preferably primary neuropathy, secondary neuropathy, peripheral neuropathy, neuropathy caused by mechanical or biochemical nerve damage, postherpetic neuralgia, diabetic neuralgia or diabetes-related neurological disorders.

In another aspect, the present disclosure provides use of the compound as represented by general formula (I), (II) or (III), or the stereoisomer, the tautomer or the pharmaceutically acceptable salt thereof, or the pharmaceutical composition thereof in the manufacture of an $AT_2R$ antagonist.

In another aspect, the present disclosure provides use of the compound as represented by general formula (I), (II) or (III), or the stereoisomer, the tautomer or the pharmaceutically acceptable salt thereof, or the pharmaceutical composition thereof in the manufacture of a medicament for treating or preventing neuropathy or neuropathic pain, wherein the neuropathy or neuropathic pain is preferably primary neuropathy, secondary neuropathy, peripheral neuropathy, neuropathy caused by mechanical or biochemical nerve damage, postherpetic neuralgia, diabetic neuralgia or diabetes-related neurological disorders.

Correspondingly, in another aspect, the present disclosure provides a method for treating or preventing a disease mediated by $AT_2R$. This method comprises administering to a subject the compound as represented by general formula (I), (II) or (III) or the stereoisomer, the tautomer or the pharmaceutically acceptable salt thereof, or the pharmaceutical composition containing the compound as represented by general formula (I), (II) or (III), or the stereoisomer, the tautomer or the pharmaceutically acceptable salt thereof. Preferably, the disease mediated by $AT_2R$ is neuropathy or neuropathic pain, more preferably primary neuropathy, secondary neuropathy, peripheral neuropathy, neuropathy caused by mechanical or biochemical nerve damage, postherpetic neuralgia, diabetic neuralgia or diabetes-related neurological disorders.

DETAILED DESCRIPTION OF THE PRESENT DISCLOSURE

Unless stated to the contrary, some terms used in the specification and claims of this disclosure are defined as follows:

When "alkyl" is regarded as a group or a part of a group, it refers to a $C_1$-$C_{20}$ straight chain or branched aliphatic hydrocarbon group. It is preferably $C_1$-$C_{10}$ alkyl, more preferably $C_1$-$C_6$ alkyl or $C_1$-$C_4$ alkyl. Examples of alkyl groups include, but are not limited to, methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1- dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl and the like. Alkyl groups may be substituted or unsubstituted.

“Alkylene” is divalent alkyl groups. It is preferably $C_1$-$C_{10}$ alkylene, more preferably $C_1$-$C_6$ alkylene, and particularly preferably $C_1$-$C_4$ alkylene. Examples of alkylene groups include, but are not limited to, methylene, ethylene, —$C(CH_3)_2$—, n-propylidene and the like. Alkylene groups may be substituted or unsubstituted.

“Alkenyl” refers to alkyl groups as defined above consisting of at least two carbon atoms and at least one carbon-carbon double bond. Representative examples include, but are not limited to, vinyl, 1-propenyl, 2-propenyl, 1-, 2- or 3-butenyl and the like. Alkenyl groups may be optionally substituted or unsubstituted. Particularly preferred is $C_2$-$C_4$ alkenyl.

“Alkynyl” refers to aliphatic hydrocarbon groups containing one carbon-carbon triple bond, which may be straight or branched. Preference is given to $C_2$-$C_{10}$ alkynyl, more preferably $C_2$-$C_6$ alkynyl, and most preferably $C_2$-$C_4$ alkynyl. Examples of alkynyl groups include, but are not limited to, ethynyl, 1-propynyl, 2-propynyl, 1-, 2-, or 3-butynyl and the like. Alkynyl groups may be substituted or unsubstituted.

“Cycloalkyl” refers to saturated or partially saturated monocyclic, fused, bridged, and spirocyclic rings. It is preferably $C_3$-$C_{12}$ cycloalkyl, more preferably $C_3$-$C_8$ cycloalkyl, and most preferably $C_3$-$C_6$ cycloalkyl. Examples of monocyclic cycloalkyl groups include, but are not limited to, cyclopropyl, cyclobutyl, cyclopentyl, cyclopentenyl, cyclohexyl, cyclohexenyl, cyclohexadienyl, cycloheptyl, cycloheptatrienyl, cyclooctyl, and the like. It is preferably cyclopropyl and cyclohexenyl.

“Spirocycloalkyl” refers to polycyclic groups with 5- to 18-membered, two or more cyclic structures, in which the single rings share one carbon atom (called as spiro atom) with each other, and the ring contains one or more double bonds, but none of the rings have fully conjugated η-electron aromatic systems. It is preferably 6- to 14-membered, more preferably 7- to 10-membered rings. According to the number of shared spiro atoms between the rings, spirocycloalkyl is classified into monospiro, dispiro or polyspirocycloalkyl, preferably monospiro and dispirocycloalkyl, more preferably 4-membered/5-membered, 4-membered/6-membered, 5-membered/5-membered or 5-membered/6-membered rings. Non-limiting examples of “spirocycloalkyl” include, but are not limited to: spiro[4.5]decyl, spiro[4.4]nonyl, spiro[3.5]nonyl, and spiro[2.4]heptyl.

“Fused cycloalkyl” refers to 5- to 18-membered full-carbon polycyclic groups containing two or more cyclic structures and sharing a pair of carbon atoms with each other, in which one or more rings may contain one or more double bonds, but none of the rings has a fully conjugated π-electron aromatic system. It is preferably 6- to 12-membered, and more preferably 7- to 10-membered. According to the number of constituent rings, it can be classified into bicyclic, tricyclic, pyridone or polycyclic fused cycloalkyl, preferably bicyclic or tricyclic, more preferably 5-membered/5-membered or 5-membered/6-membered bicyclic alkyl. Non-limiting examples of “fused cycloalkyl” include, but are not limited to: bicyclo[3.1.0]hexyl, bicyclo[3.2.0]heptan-1-enyl, bicyclo[3.2.0]heptyl, decahydronaphthyl or tetradecahydrophenanthryl.

“Bridged cycloalkyl” refers to 5- to 18-membered full-carbon polycyclic groups containing two or more cyclic structures and sharing two carbon atoms that are not directly connected with each other, in which one or more rings may contain one or more double bonds, but none of the rings has fully conjugated π-electron aromatic system. It is preferably 6- to 12-membered, more preferably 7- to 10-membered rings. It is preferably 6- to 14-membered, more preferably 7- to 10-membered rings. According to the number of constituent rings, it can be classified into bicyclic, tricyclic, pyridone or polycyclic bridged cycloalkyl, preferably bicyclic, tricyclic or pyridone, and more preferably bicyclic or tricyclic. Non-limiting examples of “bridged cycloalkyl” include but are not limited to: (1s,4s)-bicyclo[2.2.1]heptyl, bicyclo[3.2.1]octyl, (1s,5s)-bicyclo[3.3.1]nonyl, bicyclo[2.2.2]octyl, (1r,5r)-bicyclo[3.3.2]decyl.

The cycloalkyl ring may be fused to an aryl, heteroaryl or heterocyclyl ring, wherein the ring connected to the parent structure is the cycloalkyl, and its non-limiting examples include indanyl, tetrahydronaphthyl, benzocycloheptyl, and the like. Cycloalkyl may be optionally substituted or unsubstituted.

“Heterocyclyl”, “heterocyclic” or “heterocyclic” are used interchangeably in this application and all refer to non-aromatic heterocyclic groups, in which one or more ring-forming atoms are heteroatoms, such as oxygen, nitrogen, sulfur atoms, including single rings, fused rings, bridged rings and spiro rings. They preferably has a 5- to 7-membered monocyclic ring or a 7- to 10-membered bi- or tricyclic ring, which may contain 1, 2 or 3 atoms selected from nitrogen, oxygen and/or sulfur. Examples of “heterocyclyl” include, but are not limited to, morpholinyl, oxetanyl, thiomorpholinyl, tetrahydropyranyl, 1,1-dioxo-thiomorpholinyl, piperidinyl, 2-oxo-piperidinyl, pyrrolidinyl, 2-oxo-pyrrolidinyl, piperazin-2-one, 8-oxa-3-aza-bicyclo[3.2.1]octyl and piperazinyl. Heterocyclyl may be substituted or unsubstituted.

“Spiroheterocyclyl” refers to 5- to 18-membered polycyclic groups having two or more cyclic structure, with each single ring sharing one common atom between them, and containing one or more double bonds in the ring, but none of the ring has a fully conjugated π-electron aromatic system. One or more ring atoms therein are selected from heteroatoms of nitrogen, oxygen and $S(O)_n$ (n therein is selected from 0, 1 and 2), and the rest ring atoms are carbon. It is preferably 6- to 14-membered, and more preferably 7- to 10-membered rings. According to the number of spiro atoms shared between the rings, spirocyclic alkyl is classified into monospiroheterocyclyl, dispiroheterocyclyl or polyspiroheterocyclyl, and preferably monospiroheterocyclyl or dispiroheterocyclyl. More preferably, it is 4-membered/4-membered, 4-membered/5-membered, 4-membered/6-membered, 5-membered/5-membered, or 5-membered/6-membered monospiroheterocyclyl. Non-limiting examples of “spiroheterocyclyl” include, but are not limited to: 1,7-dioxaspiro[4.5]decyl, 2-oxa-7-azaspiro[4.4]nonyl, 7-oxospiro[3.5]nonyl and 5-oxaspiro[2.4]heptyl.

“Fused heterocyclyl” refers to full-carbon polycyclic groups having two or more ring structures and sharing a pair of atoms with each other, in which one or more rings may contain one or more double bonds, but none of the rings has a fully conjugated 71-electron aromatic system, and in which one or more ring atoms are selected from heteroatoms of nitrogen, oxygen and $S(O)_n$ (where n is selected from 0, 1 and 2), and the rest ring atoms are carbon. It is preferably 6- to 14-membered, and more preferably 7- to 10-membered rings. According to the number of constituent rings, it may be classified into bicyclic, tricyclic, pyridone or polycyclic fused heterocyclyl, preferably bicyclic or tricyclic, and more preferably 5-membered/5-membered or 5-membered/6-membered bicyclic fused heterocyclyl. Non-limiting examples of "fused heterocyclyl" include, but are not limited to: octahydropyrrolo[3,4-c]pyrrolyl, octahydro-1H-isoindolyl, 3-azabicyclo[3.1.0]hexyl, and octahydrobenzo [b][1,4]dioxine.

"Bridged heterocyclyl" refers to 5- to 14-membered, or 5- to 18-membered polycyclic groups containing two or more cyclic structures and sharing two atoms that are not directly connected to each other, in which one or more rings may contain one or more double bonds, but none of the rings has fully conjugated π electrons aromatic systems, and in which one or more ring atoms are selected from heteroatoms of nitrogen, oxygen and $S(O)_n$ (where n is selected from 0, 1 and 2), and the rest of the ring atoms are carbon. It is preferably 6- to 14-membered, and more preferably 7- to 10-membered rings. According to the number of constituent rings, it may be classified into bicyclic, tricyclic, pyridone or polycyclic bridged heterocyclyl, preferably bicyclic, or tricyclic or pyridone, and more preferably bicyclic or tricyclic.

Non-limiting examples of "fused heterocyclyl" include, but are not limited to: 2-azabicyclo[2.2.1]heptyl, 2-azabicyclo[2.2.2]octyl and 2-Azabicyclo[3.3.2]decyl.

The heterocyclic ring may be fused to an aryl, heteroaryl or cycloalkyl ring, wherein the ring connected to the parent structure is the heterocyclyl. Heterocyclyl may be optionally substituted or unsubstituted.

"Aryl" refers to a carbocyclic aromatic system containing one or two rings, wherein the rings can be joined together in a fused manner. The term "aryl" includes aromatic groups such as phenyl, naphthyl, and tetrahydronaphthyl. Preferably, the aryl group is $C_6$-$C_{10}$ aryl, more preferably phenyl or naphthyl, and most preferably phenyl. Aryl may be substituted or unsubstituted. The "aryl" can be fused with heteroaryl, heterocyclyl or cycloalkyl, wherein the ring connected to the parent structure is the aryl. Non-limiting examples include but are not limited to:

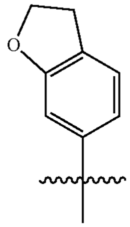
,
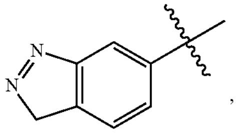
,
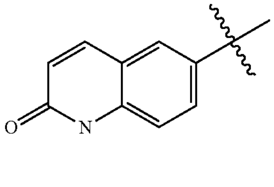
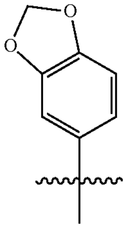
and
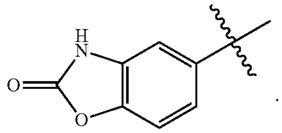
.

"Heteroaryl" refers to an aromatic 5- to 6-membered monocyclic ring or 8- to 10-membered bicyclic ring, which may contain 1 to 4, and preferably 1 to 2 atoms selected from nitrogen, oxygen and/or sulfur. Examples of "heteroaryl" include, but are not limited to, furyl, pyridyl, 2-oxo-1,2-dihydropyridyl, pyridazinyl, pyrimidinyl, pyrazinyl, thienyl, isoxazolyl, oxazolyl, oxadiazolyl, imidazolyl, pyrrolyl, pyrazolyl, triazolyl, tetrazolyl, thiazolyl, isothiazolyl, 1,2,3-thiadiazolyl, benzodioxolyl, benzothienyl, benzimidazolyl, indolyl, isoindolyl, 1,3-dioxo-isoindolyl, quinolinyl, indazolyl, benzisothiazolyl, benzoxazolyl and benzisoxazolyl. Heteroaryl may be substituted or unsubstituted. The heteroaryl ring may be fused to an aryl, heterocyclic or cycloalkyl ring, wherein the ring connected to the parent structure is the heteroaryl ring. Non-limiting examples include but are not limited to:

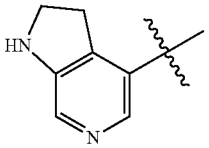
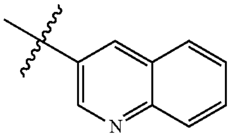
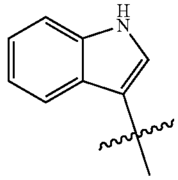
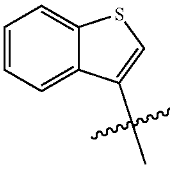
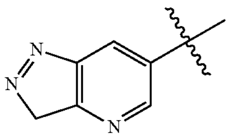
and
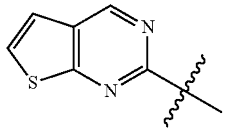
.

"Alkoxy" refers to (alkyl-O—) groups, wherein alkyl is defined as above. $C_1$-$C_6$ and $C_1$-$C_4$ alkoxy are preferred. Examples thereof include, but are not limited to: methoxy, ethoxy, n-propoxy, isopropoxy, n-butoxy, isobutoxy, tert-butoxy and the like.

"Aryloxy" refers to (aryl-O—) groups, wherein the aryl group is defined as above. $C_6$-$C_{10}$ aryloxy is preferred. Examples include, but are not limited to: phenoxy, naphthoxy, and most preferably, phenoxy.

"Hydroxy" refers to —OH groups.

"Halogen" refers to fluoro, chlorine, bromine and iodine.

"Amino" refers to —$NH_2$.

"Cyano" refers to —CN.

"Nitro" refers to —$NO_2$.

"Benzyl" refers to —$CH_2$-phenyl.

"Carboxyl" refers to —C(O)OH.

"Carboxylic ester groups" refers to —C(O)O-alkyl or —C(O)O-cycloalkyl, wherein alkyl, cycloalkyl are defined as above.

"DMSO" refers to dimethyl sulfoxide.

"BOC" refers to tert-butoxycarbonyl.

"Ts" refers to toluenesulfonyl group.

"Leaving group", is an atom or functional group that is detached from a larger molecule in a chemical reaction. It is a term used in nucleophilic substitution reactions and elimination reactions. In the nucleophilic substitution reaction, the reactant attacked by the nucleophile is called the substrate, and the atom or group of atoms that breaks away from the substrate molecule with a pair of electrons is called leaving group. A group that is easy to accept electrons and has a strong ability to withstand negative charges is a good leaving group. When pKa of the conjugate acid of a leaving group is smaller, the leaving group is easier to detach from other molecules. The reason is that when pKa of the conjugate acid is smaller, the corresponding leaving group does not need to be combined with other atoms, and the tendency to exist in the form of an anion (or an electrically neutral leaving group) increases. Common leaving groups include but are not limited to halogen, —OTs or —OH.

"Substituted" refers to one or more hydrogen atoms in the group, preferably up to 5, and more preferably 1-3 hydrogen atoms are each independently substituted with a corresponding number of substituents. Of course, the substituents are only in their possible chemical positions, and those skilled in the art can determine (using experiment or theory) possible or impossible substitutions without too much effort. For example, an amino group or a hydroxyl group having free hydrogen may be unstable when combined with a carbon atom having an unsaturated (e.g., olefinic) bond.

Unless otherwise specified, the "substitution" or "substituted" in this specification means that the group may be substituted by one or more, preferably 1 or 2 or 3 groups selected from the following: alkyl, alkenyl, alkynyl, alkoxy, alkylthio, alkylamino, halogen, mercapto, hydroxyl, nitro, cyano, cycloalkyl, heterocyclyl, aryl, heteroaryl, cycloalkoxy, heterocycloalkoxy, cycloalkylthio, heterocycloalkylthio, amino, haloalkyl, hydroxyalkyl, carboxyl, carboxylic ester groups, =O, $—C(O)R^4$, $—C(O)OR^4$, $—OC(O)R^4$, $—NR^5R^6$, $—C(O)NR^5R^6$, $—SO_2NR^5R^6$ and $—NR^5C(O)R^6$;

$R^4$, $R^5$ and $R^6$ are each independently selected from hydrogen atom, hydroxyl, halogen, nitro, cyano, alkyl, alkoxy, cycloalkyl, heterocyclyl, aryl and heteroaryl, wherein the alkyl, alkoxy, cycloalkyl, heterocyclyl, aryl or heteroaryl is optionally further substituted with one or more substituents selected from hydroxyl, halogen, nitro, cyano, alkyl, alkoxy, cycloalkyl, heterocyclyl, aryl, heteroaryl, $—C(O)R^7$, $—C(O)OR^7$, $—OC(O)R^7$, $—NR^8R^9$, $—C(O)NR^8R^9$, $—SO_2NR^8R^9$ and $—NR^8C(O)R^9$;

or, $R^5$ and $R^6$, together with the N atom connected thereto, form a 4- to 8-membered heterocyclyl, wherein the 4- to 8-membered heterocycle contains one or more N, O or $S(O)_n$, and the 4- to 8-membered heterocycle is optionally further substituted with one or more substituents selected from hydroxyl, halogen, nitro, cyano, alkyl, alkoxy, cycloalkyl, heterocyclyl, aryl, heteroaryl, =O, $—C(O)R^7$, $—C(O)OR^7$, $—OC(O)R^7$, $—NR^8R^9$, $—C(O)NR^8R^9$, $—SO_2NR^8R^9$ and $—NR^8C(O)R^9$;

$R^7$, $R^8$ and $R^9$ are each independently selected from hydrogen, alkyl, cycloalkyl, heterocyclyl, aryl and heteroaryl, wherein the alkyl, cycloalkyl, heterocyclyl, aryl or heteroaryl is optionally further substituted with one or more substituents selected from hydroxyl, halogen, nitro, cyano, alkyl, alkoxy, cycloalkyl, heterocyclyl, aryl, heteroaryl, carboxyl and carboxylic ester groups; and n is selected from 0, 1 and 2.

"Pharmaceutically acceptable salts" refer to certain salts of the above-mentioned compounds capable of maintaining their original biological activity and being suitable for medical use. The pharmaceutically acceptable salt of the compound represented by formula (I) may be a salt formed through reacting carboxyl or amino with a suitable base or acid, for example, a salt formed with a suitable base (including metal salts and ammonium salts), or a salt formed with suitable acids.

"Pharmaceutical composition" means a mixture containing one or more of the compounds described herein or their pharmaceutically acceptable salts or prodrugs and other chemical components and other components such as pharmaceutically acceptable carriers and/or excipients. The purpose of the pharmaceutical composition is to promote the administration to the organism, facilitate the absorption of the active ingredients to exert their biological activity.

DETAILED DESCRIPTION

The following examples are given to further describe the present disclosure, rather than to limit the scope of the present disclosure.

EXAMPLES

Examples show the preparation of representative compounds represented by formula (I) and related structural identification data. It should be noted that the following examples are used to illustrate, rather than to limit, the present disclosure. The $^1H$ NMR spectrum was measured with a Bruker instrument (400 MHz), and the chemical shift was expressed in ppm. Tetramethylsilane was used as internal standard (0.00 ppm). $^1H$ NMR was expressed in a way of: s=singlet, d=doublet, t=triplet, m=multiplet, br=broadened, dd=doublet of doublet, dt=doublet of triplet. If the coupling constant is provided, its unit is Hz.

Mass spectrum was measured by an LC/MS instrument, and ionization was carried out in a manner of ESI or APCI.

Thin layer chromatography silica gel plate used Yantai Huanghai HSGF254 or Qingdao GF254 silica gel plate, the silica gel plate used in thin-layer chromatography (TLC) had a specification of 0.15 mm-0.2 mm, and the specification used for thin layer chromatography separation and purification products was 0.4 mm-0.5 mm.

In column chromatography, Yantai Huanghai silica gel 200-300 mesh silica gel was generally used as a carrier.

In the following examples, unless otherwise specified, all temperatures are expressed in degrees Celsius. Unless otherwise specified, starting materials and reagents are all commercially available or synthesized according to known methods. The commercially available raw materials and reagents were all used directly without further purification. Unless otherwise specified, manufacturers included, but were not limited to, Aldrich Chemical Company, ABCR GmbH & Co. KG, Acros Organics, Guangzan Chemical Technology Co., Ltd. and Jingyan Chemical Technology Co., Ltd.

$CD_3OD$: deuterated methanol.

$CDCl_3$: deuterated chloroform.

DMSO-$d_6$: deuterated dimethyl sulfoxide.

Argon atmosphere refers to the reaction flask connected with an argon balloon having a volume of about 1 L.

In the examples, unless otherwise specified, the solution in the reaction refers to an aqueous solution.

The compounds were purified by using a silica gel column chromatography eluent system and thin layer chromatography. The eluent systems were selected from: petroleum ether-ethyl acetate system A; dichloromethane-methanol system B; and dichloromethane-ethyl acetate system C, in which the volume ratio of the solvent varies according to the compound polarity which may be adjusted by adding a small amount of acidic or alkaline reagents, such as acetic acid or triethylamine, and the like.

Example 1

5-((3-(4-fluorophenyl)propyl)(methyl)amino)-2-(N-methyl-2,2-diphenylacetamido)benzoic acid

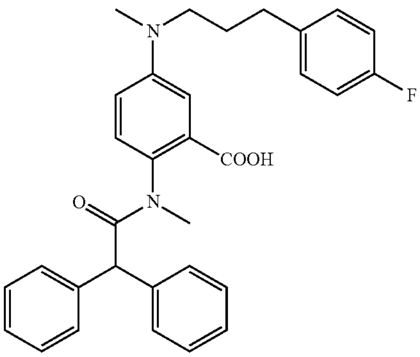

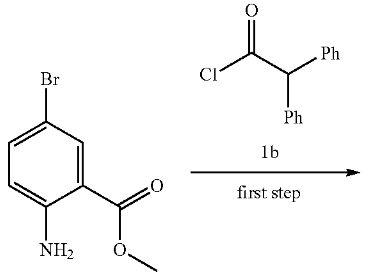

1b

1a

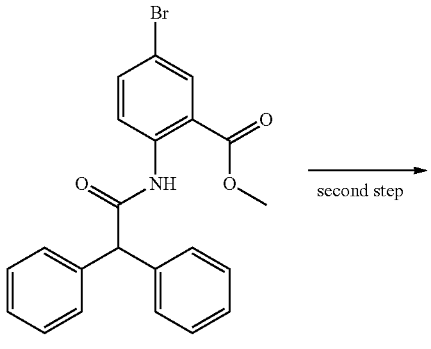

1c

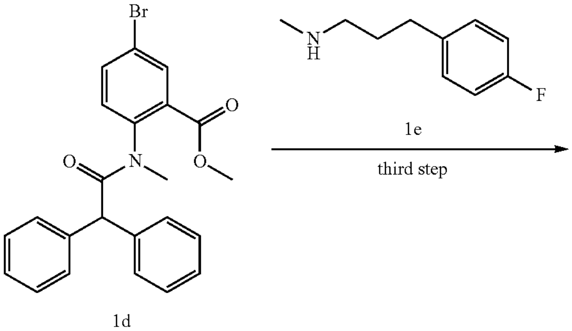

1e

1d

-continued

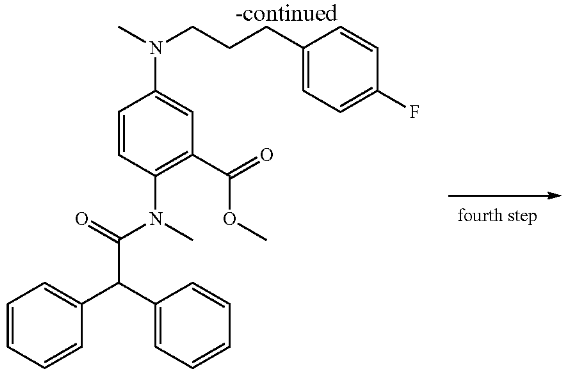

1f

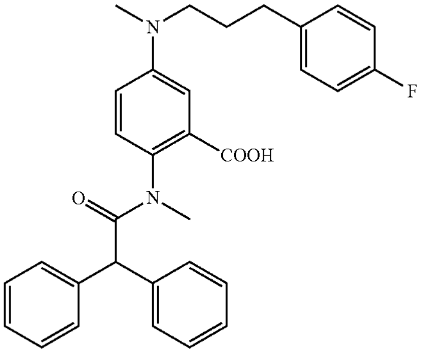

1

First Step methyl 5-bromo-2-(2,2-diphenylacetamido)benzoate

Methyl 2-amino-5-bromobenzoate 1a (3.6 g, 15.6 mmol) and 4-dimethylaminopyridine (180 mg, 1.56 mmol) were dissolved in 24 mL of dichloromethane, to which diphenylacetyl chloride 1b (5.0 g, 21.8 mmol) and triethylamine (3.1 g, 31.2 mmol) were added sequentially, and reacted at room temperature for 4 hours. After the completion of the reaction, the mixture was added with 100 mL of water, and extracted with dichloromethane (50 mL×3). The organic phases were combined, dried over anhydrous sodium sulfate, filtered, and concentrated under reduced pressure. The resulting residue was purified with silica gel column chromatography (eluent: system A), to obtain methyl 5-bromo-2-(2,2-diphenylacetamido)benzoate 1c (6.03 g), with a yield of 91%.

MS m/z (ESI): 423.8 [M+1]

Second Step

Methyl 5-bromo-2-(N-methyl-2,2-diphenylacetamido)benzoate

Methyl 5-bromo-2-(2,2-diphenylacetamido)benzoate 1c (3.9 g, 9.2 mmol) was dissolved in 30 mL of N, N-dimethylformamide, and after being cooled down to 0° C., added with sodium hydride (550 mg, 13.8 mmol) in batches. After addition, the mixture was allowed to rise to room temperature naturally, and stirred for 20 minutes at room temperature, and then added with iodomethane (1.96 g, 13.8 mmol), and reacted at room temperature for 3 hours. After the completion of the reaction, the mixture was added with 50 mL of saturated ammonium chloride solution, and extracted with ethyl acetate (30 mL×3). The organic phases were combined, washed with saturated sodium chloride solution (100 mL), dried over anhydrous sodium sulfate, filtered, and concentrated under reduced pressure. The resulting residue was purified with silica gel column chromatography (eluent: system A), to obtain methyl 5-bromo-2-(N-methyl-2,2-diphenylacetamido)benzoate 1d (3.35 g), with a yield of 83%.

MS m/z (ESI): 437.8[M+1]

Third Step

Methyl 5-((3-(4-fluorophenyl)propyl)(methyl) amino)-2-(N-methyl-2,2-diphenylacetamido)benzoate Under the protection of argon gas, methyl 5-bromo-2-(N-methyl-2,2-diphenylacetamido) benzoate 1d (220 mg, 0.5 mmol), 3-(4-fluorophenyl)-N-methylpropan-1-amine 1e (100 mg, 0.6 mmol, prepared according to the disclosure of patent US 20080188566), tris(dibenzylideneacetone)dipalladium (45.8 mg, 0.05 mmol), 4,5-bis(diphenylphosphino)-9,9-dimethylxanthene (Xantphos, 57.9 mg, 0.1 mmol), and cesium carbonate (250 mg, 0.75 mmol) were mixed with 5 mL of toluene, and reacted at 110-120° C. for 12 hours. After the completion of the reaction, the mixture was cooled down to room temperature, and added with 20 mL of water and 15 mL of ethyl acetate. After liquid separation, the aqueous phase was extracted with ethyl acetate (10 mL×2). The organic phases were combined, dried over anhydrous sodium sulfate, filtered, and concentrated under reduced pressure. The resulting residue was purified with silica gel column chromatography (eluent: system A), to obtain methyl 5-((3-(4-fluorophenyl)propyl)(methyl)amino)-2-(N-methyl-2,2-diphenylacetamido)benzoate if (130 mg), with a yield of 50%.

MS m/z (ESI): 525.0[M+1]

$^1$H NMR (400 MHz, $CDCl_3$) δ 7.24-7.12 (m, 14H), 6.98 (t, J=8.6 Hz, 2H), 6.79 (d, J=8.8 Hz, 1H), 4.80 (s, 1H), 3.55 (s, 3H), 3.41-3.37 (m, 2H), 3.21 (s, 3H), 3.00 (s, 3H), 2.65 (t, J=7.6 Hz, 2H), 1.95-1.90 (m, 2H).

Fourth Step 5-((3-(4-fluorophenyl)propyl)(methyl)amino)-2-(N-methyl-2,2-diphenylacetamido)benzoic acid Methyl 5-((3-(4-fluorophenyl)propyl)(methyl)amino)-2-(N-methyl-2,2-diphenylacetamido)benzoate if (130 mg, 0.25 mmol), and sodium hydroxide (60 mg, 1.5 mmol) were dissolved in 4 mL of a mixed solvent of methanol and water (V:V=3:1), and reacted at 60-70° C. for 1 hour. After the completion of the reaction, the reaction solution was cooled down to room temperature, added with 0.12 mL of concentrated hydrochloric acid for neutralization, and concentrated under reduced pressure. The resulting residue was purified with thin-layer chromatography (developer: system B), to obtain 5-((3-(4-fluorophenyl)propyl)(methyl)amino)-2-(N-methyl-2,2-diphenylacetamido)benzoic acid 1 (75 mg), with a yield of 59%.

MS m/z (ESI): 511.0[M+1]

$^1$H NMR (400 MHz, DMSO-$d_6$) δ 7.26-7.22 (m, 5H), 7.17-7.06 (m, 7H), 7.03-6.99 (m, 3H), 6.40 (d, J=6.8 Hz, 1H), 6.27 (d, J=8.4 Hz, 1H), 4.91 (s, 1H), 3.32-3.31 (m, 2H), 3.07 (s, 3H), 2.88 (s, 3H), 2.58 (t, J=7.4 Hz, 2H), 1.79-1.75 (m, 2H).

Example 2

5-(3,4-dihydrobenzo[b][1,4]oxazepine-5(2H)-yl)-2-(N-methyl-2,2-diphenylacetamido) benzoic acid

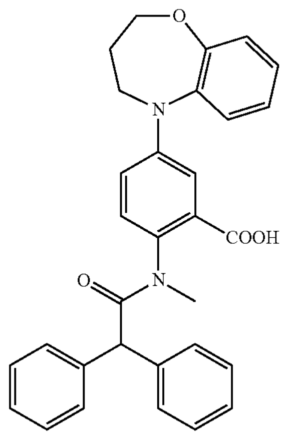

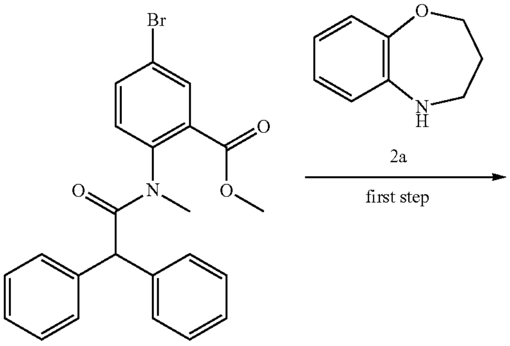

1d

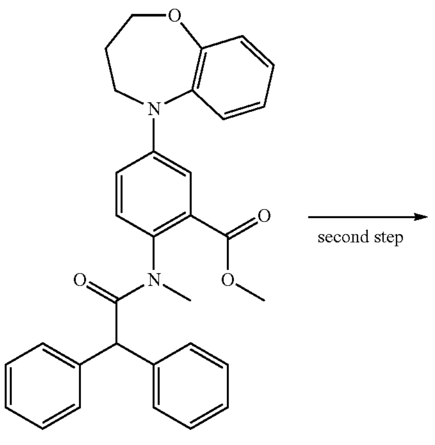

2b

-continued

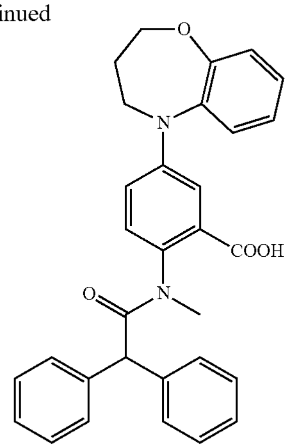

2

First Step

Methyl 5-(3,4-dihydrobenzo[b][1,4]oxazepine-5 (2H)-yl)-2-(N-methyl-2,2-diphenylacetamido) benzoate Under the protection of argon gas, methyl 5-bromo-2-(N-methyl-2,2-diphenylacetamido) benzoate 1d (89 mg, 0.2 mmol), 2,3,4,5-tetrahydrobenzo[b][1,4]oxazepine 2a (36 mg, 0.24 mmol), tris(dibenzylideneacetone)dipalladium (9 mg, 0.01 mmol), 4,5-bis(diphenylphosphino)-9,9-dimethyl-xanthene (Xantphos, 12 mg, 0.02 mmol), and cesium carbonate (98 mg, 0.3 mmol) were mixed with 2 mL of toluene, and reacted at 100-110° C. for 6 hours. After the completion of the reaction, the mixture was cooled down to room temperature, and added with 15 mL of water and 10 mL of ethyl acetate. After liquid separation, the aqueous phase was extracted with ethyl acetate (5 mL×2). The organic phases were combined, dried over anhydrous sodium sulfate, filtered, and concentrated under reduced pressure. The resulting residue was purified with thin-layer chromatography (developer: system A), to obtain methyl 5-(3,4-dihydrobenzo[b][1,4]oxazepine-5-(2H)-yl)-2-(N-methyl-2,2-diphenylacetamido) benzoate 2b (59 mg).

MS m/z (ESI): 507.0[M+1]

$^1$H NMR (400 MHz, $CDCl_3$) δ 7.46 (s, 1H), 7.30-7.02 (m, 14H), 6.82 (d, J=8.8 Hz, 1H), 6.73 (d, J=8.8 Hz, 1H), 4.83 (s, 1H), 4.13-4.09 (m, 2H), 3.94-3.91 (m, 2H), 3.54 (s, 3H), 3.22 (s, 3H), 2.14-2.11 (m, 2H).

Second Step 5-(3,4-dihydrobenzo[b][1,4]oxazepine-5(2H)-yl)-2-(N-methyl-2,2-diphenylacetamido) benzoic acid The methyl 5-(3,4-dihydrobenzo[b][1,4]oxazepine-5 (2H)-yl)-2-(N-methyl-2,2-diphenylacetamido) benzoate 2b (59 mg) obtained from the above step, and sodium hydroxide (24 mg, 0.6 mmol) were dissolved in 2 mL of tetrahydrofuran, heated up to 50-60° C. to reacted for 10 hours. After the completion of the reaction, the reaction solution was cooled down to room temperature, added with concentrated hydrochloric acid for neutralization, and concentrated under reduced pressure. The resulting residue was purified with thin-layer chromatography (developer: system B), to obtain 5-(3,4-dihydrobenzo[b][1,4]oxazepine-5(2H)-yl)-2-(N-methyl-2,2-diphenylacetamido)benzoic acid 2 (29 mg), with a total yield of two-step reaction of 29%.

MS m/z (ESI): 493.0[M+1]

$^1$H NMR (400 MHz, DMSO-$d_6$) δ 7.29-7.02 (m, 15H), 6.85-6.82 (m, 1H), 6.54 (d, J=8.8 Hz, 1H), 4.78 (s, 1H), 4.05 (t, J=5.2 Hz, 2H), 3.87 (br, 2H), 3.09 (s, 3H), 2.04-1.98 (m, 2H).

Example 3

2-(N-methyl-2,2-diphenylacetamido)-5-(2,3,4,5-tetrahydro-1H-benzo[b]azepin-1-yl)benzoic acid

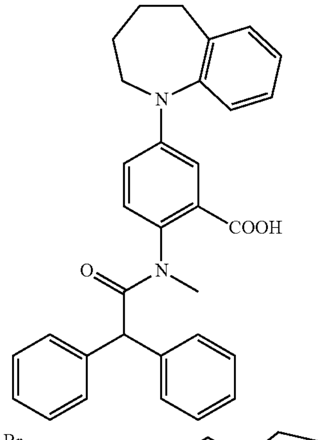

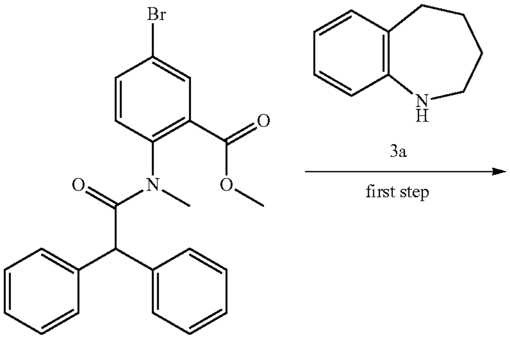

1d

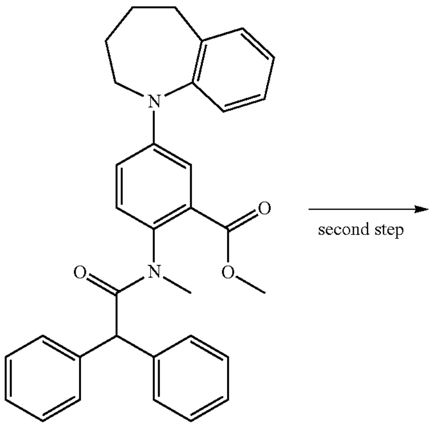

3b

-continued

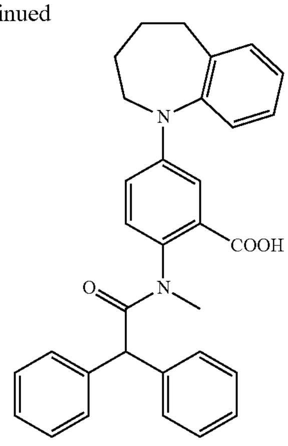

3

First Step

Methyl 2-(N-methyl-2,2-diphenylacetamido)-5-(2,3,4,5-tetrahydro-1H-benzo[b]azepin-1-yl)benzoate Under the protection of argon gas, methyl 5-bromo-2-(N-methyl-2,2-diphenylacetamido) benzoate 1d (300 mg, 0.68 mmol), 2,3,4,5-tetrahydro-1H-benzo[b]azepine 3a (121 mg, 0.82 mmol), tris(dibenzylideneacetone)dipalladium (62.7 mg, 0.068 mmol), 4,5-bis(diphenylphosphino)-9,9-dimethylxanthene (Xantphos, 80 mg, 0.137 mmol), and cesium carbonate (330 mg, 1.03 mmol) were mixed with 5 mL of toluene, and reacted at 110-120° C. for 15 hours. After the completion of the reaction, the mixture was cooled down to room temperature, and added with 20 mL of water and 15 mL of ethyl acetate. After liquid separation, the aqueous phase was extracted with ethyl acetate (10 mL×2). The organic phases were combined, dried over anhydrous sodium sulfate, filtered, and concentrated under reduced pressure. The resulting residue was purified with thin-layer chromatography (developer: system A), to obtain methyl 2-(N-methyl-2,2-diphenylacetamido)-5-(2,3,4,5-tetrahydro-1H-benz[b]azepin-1-yl)benzoate 3b (130 mg).

MS m/z (ESI): 505.0 [M+1]

Second Step 2-(N-methyl-2,2-diphenylacetamido)-5-(2,3,4,5-tetrahydro-1H-benzo[b]azepin-1-yl)benzoic acid The methyl 2-(N-methyl-2,2-diphenylacetamido)-5-(2,3,4,5-tetrahydro-1H-benzo[b]azepin-1-yl)benzoate 3b obtained in the above step, and sodium hydroxide (66 mg, 1.65 mmol) were dissolved in 8 mL of a mixed solvent of methanol and water (V:V=3:1), and heated up to 60-70° C. to reacted for 2 hours. After the completion of the reaction, the reaction solution was cooled down to room temperature, added with 0.132 mL of concentrated hydrochloric acid for neutralization, and concentrated under reduced pressure. The resulting residue was purified with thin-layer chromatography (developer: system B), to obtain 2-(N-methyl-2,2-diphenylacetamido)-5-(2,3,4,5-tetrahydro-1H-benzo[b]azepin-1-yl)benzoic acid 3 (51 mg), with a total yield of two-step reaction of 15%.

MS m/z (ESI): 491.0[M+1]

$^1$H NMR (400 MHz, DMSO-$d_6$) δ 7.36 (d, J=6.8 Hz, 1H), 7.30-7.08 (m, 11H), 7.99 (d, J=6.8 Hz, 2H), 6.86 (s, 1H), 6.34 (d, J=6.8 Hz, 1H), 6.25 (d, J=8.0 Hz, 1H), 4.92 (s, 1H), 3.61 (br, 2H), 3.06 (s, 3H), 2.60-2.59 (m, 2H), 1.77 (br, 2H), 1.63 (br, 2H).

Example 4

5-(7-fluoro-3,4-dihydrobenzo[b][1,4]oxazepine-5(2H)-yl)-2-(N-methyl-2,2-diphenylacetamido)benzoic acid

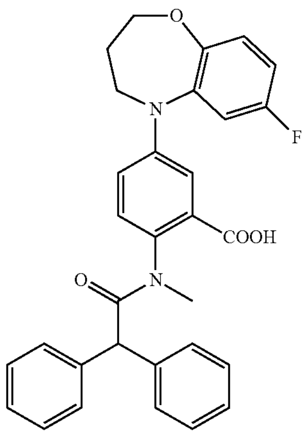

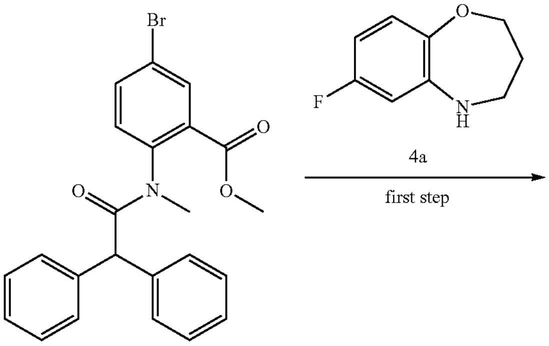

1d

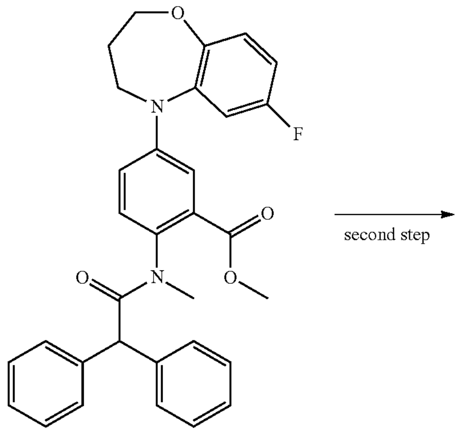

4b

-continued

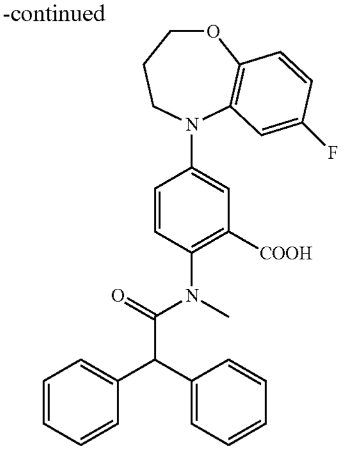

4

First Step

Methyl 5-(7-fluoro-3,4-dihydrobenzo[b][1,4]oxazepine-5(2H)-yl)-2-(N-methyl-2,2-diphenylacetamido)benzoate Under the protection of argon gas, methyl 5-bromo-2-(N-methyl-2,2-diphenylacetamido) benzoate 1d (300 mg, 0.68 mmol), 7-fluoro-2,3,4,5-tetrahydrobenzo[b][1,4]oxazepine 4a (137 mg, 0.82 mmol, prepared according to the disclosure of patent WO 2016142867A1), tris(dibenzylideneacetone) dipalladium (62.7 mg, 0.068 mmol), 4,5-bis(diphenylphosphino)-9,9-dimethylxanthene (Xantphos, 80 mg, 0.137 mmol), and cesium carbonate (330 mg, 1.03 mmol) were mixed with 5 mL of toluene, and reacted at 120° C. for 16 hours. After the completion of the reaction, the mixture was cooled down to room temperature, and added with 20 mL of water and 15 mL of ethyl acetate. After liquid separation, the aqueous phase was extracted with ethyl acetate (10 mL×2). The organic phases were combined, dried over anhydrous sodium sulfate, filtered, and concentrated under reduced pressure. The resulting residue was purified with silica gel column chromatography (eluent: system A), to obtain methyl 5-(7-fluoro-3,4-dihydrobenzo[b][1,4]oxazepine-5(2H)-yl)-2-(N-methyl-2,2-diphenylacetamido)benzoate 4b (178 mg), with a yield of 52%.

MS m/z (ESI): 525.0[M+1]

Second Step 5-(7-fluoro-3,4-dihydrobenzo[b][1,4]oxazepine-5(2H)-yl)-2-(N-methyl-2,2-diphenylacetamido)benzoic acid Methyl 5-(7-fluoro-3,4-dihydrobenzo[b][1,4]oxazepine-5(2H)-yl)-2-(N-methyl-2,2-diphenylacetamido)benzoate 4b (178 mg, 0.34 mmol), and sodium hydroxide (81 mg, 2.04 mmol) were dissolved in 6 mL of a mixed solvent of methanol and water (V:V=5:1), and heated up to 60-70° C. to reacted for 2 hours. After the completion of the reaction, the reaction solution was cooled down to room temperature, added with concentrated hydrochloric acid until its pH value reached about 3, and concentrated under reduced pressure. The resulting residue was purified with silica gel column chromatography (eluent: system B), to obtain 5-(7-fluoro-3,4-dihydrobenzo[b][1,4]oxazepine-5(2H)-yl)-2-(N-methyl-2,2-diphenylacetamido)benzoic acid 4 (80 mg), with a yield of 46%.

MS m/z (ESI): 511.0[M+1]

$^1$H NMR (400 MHz, $CDCl_3$) δ 7.57 (s, 1H), 7.25-7.04 (m, 11H), 6.90-6.84 (m, 3H), 6.65 (d, J=8.8 Hz, 1H), 4.83 (s, 1H), 4.11 (s, 2H), 3.97-3.87 (m, 2H), 3.21 (s, 3H), 2.13-2.10 (m, 2H).

Example 5

2-(7-fluoro-3,4-dihydrobenzo[b][1,4]oxazepine-5(2H)-yl)-5-(N-methyl-2,2-diphenylacetamido)isonicotinic acid

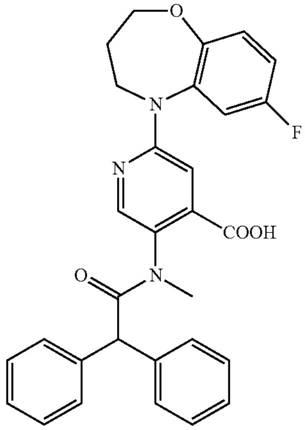

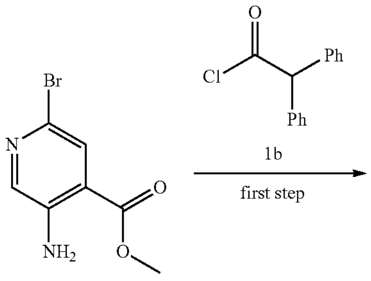

5a

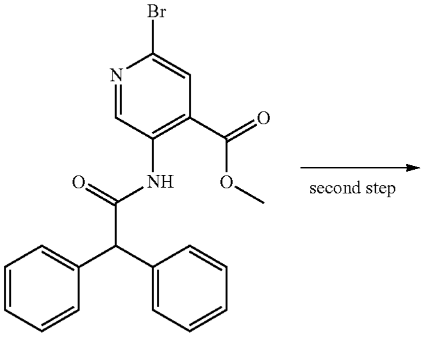

5b

-continued

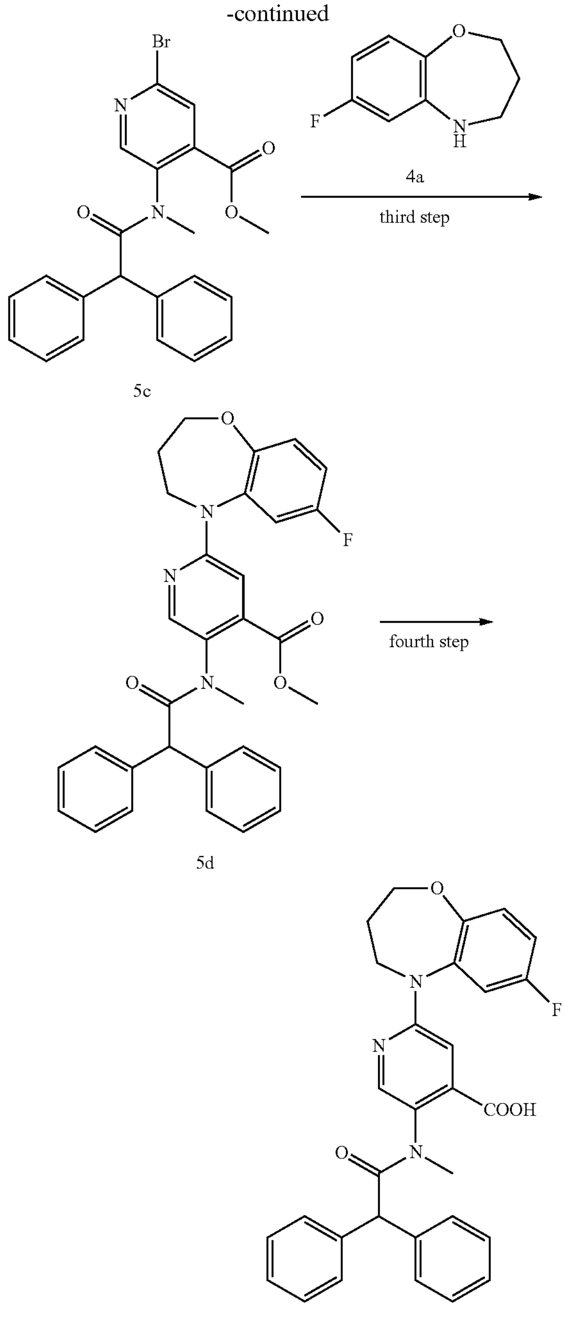

5c
4a
5d
5

First Step methyl 2-bromo-5-(2,2-diphenylacetamido)isonicotinate

Methyl 5-amino-2-bromoisonicotinate 5a (500 mg, 2.16 mmol) and 4-dimethylaminopyridine (26 mg, 0.22 mmol) were dissolved in 8 mL of dichloromethane, added sequentially with diphenylacetyl chloride 1b (1.2 g, 5.41 mmol) and triethylamine (655 mg, 6.49 mmol), and reacted at room temperature for 4 hours. After the completion of the reaction, the mixture was added with 10 mL of water, and extracted with dichloromethane (10 mL×3). The organic phases were combined, dried over anhydrous sodium sulfate, filtered, and concentrated under reduced pressure. The resulting residue was purified with thin-layer chromatography (developer: system A), to obtain methyl 2-bromo-5-(2,2-diphenylacetamido)isonicotinate 5b (500 mg), with a yield of 55%.

MS m/z (ESI): 424.8[M+1]

Second Step

Methyl 2-bromo-5-(N-methyl-2,2-diphenylacetamido)isonicotinate

Methyl 2-bromo-5-(2,2-diphenylacetamido)isonicotinate 5b (400 mg, 0.94 mmol) was dissolved in 8 mL of N,N-dimethylformamide, cooled down to 0° C., added with sodium hydride (45 mg, 1.13 mmol) in batches. After addition, the mixture was allowed to rise to room temperature naturally, stirred at room temperature for 1 hour, then added with iodomethane (160 mg, 1.13 mmol), and reacted at room temperature for 4 hours. After the completion of the reaction, the mixture was added with 10 mL of saturated ammonium chloride solution, and extracted with ethyl acetate (10 mL×3). The organic phases were combined, washed with saturated brine (30 mL), dried over anhydrous sodium sulfate, filtration, and concentrated under reduced pressure. The resulting residue was purified with thin-layer chromatography (developer: system A), to obtain methyl 2-bromo-5-(N-methyl-2,2-diphenylacetamido)isonicotinate 5c (300 mg), with a yield of 73%.

MS m/z (ESI): 438.8[M+1]

Third Step

Methyl 2-(7-fluoro-3,4-dihydrobenzo[b][1,4]oxazepine-5(2H)-yl)-5-(N-methyl-2,2-diphenylacetamido)isonicotinate Under the protection of argon gas, methyl 2-bromo-5-(N-methyl-2,2-diphenylacetamido)isonicotinate 5c (100 mg, 0.23 mmol), 7-fluoro-2,3,4,5-tetrahydrobenzo[b][1,4]oxazepine 4a (46 mg, 0.27 mmol, prepared according to the disclosure of patent WO 2016142867A1), tris(dibenzylideneacetone)dipalladium (21 mg, 0.02 mmol), 4,5-bis(diphenylphosphino)-9,9-dimethylxanthene (Xantphos, 26 mg, 0.05 mmol), and cesium carbonate (111 mg, 0.34 mmol) were mixed with 2 mL of toluene, and reacted at 100-110° C. for 7 hours. After the completion of the reaction, the mixture was cooled down to room temperature, and added with 10 mL of water and 10 mL of ethyl acetate. After liquid separation, the aqueous phase was extracted with ethyl acetate (5 mL×2). The organic phases were combined, dried over anhydrous sodium sulfate, filtered, and concentrated under reduced pressure. The resulting residue was purified with thin-layer chromatography (developer: system A), to obtain methyl 2-(7-fluoro-3,4-dihydrobenzo[b][1,4]oxazepine-5(2H)-yl)-5-(N-methyl-2,2-diphenylacetamido)isonicotinate 5d (60 mg), with a yield of 48%.

MS m/z (ESI): 525.9[M+1]

Fourth Step 2-(7-fluoro-3,4-dihydrobenzo[b][1,4]oxazepine-5(2H)-yl)-5-(N-methyl-2,2-diphenylacetamido)isonicotinic acid Methyl 2-(7-fluoro-3,4-dihydrobenzo[b][1,4]oxazepine-5(2H)-yl)-5-(N-methyl-2,2-diphenylacetamido)isonicotinate 5d (60 mg, 0.11 mmol) and lithium hydroxide monohydrate (10 mg, 0.23 mmol) were dissolved in 2 mL of tetrahydrofuran, and then added with 0.2 mL of water, and reacted at room temperature overnight. After the completion of the reaction, the reaction solution was added with 2N dilute hydrochloric acid to adjust its pH value to about 3, and concentrated under reduced pressure. The resulting residue was separated and purified with a preparative column, to obtain 2-(7-fluoro-3,4-dihydrobenzo[b][1,4]oxazepine-5(2H)-yl)-5-(N-methyl-2,2-diphenylacetamido)isonicotinic acid 5 (16.5 mg), with a yield of 29%.

MS m/z (ESI): 512.0[M+1]

$^1$H NMR (400 MHz, DMSO-$d_6$) δ 7.50 (s, 1H), 7.33-7.05 (m, 13H), 6.92 (s, 1H), 4.77 (s, 1H), 4.08-4.00 (m, 4H), 3.10 (s, 3H), 2.00-1.92 (m, 2H).

Example 6

2-(7,8-difluoro-3,4-dihydrobenzo[b][1,4]oxazepine-5(2H)-yl)-5-(N-methyl-2,2-diphenylacetamido)isonicotinic acid

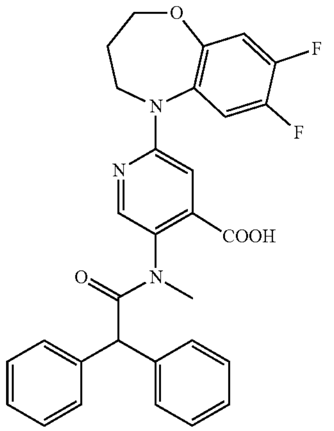

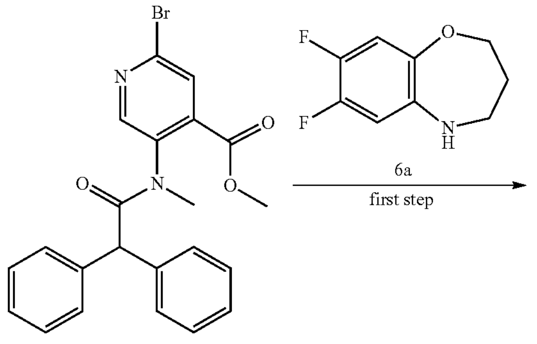

6a

5c

-continued

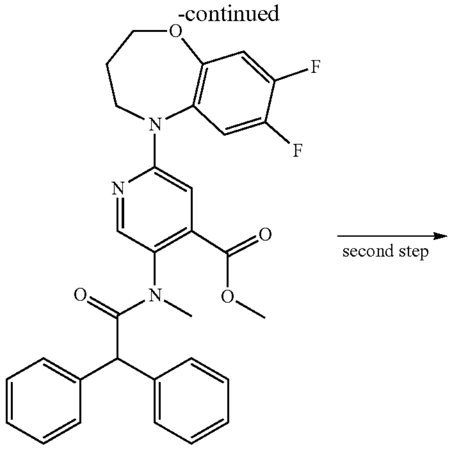

6b

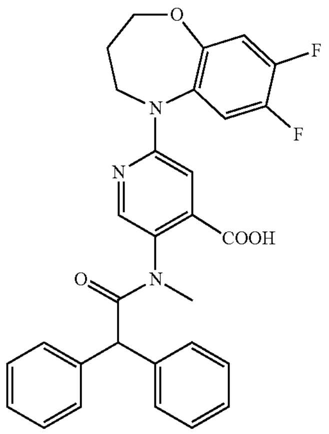

6

First Step

Methyl 2-(7,8-difluoro-3,4-dihydrobenzo[b][1,4]oxazepine-5(2H)-yl)-5-(N-methyl-2,2-diphenylacetamido)isonicotinate Under the protection of argon gas, methyl 2-bromo-5-(N-methyl-2,2-diphenylacetamido)isonicotinate 5c (50 mg, 0.11 mmol), 7,8 di-fluoro-2,3,4,5-tetrahydrobenzo[b][1,4]oxazepine 6a (25 mg, 0.14 mmol, prepared according to the disclosure of patent WO 2016142867A1), tris(dibenzylideneacetone)dipalladium (10 mg, 0.01 mmol), 4,5-bis(diphenylphosphino)-9,9-dimethylxanthene (Xantphos, 13 mg, 0.02 mmol), and cesium carbonate (56 mg, 0.17 mmol) were mixed with 2 mL of toluene, and reacted at 100-110° C. for 7 hours. After the completion of the reaction, the mixture was cooled down to room temperature, and added with 10 mL of water and 10 mL of ethyl acetate. After liquid separation, the aqueous phase was extracted with ethyl acetate (5 mL×2). The organic phases were combined, dried over anhydrous sodium sulfate, filtered, and concentrated under reduced pressure. The resulting residue was purified with thin-layer chromatography (developer: system A), to obtain methyl 2-(7,8-difluoro-3,4-dihydrobenzo[b][1,4]oxazepine-5(2H)-yl)-5-(N-methyl-2,2-diphenylacetamido)isonicotinate 6b (60 mg), with a yield of 100%.

MS m/z (ESI): 543.9 [M+1]

Second Step 2-(7,8-difluoro-3,4-dihydrobenzo[b][1,4]oxazepine-5(2H)-yl)-5-(N-methyl-2,2-diphenylacetamido)isonicotinic acid Methyl 2-(7,8-difluoro-3,4-dihydrobenzo[b][1,4]oxazepine-5(2H)-yl)-5-(N-methyl-2,2-diphenylacetamido)isonicotinate 6b (60 mg, 0.11 mmol) and lithium hydroxide monohydrate (14 mg, 0.33 mmol) were dissolved in 4 mL of tetrahydrofuran, and then added with 0.4 mL of water, and reacted at room temperature overnight. After the completion of the reaction, the reaction solution was added with 2N dilute hydrochloric acid to adjust it to acidity, and concentrated under reduced pressure. The resulting residue was separated and purified with a preparative column, to obtain 2-(7,8-difluoro-3,4-dihydrobenzo[b][1,4]oxazepine-5(2H)-yl)-5-(N-methyl-2,2-diphenylacetamido)isonicotinic acid 6 (10 mg), with a yield of 17%.

MS m/z (ESI): 529.9 [M+1]

$^1$H NMR (400 MHz, DMSO-$d_6$) δ 13.73 (s, 1H), 7.58 (dd, J=11.6, 8.8 Hz, 1H), 7.47 (s, 1H), 7.32-7.04 (m, 11H), 6.89 (s, 1H), 4.76 (s, 1H), 4.08 (t, J=4.8 Hz, 2H), 3.98 (br, 2H), 3.09 (s, 3H), 1.99-1.95 (m, 2H).

Example 7

2-(7-fluoro-3,4-dihydrobenzo[b][1,4]oxazepine-5(2H)-yl)-5-(N-methyl-2,2-diphenylacetamido)pyrimidyl-4-carboxylic acid

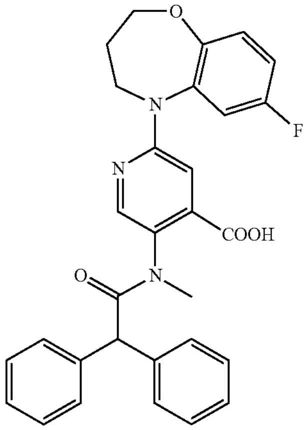

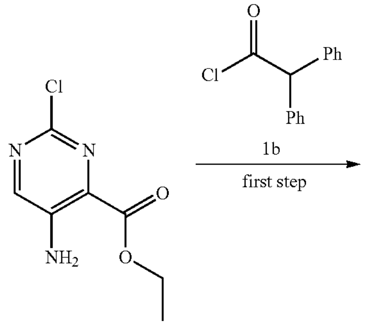

7a

-continued

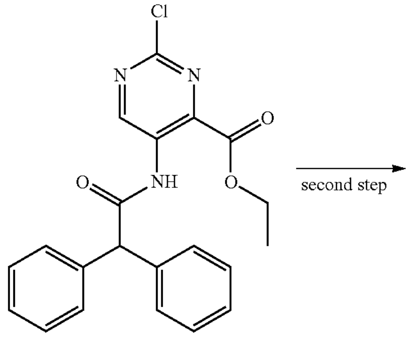

7b

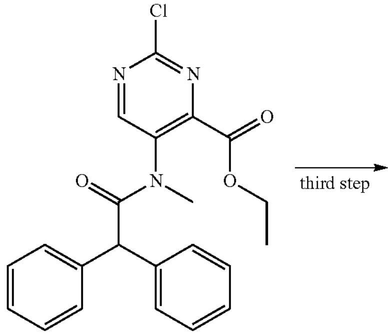

7c

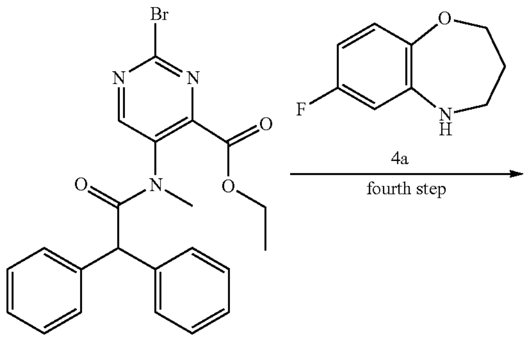

7d

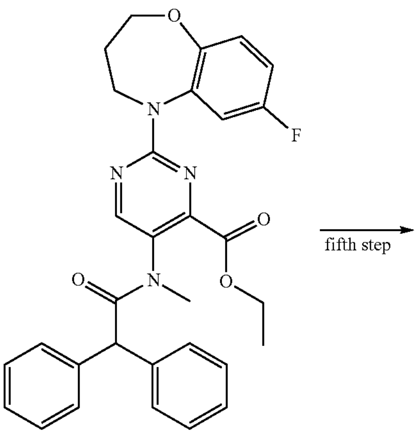

7e

-continued

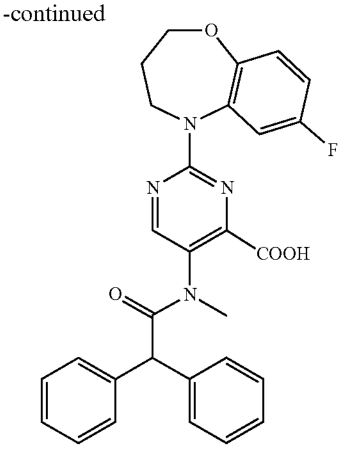

7

First Step

Ethyl 2-chloro-5-(2,2-diphenylacetamido)pyrimidine-4-carboxylate 1-(5-amino-2-chloropyrimidin-4-yl)-1-butanone 7a (500 mg, 2.48 mmol), diphenylacetyl chloride 1b (1.7 g, 7.44 mmol), triethylamine (750 mg, 7.44 mmol) and 4-dimethylaminopyridine (30 mg, 0.25 mmol) were dissolved in 10 mL of dichloromethane, and reacted at room temperature overnight. After the completion of the reaction, the reaction solution was concentrated under reduced pressure. The resulting residue was purified with silica gel column chromatography (mobile phase: system A), to obtain ethyl 2-chloro-5-(2,2-diphenylacetamido)pyrimidine-4-carboxylate 7b (400 mg), with a yield of 41%.

MS m/z (ESI): 395.9[M+1]

Second Step

Ethyl 2-chloro-5-(N-methyl-2,2-diphenylacetamido) pyrimidine-4-carboxylate

Under the protection of argon gas, ethyl 2-chloro-5-(2,2-diphenylacetamido)pyrimidine-4-carboxylate 7b (400 mg, 1.01 mmol) was dissolved in 5 mL of N, N-dimethylformamide, and added with sodium hydride (50 mg, 1.21 mmol) 0° C., stirred at 0° C. for 1 hour, and then added with iodomethane (80 μL, 1.21 mmol), and reacted at room temperature for 3 hours. After the completion of the reaction, the mixture was added with 10 mL of saturated ammonium chloride solution to quench the reaction, and extracted with ethyl acetate (10 mL×2). After liquid separation, the water layer was removed after separation, and the organic phase was dried over anhydrous sodium sulfate, filtered, and concentrated under reduced pressure. The resulting residue was purified with silica gel column chromatography (mobile phase: system A), to obtain ethyl 2-chloro-5-(N-methyl-2,2-diphenylacetamido)pyrimidine-4-carboxylate 7c (400 mg), with a yield of 97%.

MS m/z (ESI): 410.0[M+1]

Third Step

Ethyl 2-bromo-5-(N-methyl-2,2-diphenylacetamido) pyrimidine-4-carboxylate

Ethyl 2-chloro-5-(N-methyl-2,2-diphenylacetamido)pyrimidine-4-carboxylate 7c (300 mg, 0.73 mmol) was dissolved in 5 mL of hydrogen bromide solution in acetic acid, and reacted at room temperature for 1 hour. After the completion of the reaction, the mixture was added with 40 mL of saturated sodium bicarbonate solution, and extracted with 40 mL of ethyl acetate. After liquid separation, the water layer was removed after separation, and the organic phase was dried over anhydrous sodium sulfate, filtered, and concentrated under reduced pressure. The resulting residue was purified with silica gel column chromatography (mobile phase: system A), to obtain ethyl 2-bromo-5-(N-methyl-2,2-diphenylacetamido)pyrimidine-4-carboxylate 7d (330 mg), with a yield of 100%.

MS m/z (ESI): 453.8[M+1]

Fourth Step

Ethyl 2-(7-fluoro-3,4-dihydrobenzo[b][1,4] oxazepine-5(2H)-yl)-5-(N-methyl-2,2-diphenylacetamido)pyrimidine-4-carboxylate Under the protection of argon gas, ethyl 2-bromo-5-(N-methyl-2,2-diphenylacetamido)pyrimidine-4-carboxylate 7d (100 mg, 0.22 mmol), 7-fluoro-2,3,4,5-tetrahydrobenzo [b][1,4]oxazepane 4a (44 mg, 0.26 mmol, prepared according to the disclosure of patent WO 2016142867A1), tris (dibenzylideneacetone)dipalladium (20 mg, 0.02 mmol), 4,5-bis(diphenylphosphino)-9,9-dimethylxanthene (Xantphos, 25 mg, 0.04 mmol), cesium carbonate (108 mg, 0.33 mmol) were mixed with 2 mL of toluene, and reacted at 110° C. for 6 hours. After the completion of the reaction, the mixture was cooled down to room temperature, and added with 10 mL of water and 5 mL of ethyl acetate. After liquid separation, the water layer was removed after separation, and the organic phase was dried over anhydrous sodium sulfate, filtered, and concentrated under reduced pressure. The resulting residue was purified with silica gel column chromatography (eluent: system A), to obtain ethyl 2-(7-fluoro-3,4-dihydrobenzo[b][1,4]oxazepine-5(2H)-yl)-5-(N-methyl-2,2-diphenylacetamido)pyrimidine-4-carboxylate 7e (8 mg), with a yield of 7%.

MS m/z (ESI): 540.9[M+1]

Fifth Step 2-(7-fluoro-3,4-dihydrobenzo[b][1,4]oxazepine-5 (2H)-yl)-5-(N-methyl-2,2-diphenylacetamido)pyrimidyl-4-carboxylic acid Ethyl 2-(7-fluoro-3,4-dihydrobenzo[b][1,4]oxazepine-5 (2H)-yl)-5-(N-methyl-2,2-diphenylacetamido)pyrimidine-4-carboxylate 7e (8 mg, 0.01 mmol) and lithium hydroxide monohydrate (2 mg, 0.04 mmol) were dissolved in 2 mL of tetrahydrofuran, and added with 0.1 mL of water, and reacted at room temperature overnight. After the completion of the reaction, the reaction solution was added with 2N dilute hydrochloric acid to adjust it to acidity, and concentrated under reduced pressure. The resulting residue was separated and purified with a preparative column, to obtain 2-(7-fluoro-3,4-dihydrobenzo[b][1,4]oxazepine-5(2H)-yl)-5-(N-methyl-2,2-diphenylacetamido)pyrimidine-4-carboxylic acid 7 (0.4 mg), with a yield of 5%.

MS m/z (ESI): 512.7[M+1]

Example 8

6-(7-fluoro-3,4-dihydrobenzo[b][1,4]oxazepine-5(2H)-yl)-3-(N-methyl-2,2-diphenylacetamido)picolinic acid

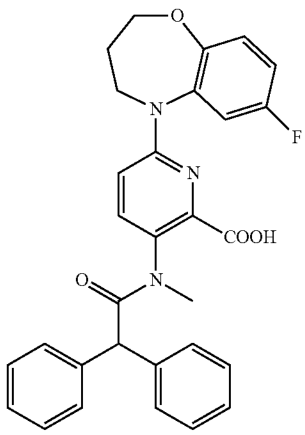

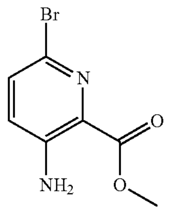

8a

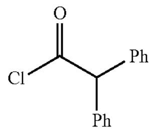

1b first step

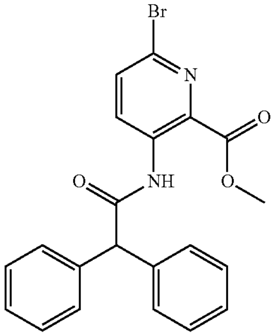

8b second step

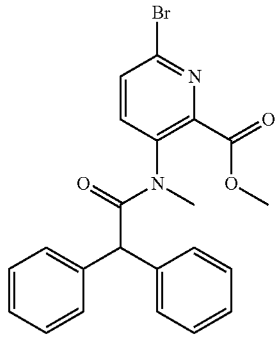

8c

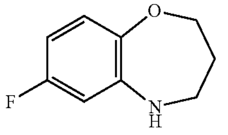

4a third step

-continued

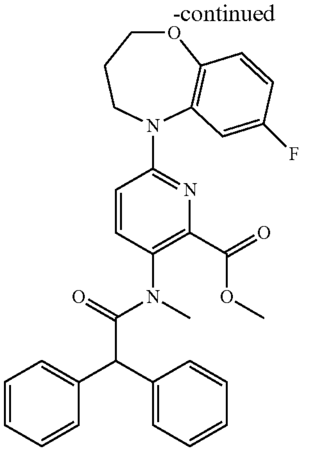

8d fourth step

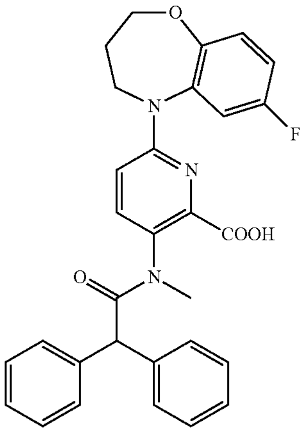

8

First Step

Methyl 6-bromo-3-(2,2-diphenylacetamido)picolinate

Methyl 3-amino-6-bromopicolate 8a (500 mg, 2.16 mmol) and 4-dimethylaminopyridine (26 mg, 0.22 mmol) were dissolved in 10 mL of dichloromethane, and diphenylacetyl chloride 1b (750 mg, 3.25 mmol) and triethylamine (660 mg, 6.49 mmol) were added sequentially, and reacted at room temperature overnight. After the completion of the reaction, the reaction solution was concentrated under reduced pressure. The resulting residue was purified with silica gel column chromatography (mobile phase: system A), to obtain methyl 6-bromo-3-(2,2-diphenylacetamido)picolinate 8b (0.81 g), with a yield of 88%.

MS m/z (ESI): 424.9[M+1]

Second Step

Methyl 6-bromo-3-(N-methyl-2,2-diphenylacetamido)picolinate

Under the protection of argon gas, methyl 6-bromo-3-(2,2-diphenylacetamido)picolinate 8b (1.0 g, 2.36 mmol) was dissolved in 10 mL of anhydrous N,N-dimethylformamide, and added with sodium hydride (113 mg, 2.83 mmol) at 0° C., stirred at 0° C. for 1 hour, and then added with iodomethane (0.2 mL, 2.83 mmol), and reacted at room temperature for 4 hours. After the completion of the reaction, the mixture was added with 20 mL of saturated ammonium chloride solution to quench the reaction, and extracted with 20 mL of ethyl acetate. After liquid separation, the water layer was removed after separation, and the organic phase was dried over anhydrous sodium sulfate, filtered, and concentrated under reduced pressure. The resulting residue was purified with silica gel column chromatography (mobile phase: system A), to obtain methyl 6-bromo-3-(N-methyl-2,2-diphenylacetamido)picolinate 8c (650 mg), with a yield of 63%.

MS m/z (ESI): 438.8[M+1]

Third Step

Methyl 6-(7-fluoro-3,4-dihydrobenzo[b][1,4]oxazepine-5(2H)-yl)-3-(N-methyl-2,2-diphenylacetamido)picolinate Under the protection of argon gas, methyl 6-bromo-3-(N-methyl-2,2-diphenylacetamido)picolinate 8c (100 mg, 0.23 mmol), 7-fluoro-2,3,4,5-tetrahydrobenzo[b][1,4]oxazepane 4a (46 mg, 0.27 mmol, prepared according to the disclosure of patent WO 2016142867A1), tris(dibenzylideneacetone) dipalladium (21 mg, 0.02 mmol), 4,5-bis(diphenylphosphino)-9,9-dimethylxanthene (Xantphos, 26 mg, 0.05 mmol), and cesium carbonate (111 mg, 0.34 mmol) were mixed with 2 mL of toluene, and reacted at 110° C. for 7 hours. After the completion of the reaction, the reaction solution was cooled down to room temperature, and concentrated under reduced pressure. The resulting residue was purified with thin-layer chromatography (developer: system A), to obtain methyl 6-(7-fluoro-3,4-dihydrobenzo[b][1,4]oxazepine-5(2H)-yl)-3-(N-methyl-2,2-diphenylacetamido)picolinate 8d (50 mg), with a yield of 41%.

MS m/z (ESI): 525.9[M+1]

Fourth Step 6-(7-fluoro-3,4-dihydrobenzo[b][1,4]oxazepine-5(2H)-yl)-3-(N-methyl-2,2-diphenylacetamido)picolinic acid Methyl 6-(7-fluoro-3,4-dihydrobenzo[b][1,4]oxazepine-5(2H)-yl)-3-(N-methyl-2,2-diphenylacetamido)picolinate 8d (50 mg, 0.10 mmol) and lithium hydroxide monohydrate (8 mg, 0.19 mmol) were dissolved in 2 mL of tetrahydrofuran, and added with 0.2 mL of water, and reacted at room temperature overnight. After the completion of the reaction, the reaction solution was added with 2N hydrochloric acid to adjust it to acidity, and concentrated under reduced pressure. The resulting residue was separated and purified with a preparative column, to obtain 6-(7-fluoro-3,4-dihydrobenzo[b][1,4]oxazepine-5(2H)-yl)-3-(N-methyl-2,2-diphenylacetamido)picolinic acid 8 (8.94 mg), with a yield of 18%.

MS m/z (ESI): 512.2 [M+1]

$^1$H NMR (400 MHz, DMSO-$d_6$) δ 7.30-7.04 (m, 13H), 6.74 (d, J=8.8 Hz, 1H), 6.39 (d, J=9.2 Hz, 1H), 4.92 (s, 1H), 4.27-3.88 (m, 4H), 3.09 (s, 3H), 2.00 (s, 2H).

Example 9

2-(7-fluoro-5-oxo-2,3-dihydrobenzo[f][1,4]oxazepine-4(5H)-yl)-5-(N-methyl-2,2-diphenylacetamido)isonicotinic acid

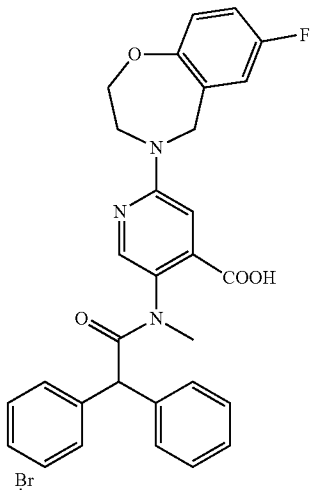

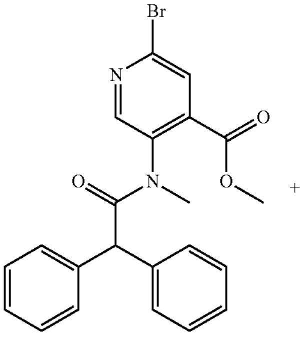

5c

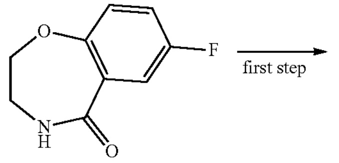

9a

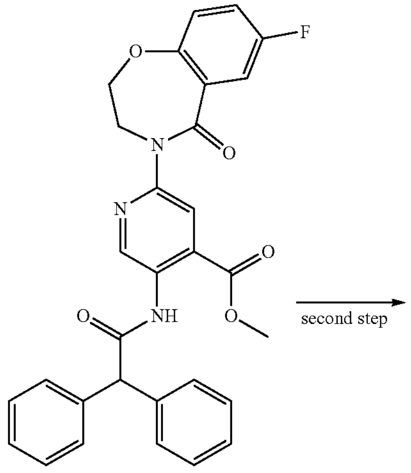

9b

-continued

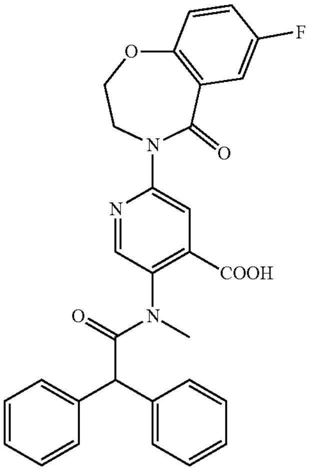

9

First Step

Methyl 2-(7-fluoro-5-oxo-2,3-dihydrobenzo[f][1,4]oxazepine-4(5H)-yl)-5-(N-methyl-2,2-diphenylacetamido)isonicotinate Under argon gas protection, methyl 2-bromo-5-(N-methyl-2,2-diphenylacetamido)isonicotinate 5c (100 mg, 0.2276 mmol), 7-fluoro-3,4-dihydrobenzo[f][1,4]oxazepine-5(2H)-one 9a (50 mg, 0.2731 mmol, prepared according to the disclosure of patent WO 2008051547A1), tris(dibenzylideneacetone)dipalladium (28 mg, 0.03 mmol), 4,5-bis(diphenylphosphino)-9,9-dimethylxanthene (Xantphos, 35 mg, 0.06 mmol) and cesium carbonate (111 mg, 0.34 mmol) were dissolved in 5 mL of toluene, and reacted at 100-102° C. for 5 hours. After the completion of the reaction, the mixture was cooled down to room temperature, added with 5 mL of water, and extracted with ethyl acetate (10 mL×2). The organic phases were combined, dried over anhydrous sodium sulfate, filtered, and concentrated under reduced pressure. The resulting residue was purified with thin-layer chromatography (developer: system A), to obtain methyl 2-(7-fluoro-5-oxo-2,3-dihydrobenzo[f][1,4]oxazepine-4(5H)-yl)-5-(N-methyl-2,2-diphenylacetamido)isonicotinate 9b (100 mg), with a yield of 81%.

MS m/z (ESI): 540.0[M+1]

Second Step 2-(7-fluoro-5-oxo-2,3-dihydrobenzo[f][1,4]oxazepine-4(5H)-yl)-5-(N-methyl-2,2-diphenylacetamido)isonicotinic acid Methyl 2-(7-fluoro-5-oxo-2,3-dihydrobenzo[f][1,4]oxazepine-4(5H)-yl)-5-(N-methyl-2,2-diphenylacetamido)isonicotinate 9b (100 mg, 0.185 mmol) and sodium hydroxide (22 mg, 0.556 mmol) were dissolved in 2 mL of tetrahydrofuran, and added with 0.5 mL of water, and reacted at room temperature. After the completion of the reaction, the reaction solution was added dropwise with 2N dilute hydrochloric acid to adjust its acidity, and extracted with ethyl acetate (20 mL×2). The organic phases were combined, dried over anhydrous sodium sulfate, filtered, and concentrated under reduced pressure. The resulting residue was separated and purified with a preparative column, to obtain 2-(7-fluoro-5-oxo-2,3-dihydrobenzo[f][1,4]oxazepine-4(5H)-yl)-5-(N-methyl-2,2-diphenylacetamido)isonicotinic acid 9 (45 mg), with a yield of 46%.

MS m/z (ESI): 525.7[M+1]

$^1$H NMR (400 MHz, $CDCl_3$) δ 8.88 (s, 1H), 7.81 (s, 1H), 7.55 (dd, J=8.4, 3.2 Hz, 1H), 7.33-7.06 (m, 12H), 4.75 (s, 1H), 4.47-4.35 (m, 4H), 3.24 (s, 3H).

Example 10

2-(7-fluoro-4-oxo-3,4-dihydrobenzo[b][1,4]oxazepine-5(2H)-yl)-5-(N-methyl-2,2-diphenylacetamido)isonicotinic acid

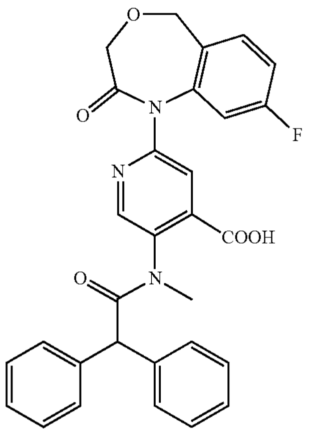

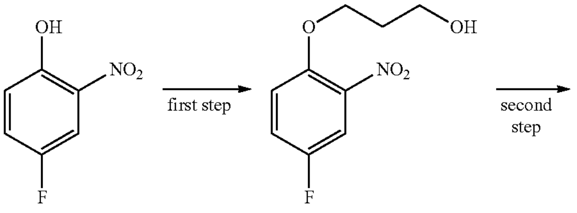

10a 10b

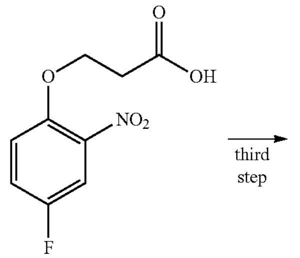

10c

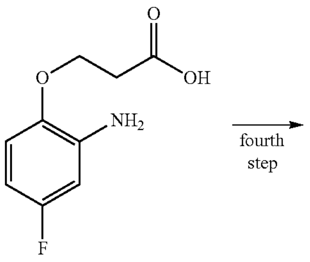

10d

-continued

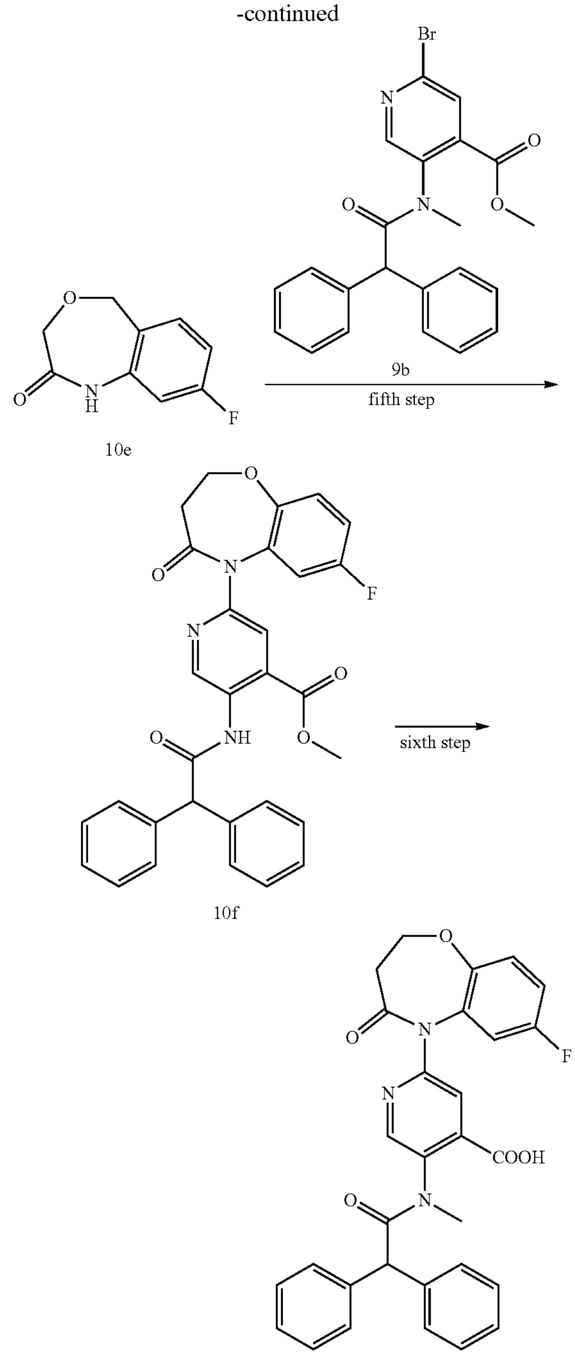

10

First Step 3-(4-fluoro-2-nitrophenoxy)propan-1-ol 2-nitro-4-fluorophenol 10a (10 g, 63.7 mmol), potassium carbonate (26 g, 191 mmol) and potassium iodide (3 g, 19.1 mmol) were dissolved in 100 mL of toluene, added with 5 mL of N,N-dimethylformamide, and refluxed at 120° C. to perform reaction, until no production of water in the reaction. 3-bromo-1-propanol (13 g, 95.5 mmol) was dissolved in 5 mL of N,N-dimethylformamide, and added dropwise to the above-mentioned reaction solution, to continue the reaction at 120° C. for 5 hours. After the completion of the reaction, the mixture was cooled down to room temperature, added with 100 mL of water, and extracted with ethyl acetate (100 mL×2). The organic phases were combined, dried over anhydrous sodium sulfate, filtered, and concentrated under reduced pressure. The resulting residue was purified with silica gel column chromatography (mobile phase: system A), to obtain 3-(4-fluoro-2-nitrophenoxy) propan-1-ol 10b (10.6 g), with a yield of 77%.

Second Step 3-(4-fluoro-2-nitrophenoxy)propionic acid 3-(4-fluoro-2-nitrophenoxy)propan-1-ol 10b (10 g, 46.5, mmol) was dissolved in 150 mL of acetone, and added dropwise to 100 mL of Jones reagent in ice bath, and reacted at room temperature for 6 hours. After the completion of the reaction, the reaction solution was cooled down to 0° C., and slowly added with 100 mL of isopropanol dropwise. When the solution became green, it was filtered. The filtrate was concentrated under reduced pressure. The resulting residue was added with 50 mL of water, and extracted with ethyl acetate (50 mL×3). The organic phases were combined, dried over anhydrous sodium sulfate, filtered, and concentrated under reduced pressure. The resulting residue was purified with silica gel column chromatography (mobile phase: system A), to obtain 3-(4-fluoro-2-nitrophenoxy) propionic acid 10c (8.2 g), with a yield of 77%.

Third Step 3-(2-amino-4-fluorophenoxy)propionic acid 3-(4-fluoro-2-nitrophenoxy)propionic acid 10c (3.0 g, 13.1 mmol) was dissolved in 30 mL of methanol, and added with 10% of palladium on carbon (0.3 g, 10% w). After replacing hydrogen gas, the mixture was stirred at room temperature overnight. After the completion of the reaction, the mixture was filtered, and the filtrate was concentrated under reduced pressure. The resulting residue was purified with silica gel column chromatography (mobile phase: system A), to obtain 3-(2-amino-4-fluorophenoxy)propionic acid 10d (2.6 g), with a yield of 100%.

MS m/z (ESI): 200.1 [M+1]

Fourth Step 7-fluoro-2,3-dihydrobenzo[b][1,4]oxazepine-4(5H)-one 3-(2-amino-4-fluorophenoxy)propionic acid 10d (2.6 g, 13.1 mmol) was dissolved in 30 mL of dichloromethane, and added with dicyclohexylcarbodiimide (2.7 g, 13.1 mmol), and reacted at room temperature for 5 hours. After the completion of the reaction, the reaction solution was concentrated under reduced pressure. The resulting residue was purified with silica gel column chromatography (mobile phase: system A), to obtain 7-fluoro-2,3-dihydrobenzo[b][1,4]oxazepine-4(5H)-one 10e (900 mg), with a yield of 38%.

MS m/z (ESI): 182.1 [M+1]

Fifth Step

Methyl 2-(7-fluoro-4-oxo-3,4-dihydrobenzo[b][1,4]oxazepine-5(2H)-yl)-5-(N-methyl-2,2-diphenylacetamido)isonicotinate Under the protection of argon gas, methyl 2-bromo-5-(2,2-diphenylacetamido)isonicotinate 9b (200 mg, 0.46 mmol), 7-fluoro-2,3-dihydrobenzo[b][1,4]oxazepine-4(5H)-one 10e (100 mg, 0.55 mmol), tris(dibenzylideneacetone)dipalladium (42 mg, 0.05 mmol), 4,5-bis(diphenylphosphino)-9,9-dimethylxanthene (Xantphos, 52 mg, 0.09 mmol) and cesium carbonate (222 mg, 0.68 mmol) were dissolved in 4 mL of toluene, and reacted at 90° C. for 5 hours. After the completion of the reaction, the mixture was cooled down to room temperature, added with 5 mL of water, and extracted with ethyl acetate (10 mL×2). The organic phases were combined, dried over anhydrous sodium sulfate, filtered, and concentrated under reduced pressure. The resulting residue was purified with thin-layer chromatography (developer: system A), to obtain methyl 2-(7-fluoro-4-oxo-3,4-dihydrobenzo[b][1,4]oxazepine-5(2H)-yl)-5-(N-methyl-2,2-diphenylacetamido)isonicotinate 10f (120 mg), with a yield of 48%.

MS m/z (ESI): 540.2[M+1]

Sixth Step 2-(7-fluoro-4-oxo-3,4-dihydrobenzo[b][1,4]oxazepine-5(2H)-yl)-5-(N-methyl-2,2-diphenylacetamido)isonicotinic acid Methyl 2-(7-fluoro-4-oxo-3,4-dihydrobenzo[b][1,4]oxazepine-5(2H)-yl)-5-(N-methyl-2,2-diphenylacetamido)isonicotinate 10f (120 mg, 0.22 mmol) and lithium hydroxide monohydrate (9 mg, 0.22 mmol) were dissolved in 2 mL of tetrahydrofuran, and added with 0.2 mL of water, and reacted at room temperature for 1 hour. After the completion of the reaction, the reaction solution was added with 2N dilute hydrochloric acid to adjust it to acidity, and concentrated under reduced pressure. The resulting residue was separated and purified with a preparative column, to obtain 2-(7-fluoro-4-oxo-3,4-dihydrobenzo[b][1,4]oxazepine-5(2H)-yl)-5-(N-methyl-2,2-diphenylacetamido)isonicotinic acid 10 (12 mg), with a yield of 10%.

MS m/z (ESI): 526.2 [M+1]

$^1H$ NMR (400 MHz, DMSO-$d_6$) δ 14.20 (s, 1H), 8.06 (s, 1H), 7.53 (s, 1H), 7.33-7.05 (m, 12H), 6.89 (dd, J=9.8, 3.0 Hz, 1H), 4.79 (s, 1H), 4.62-4.54 (m, 1H), 4.51-4.45 (m, 1H), 3.14 (s, 3H), 2.95-2.87 (m, 1H), 2.72-2.66 (m, 1H).

Example 11

2-(benzo[d]oxazol-2-yl)-5-(7-fluoro-3,4-dihydrobenzo[b][1,4]oxazepine-5(2H)-yl)nicotinic acid

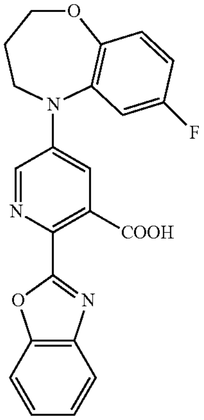

-continued

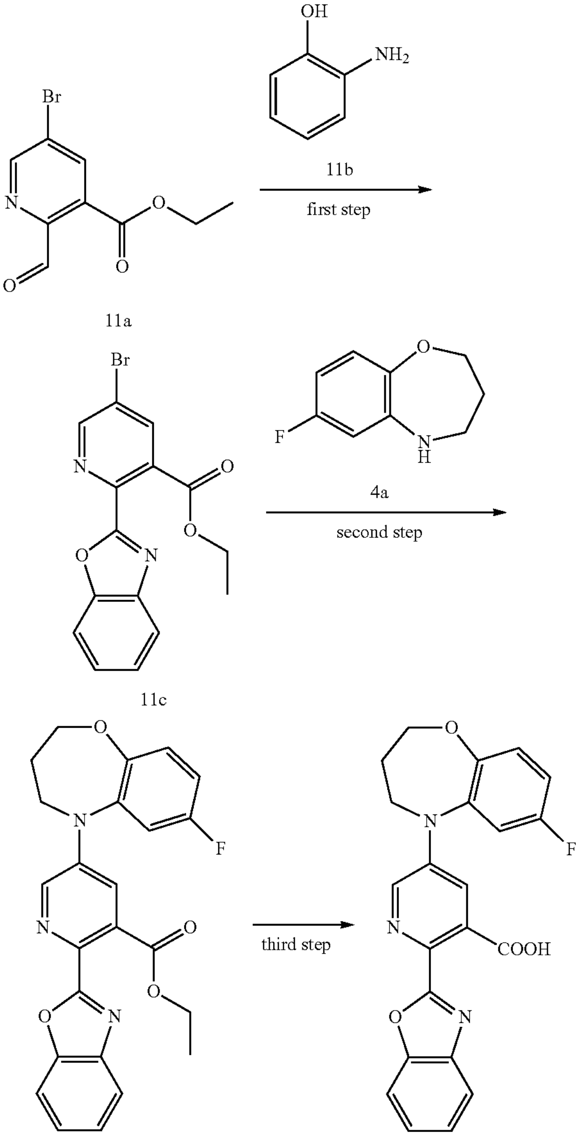

11a
11c
11d
11

First Step

Ethyl 2-(benzo[d]oxazol-2-yl)-5-bromonicotinate

Ethyl 5-bromo-2-formylnicotinate 11a (700 mg, 2.71 mmol, prepared according to the disclosure of patent WO 2012161965 A1) and 2-aminophenol 11b (300 mg, 2.71 mmol) were dissolved in 10 mL of methanol, and stirred at 60° C. overnight. The reaction solution was cooled down to room temperature, and concentrated under reduced pressure to obtain a yellow solid. The solid was dissolved in 20 mL of dichloromethane, then added with 2,3-dichloro-5,6-dicyano-1,4-benzoquinone (920 mg, 4.07 mmol), and stirred to perform reaction. After the completion of the reaction, the reaction solution was concentrated under reduced pressure. The resulting residue was purified with silica gel column chromatography (mobile phase: system A), to obtain ethyl 2-(benzo[d]oxazol-2-yl)-5-bromonicotinate 11c (630 mg), with a yield of 67%.

MS m/z (ESI): 346.8[M+1]

Second Step

Ethyl 2-(benzo[d]oxazol-2-yl)-5-(7-fluoro-3,4-dihydrobenzo[b][1,4]oxazepine-5(2H)-yl)nicotinate Under the protection of argon gas, ethyl 2-(benzo[d]oxazol-2-yl)-5-bromonicotinate 11c (100 mg, 0.29 mmol), 7-fluoro-2,3,4,5-tetrahydrobenzo[b][1,4]oxazepine 4a (58 mg, 0.35 mmol, prepared according to the disclosure of patent WO 2016142867A1), tris(dibenzylideneacetone)dipalladium (26 mg, 0.03 mmol), 4,5-bis(diphenylphosphino)-9,9-dimethylxanthene (Xantphos, 33 mg, 0.06 mmol) and cesium carbonate (140 mg, 0.43 mmol) were dissolved in 2 mL of toluene, and reacted at 110° C. After the completion of the reaction, the mixture was cooled down to room temperature, and added with 5 mL of water, and extracted with ethyl acetate (10 mL×2). The organic phases were combined, dried over anhydrous sodium sulfate, filtered, and concentrated under reduced pressure. The resulting residue was purified with thin-layer chromatography (developer: system A), to obtain ethyl 2-(benzo[d]oxazol-2-yl)-5-(7-fluoro-3,4-dihydrobenzo[b][1,4]oxazepine-5(2H)-yl)nicotinate 11d (80 mg), with a yield of 64%.

MS m/z (ESI): 434.0 [M+1]

Third Step 2-(benzo[d]oxazol-2-yl)-5-(7-fluoro-3,4-dihydrobenzo[b][1,4]oxazepine-5(2H)-yl)nicotinic acid Ethyl 2-(benzo[d]oxazol-2-yl)-5-(7-fluoro-3,4-dihydrobenzo[b][1,4]oxazepine-5(2H)-yl)nicotinate 11d (60 mg, 0.14 mmol) and lithium hydroxide monohydrate (12 mg, 0.28 mmol) were dissolved in 2 mL of tetrahydrofuran, and added with 0.2 mL of water, and reacted at room temperature overnight. After the completion of the reaction, the reaction solution was added with 2N dilute hydrochloric acid to adjust it to acidity, and concentrated under reduced pressure. The resulting residue was separated and purified with a preparative column, to obtain 2-(benzo[d]oxazol-2-yl)-5-(7-fluoro-3,4-dihydrobenzo[b][1,4]oxazepine-5(2H)-yl)nicotinic acid 11 (22.1 mg), with a yield of 39%.

MS m/z (ESI): 405.9 [M+1]

$^1$H NMR (400 MHz, DMSO-$d_6$) δ 13.53 (s, 1H), 8.40 (d, J=2.8 Hz, 1H), 7.80-7.78 (m, 2H), 7.46-7.15 (m, 6H), 4.08 (t, J=5.0 Hz, 2H), 4.01 (t, J=4.6 Hz, 2H), 2.08-2.02 (m, 2H).

Example 12

5-(benzo[d]oxazol-2-yl)-2-(7-fluoro-3,4-dihydrobenzo[b][1,4]oxazepine-5(2H)-yl)isonicotinic acid

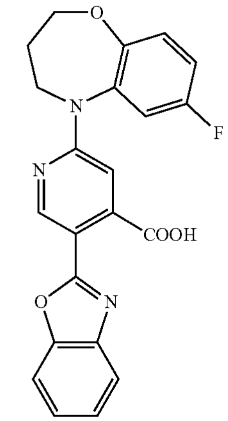

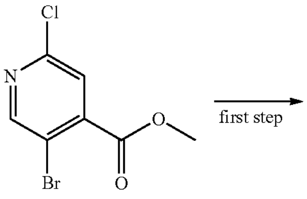

12a

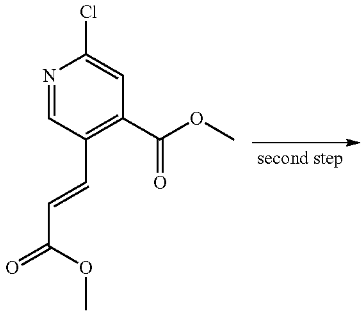

12b

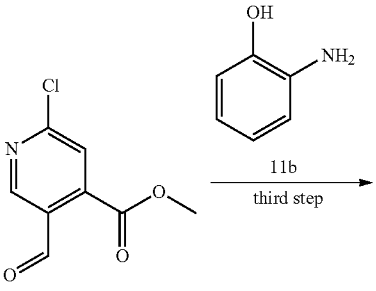

12c

-continued

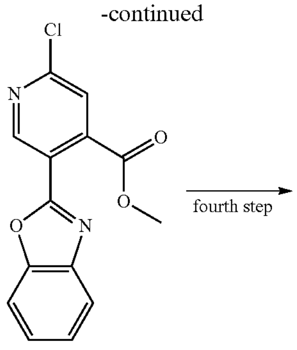

12d

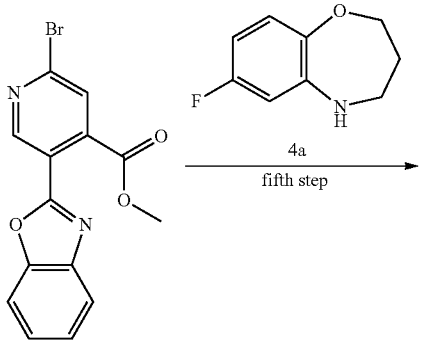

12e

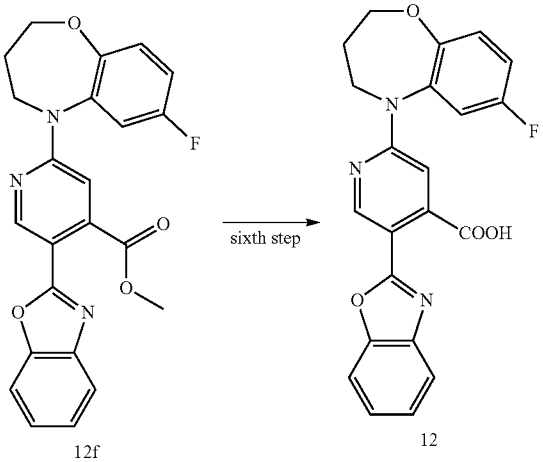

12f

12

First Step

Methyl (E)-2-chloro-5-(3-methoxy-3-oxoprop-1-en-1-yl)isonicotinate

Under nitrogen gas protection, methyl 5-bromo-2-chlorisonicotinate 12a (1.5 g, 6.0 mmol), methyl acrylate (1.55 g, 18.0 mmol), palladium acetate (13.4 mg, 0.06 mmol), tris(o-methoxyphenyl)phosphine (72.9 mg, 0.24 mmol) and triethylamine (3.0 mL, 21.6 mmol) were dissolved in 20 mL of acetonitrile, and reacted at 90-95° C. for 7 hours. After the completion of the reaction, the mixture was cooled down to room temperature, and added with 50 mL of water to precipitate solid, filtered, and dried, to obtain methyl (E)-2-chloro-5-(3-methoxy-3-oxoprop-1-en-1-yl)isonicotinate 12b (700 mg), with a yield of 46%.

MS m/z (ESI): 255.9[M+1]

Second Step methyl 2-chloro-5-formylisonicotinate

Methyl (E)-2-chloro-5-(3-methoxy-3-oxoprop-1-en-1-yl)isonicotinate 12b (500 mg, 1.96 mmol) was dissolved in 100 mL of dichloromethane. After being cooled down to −70-80° C., ozone was introduced for a duration of 20-30 minutes. When the reaction system gradually became blue, it was detected using LC-MS. When the raw material 12b was disappeared, ozone introduction was stopped. The system was added with triphenylphosphine (500 mg, 1.91 mmol), and reacted at room temperature overnight. After the completion of the reaction, the reaction solution was concentrated under reduced pressure. The resulting residue was purified with silica gel column chromatography (mobile phase: system A), to obtain methyl 2-chloro-5-formylisonicotinate 12c (375 mg), with a yield of 96%.

MS m/z (ESI): 199.9 [M+1]

Third Step

Methyl 5-(benzo[d]oxazol-2-yl)-2-chloroisonicotinate

Methyl 2-chloro-5-formylisonicotinate 12c (240 mg, 1.2 mmol), and 2-aminophenol 11b (131 mg, 1.2 mmol) were dissolved in 40 mL of methanol, and reacted at 65-70° C. overnight. The reaction solution was cooled down to room temperature, and concentrated under reduced pressure, to obtain yellow solid. The solid was dissolved in 35 mL of dichloromethane, and then added with 2,3-dichloro-5,6-dicyano-1,4-benzoquinone (273 mg, 1.2 mmol), and reacted at 35° C. for 1 day. After the completion of the reaction, the reaction solution was concentrated under reduced pressure. The resulting residue was purified with silica gel column chromatography (mobile phase: system A), to obtain methyl 5-(benzo[d]oxazol-2-yl)-2-chloroisonicotinate 12d (220 mg), with a yield of 64%.

MS m/z (ESI): 289.0 [M+1]

Fourth Step

Methyl 5-(benzo[d]oxazol-2-yl)-2-bromoisonicotinate

Methyl 5-(benzo[d]oxazol-2-yl)-2-chloroisonicotinate 12d (70 mg, 0.24 mmol) was dissolved in 20 mL of acetonitrile, added with trimethylsilyl bromide (265 mg, 1.73 mmol), and refluxed at 70-80° C. to perform reaction for 3.5 hours, then heated up to 95° C. to continue the reaction overnight. After the completion of the reaction, the reaction solution was cooled down to room temperature, and concentrated under reduced pressure. The resulting residue was purified with thin-layer chromatography (developer: system A), to obtain methyl 5-(benzo[d]oxazol-2-yl)-2-bromoisonicotinate 12e (80 mg), with a yield of 100%.

MS m/z (ESI): 332.8 [M+1]

Fifth Step

Methyl 5-(benzo[d]oxazol-2-yl)-2-(7-fluoro-3,4-dihydrobenzo[b][1,4]oxazepine-5(2H)-yl)isonicotinate Under nitrogen gas atmosphere, methyl 5-(benzo[d]oxazol-2-yl)-2-bromoisonicotinate 12e (80 mg, 0.24 mmol), 7-fluoro-2,3,4,5-tetrahydrobenzo[b][1,4]oxazepine 4a (48 mg, 0.29 mmol, prepared according to the disclosure of patent WO 2016142867A1), tris(dibenzylideneacetone)dipalladium (22 mg, 0.024 mmol), 4,5-bis(diphenylphosphino)-9,9-dimethylxanthene (Xantphos, 28 mg, 0.048 mmol) and cesium carbonate (117 mg, 0.36 mmol) were dissolved in 5 mL of toluene, and reacted at 110-102° C. for 6 hours. After the completion of the reaction, the mixture was cooled down to room temperature, added with 10 mL of water, and extracted with ethyl acetate (20 mL). The organic phase was washed with 10 mL of saturated sodium chloride solution, dried over anhydrous sodium sulfate, filtered, and concentrated under reduced pressure. The resulting residue was purified with thin-layer chromatography (developer: system A), to obtain methyl 5-(benzo[d]oxazol-2-yl)-2-(7-fluoro-3,4-dihydrobenzo[b][1,4]oxazepine-5(2H)-yl)isonicotinate 12f (30 mg), with a yield of 30%.

MS m/z (ESI): 419.9[M+1]

Sixth Step 5-(benzo[d]oxazol-2-yl)-2-(7-fluoro-3,4-dihydrobenzo[b][1,4]oxazepine-5(2H)-yl)isonicotinic acid Methyl 5-(benzo[d]oxazol-2-yl)-2-(7-fluoro-3,4-dihydrobenzo[b][1,4]oxazepine-5(2H)-yl)isonicotinate 12f (30 mg, 0.07 mmol) and sodium hydroxide (30 mg, 0.75 mmol) was dissolved in 5 mL of tetrahydrofuran, added with 2 mL of water, and stirred at room temperature. After the completion of the reaction, the reaction solution was added with 2N dilute hydrochloric acid to adjust it to acidity, extracted with ethyl acetate (5 mL×2). The organic phases were combined, dried over anhydrous sodium sulfate, filtered, and concentrated under reduced pressure. The resulting residue was separated and purified with a preparative column, to obtain 5-(benzo[d]oxazol-2-yl)-2-(7-fluoro-3,4-dihydrobenzo[b][1,4]oxazepine-5(2H)-yl)isonicotinic acid 12 (1.68 mg), with a yield of 5.8%.

MS m/z (ESI): 405.9 [M+1]

Example 13

2-(benzo[d]oxazol-2-yl)-5-(7-fluoro-3,4-dihydrobenzo[b][1,4]oxazepine-5(2H)-yl)benzoic acid

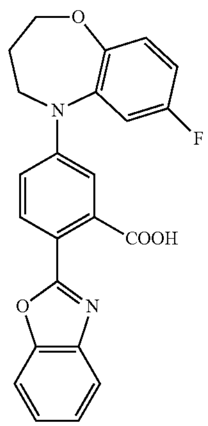

-continued

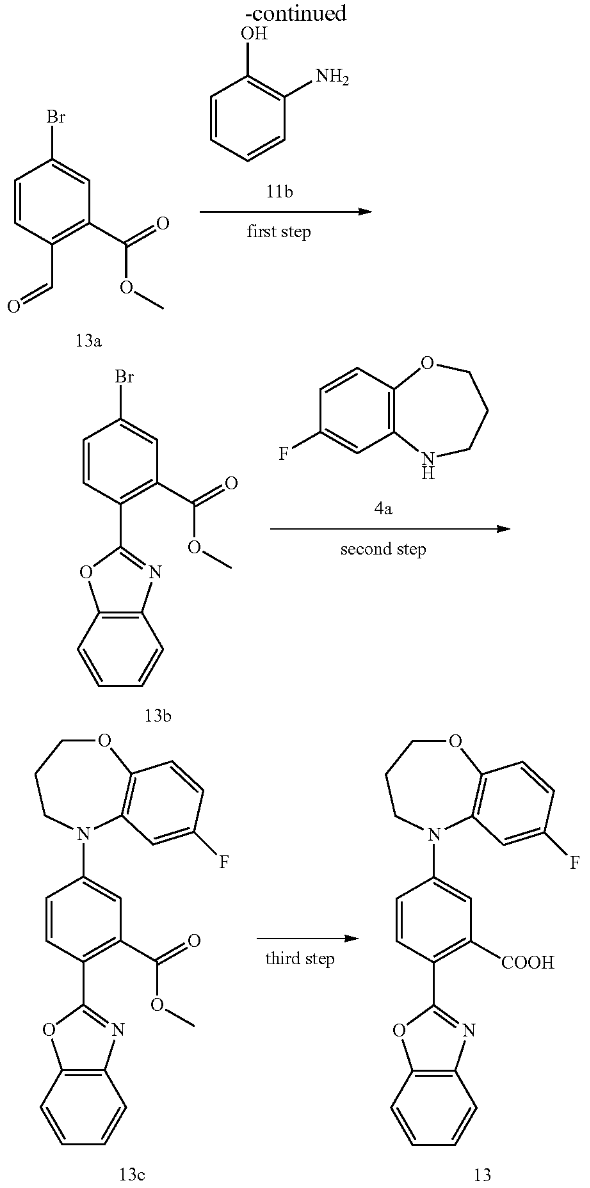

First Step

Methyl 5-bromo-2-formylbenzoate 13a (100 mg, 0.411 mmol) and 2-aminophenol 11b (45 mg, 0.411 mmol) were dissolved in 4 mL of methanol, and reacted at 60° C. for 4 hours. The reaction solution was cooled down to room temperature, concentrated under reduced pressure, dissolved in 8 mL of dichloromethane, and then added with 2,3-dichloro-5,6-dicyano-1,4-benzoquinone (93 mg, 0.411 mmol), and stirred to perform reaction overnight. After the completion of the reaction, the reaction solution was concentrated under reduced pressure. The resulting residue was purified with silica gel column chromatography (mobile phase: system A), to obtain methyl 2-(benzo[d]oxazol-2-yl)-5-bromobenzoate 13b (107 mg), with a yield of 79%.

MS m/z (ESI): 331.8[M+1]

Second Step

Methyl 2-(benzo[d]oxazol-2-yl)-5-(7-fluoro-3,4-dihydrobenzo[b][1,4]oxazepine-5(2H)-yl)benzoate Under argon gas protection, methyl 2-(benzo[d]oxazol-2-yl)-5-bromobenzoate 13b (100 mg, 0.301 mmol), 7-fluoro- 2,3,4,5-tetrahydrobenzo[b][1,4]oxazepine 4a (60.4 mg, 0.361 mmol, prepared according to the disclosure of patent WO 2016142867A1), tris(dibenzylideneacetone)dipalladium (28 mg, 0.0301 mmol), 4,5-bis(diphenylphosphino)-9,9-dimethylxanthene (Xantphos, 35 mg, 0.0602 mmol) and cesium carbonate (147 mg, 0.4515 mmol) were dissolved in 5 mL of toluene, and reacted at 110-102° C. for 7 hours. After the completion of the reaction, the mixture was cooled down to room temperature, added with 10 mL of water, and extracted with ethyl acetate (30 mL). The organic phase was washed with 10 mL of saturated sodium chloride solution, dried over anhydrous sodium sulfate, filtered, and concentrated under reduced pressure. The resulting residue was purified with thin-layer chromatography (developer: system A), to obtain methyl 2-(benzo[d]oxazol-2-yl)-5-(7-fluoro-3,4-dihydrobenzo[b][1,4]oxazepine-5(2H)-yl)benzoate 13c (30 mg), with a yield of 24%.

MS m/z (ESI): 418.9 [M+1]

Third Step 2-(benzo[d]oxazol-2-yl)-5-(7-fluoro-3,4-dihydrobenzo[b][1,4]oxazepine-5(2H)-yl)benzoic acid Methyl 2-(benzo[d]oxazol-2-yl)-5-(7-fluoro-3,4-dihydrobenzo[b][1,4]oxazepine-5(2H)-yl)benzoate 13c (30 mg, 0.0717 mmol) was dissolved in a mixed solvent of 5 mL tetrahydrofuran and 2 mL of water, and added with sodium hydroxide (30 mg, 0.75 mmol), and reacted at 40° C. for 7 hours. After the completion of the reaction, the mixture was added with 2N dilute hydrochloric acid to adjust the reaction system to acidity, and extracted with ethyl acetate (20 mL×3). The organic phases were combined, dried over anhydrous sodium sulfate, filtered, and concentrated under reduced pressure. The resulting residue was separated and purified with a preparative column, to obtain 2-(benzo[d]oxazol-2-yl)-5-(7-fluoro-3,4-dihydrobenzo[b][1,4]oxazepine-5(2H)-yl)benzoic acid 13 (9 mg), with a yield of 31%.

MS m/z (ESI): 405.9[M+1]

$^1$H NMR (400 MHz, DMSO-$d_6$) δ 13.24 (s, 1H), 7.86 (d, J=8.4 Hz, 1H), 7.76-7.69 (m, 2H), 7.41-7.36 (m, 2H), 7.20-7.05 (m, 5H), 4.04 (t, J=5.4 Hz, 2H), 3.95 (t, J=5.8 Hz, 2H), 2.08-1.99 (m, 2H).

Example 14

2-(7-fluoro-3,4-dihydrobenzo[b][1,4]oxazepine-5(2H)-yl)-5-(5-fluorobenzo[d]oxazol-2-yl)isonicotinic acid

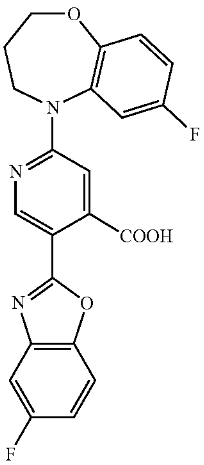

-continued

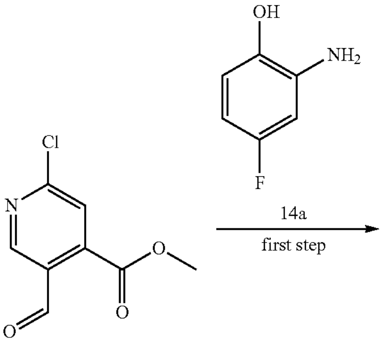

12c

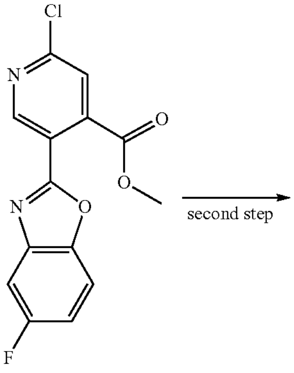

14b

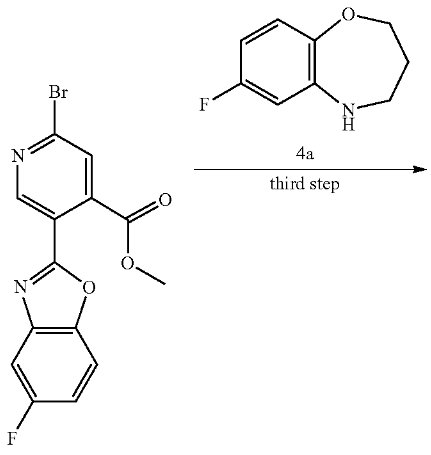

14c

-continued

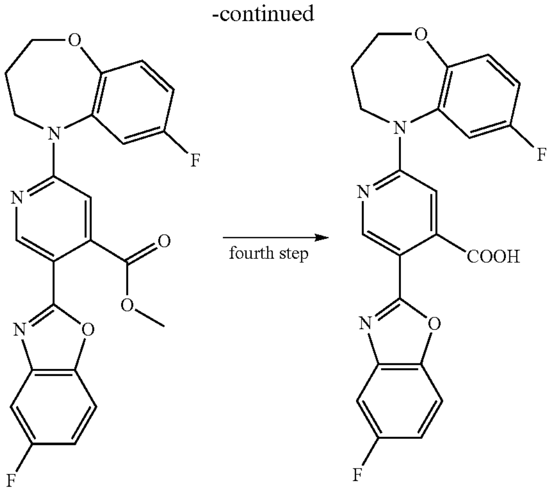

14d

14

First Step

Methyl 2-chloro-5-(5-fluorobenzo[d]oxazol-2-yl) isonicotinate

Methyl 2-chloro-5-formylisonicotinate 12c (200 mg, 1.0 mmol), and 2-amino-4-fluorophenol 14a (127 mg, 1.0 mmol) was dissolved in 15 mL of methanol, and reacted at 85° C. overnight. After the completion of the reaction, the reaction solution was cooled down to room temperature, and concentrated under reduced pressure. The resulting residue was dissolved in 10 mL of dichloromethane, and added to 2,3-dichloro-5,6-dicyano-1,4-benzoquinone (227 mg, 1.0 mmol), and reacted at 35° C. for 1 day. After the completion of the reaction, the reaction solution was concentrated under reduced pressure. The resulting residue was purified with silica gel column chromatography (mobile phase: system A), to obtain methyl 2-chloro-5-(5-fluorobenzo[d]oxazol-2-yl) isonicotinate 14b (190 mg), with a yield of 62%.

MS m/z (ESI): 307.0 [M+1]

Second Step

Methyl 2-bromo-5-(5-fluorobenzo[d]oxazol-2-yl) isonicotinate

Methyl 2-chloro-5-(5-fluorobenzo[d]oxazol-2-yl)isonicotinate 14b (190 mg, 0.619 mmol) was dissolved in 50 mL of acetonitrile, added with trimethylsilyl bromide (678 mg, 4.43 mmol), and refluxed at 100° C. to perform reaction overnight. After the completion of the reaction, the reaction solution was cooled down to room temperature, and concentrated under reduced pressure. To the residue, 30 mL of ethyl acetate and 15 mL of water were added, and added with saturated sodium bicarbonate solution dropwise, to adjust the solution to pH=8, and extracted with ethyl acetate (30 mL×2). The organic phases were combined, dried over anhydrous sodium sulfate, filtered, and concentrated under reduced pressure. The resulting residue was purified with silica gel column chromatography (mobile phase: system A), to obtain methyl 2-bromo-5-(5-fluorobenzo[d]oxazol-2-yl) isonicotinate 14c (80 mg), with a yield of 37%.

MS m/z (ESI): 351.0 [M+1]

Third Step

Methyl 2-(7-fluoro-3,4-dihydrobenzo[b][1,4] oxazepine-5(2H)-yl)-5-(5-fluorobenzo[d]oxazol-2-yl)isonicotinate Under nitrogen gas atmosphere, methyl 2-bromo-5-(5-fluorobenzo[d]oxazol-2-yl)isonicotinate 14c (80 mg, 0.23 mmol), 7-fluoro-2,3,4,5-tetrahydrobenzo[b][1,4]oxazepine 4a (46 mg, 0.27 mmol, prepared according to the disclosure of patent WO 2016142867A1), tris(dibenzylideneacetone) dipalladium (21 mg, 0.023 mmol), 4,5-bis(diphenylphosphino)-9,9-dimethylxanthene (Xantphos, 27 mg, 0.046 mmol) and cesium carbonate (297 mg, 0.91 mmol) were dissolved in 5 mL of toluene, and reacted at 100-102° C. for 2 hours. After the completion of the reaction, the mixture was cooled down to room temperature, added with 5 mL of water, and extracted with ethyl acetate (10 mL). The organic phase was washed with 10 mL of saturated sodium chloride solution, dried over anhydrous sodium sulfate, filtered, and concentrated under reduced pressure. The resulting residue was purified with silica gel column chromatography (mobile phase: system A), to obtain methyl 2-(7-fluoro-3,4-dihydrobenzo[b][1,4]oxazepine-5(2H)-yl)-5-(5-fluorobenzo[d] oxazol-2-yl)isonicotinate 14d (11 mg), with a yield of 11%.

MS m/z (ESI): 437.9 [M+1]

$^1$H NMR (400 MHz, $CDCl_3$) δ 8.98 (s, 1H), 7.44 (dd, J=9.0, 4.2 Hz, 1H), 7.39 (dd, J=8.6, 2.6 Hz, 1H), 7.15-6.94 (m, 4H), 6.66 (s, 1H), 4.09 (br, 4H), 3.87 (s, 3H), 2.14-2.08 (m, 2H).

Fourth Step 2-(7-fluoro-3,4-dihydrobenzo[b][1,4]oxazepine-5 (2H)-yl)-5-(5-fluorobenzo[d]oxazol-2-yl)isonicotinic acid Methyl 2-(7-fluoro-3,4-dihydrobenzo[b][1,4]oxazepine-5 (2H)-yl)-5-(5-fluorobenzo[d]oxazol-2-yl)isonicotinate 14d (200 mg, 0.456 mmol) was dissolved in 9 mL of a mixed solvent of tetrahydrofuran and water (V:V=2:1), and added with sodium hydroxide (183 mg, 4.56 mmol), and reacted at room temperature overnight. After the completion of the reaction, the reaction solution was adjusted with 2N trifluoroacetic acid aqueous solution to pH=2-3, and extracted with ethyl acetate (50 mL). The organic phase was dried over anhydrous sodium sulfate, filtered, and concentrated under reduced pressure. The resulting residue was separated and purified with a preparative column, to obtain 2-(7-fluoro-3,4-dihydrobenzo[b][1,4]oxazepine-5(2H)-yl)-5-(5-fluorobenzo[d]oxazol-2-yl)isonicotinic acid 14 (125 mg), with a yield of 65%.

MS m/z (ESI): 423.9 [M+1]

$^1$H NMR (400 MHz, Methanol-$d_4$) δ 8.80 (s, 1H), 7.61 (dd, J=9.0, 4.2 Hz, 1H), 7.44 (dd, J=8.4, 2.4 Hz, 1H), 7.25-7.08 (m, 4H), 6.87 (s, 1H), 4.11 (br, 4H), 2.13-2.10 (m, 2H).

Example 15

2-(7-fluoro-3,4-dihydrobenzo[b][1,4]oxazepine-5(2H)-yl)-5-(6-fluorobenzo[d]oxazol-2-yl)isonicotinic acid

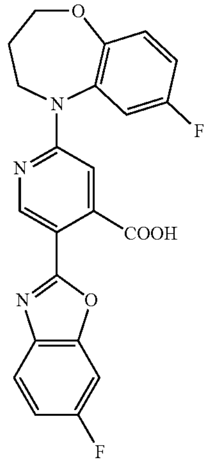

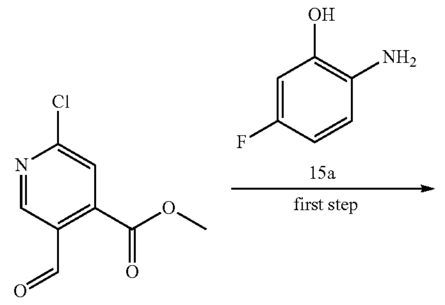

12c

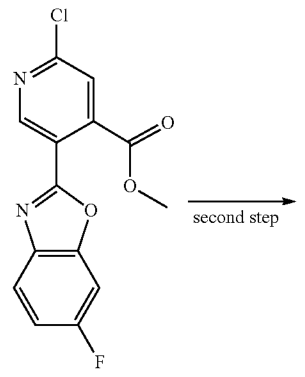

15b

-continued

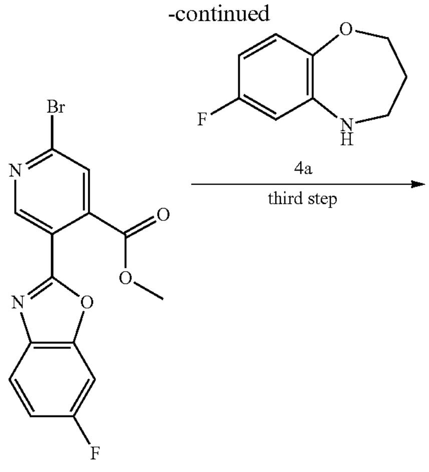

15c

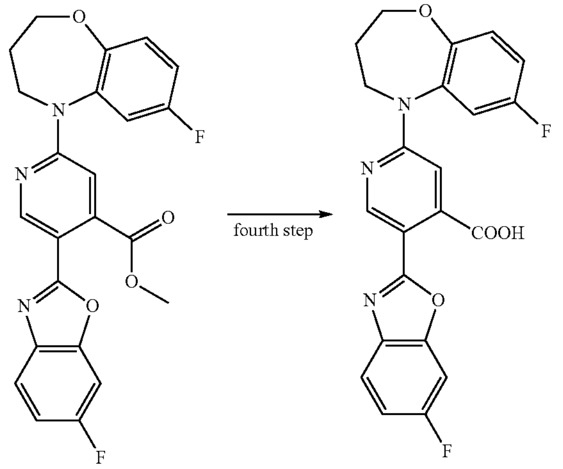

15d

15

First Step

Methyl 2-chloro-5-(6-fluorobenzo[d]oxazol-2-yl)isonicotinate

Methyl 2-chloro-5-formylisonicotinate 12c (200 mg, 1.0 mmol), and 2-amino-5-fluorophenol 15a (127 mg, 1.0 mmol) were dissolved in 3 mL of methanol, and reacted at 85° C. overnight. After the completion of the reaction, the reaction solution was cooled down to room temperature, and concentrated under reduced pressure. The resulting residue was dissolved in 3 mL of dichloromethane, and added with 2,3-dichloro-5,6-dicyano-1,4-benzoquinone (227 mg, 1.0 mmol), and reacted at 35-40° C. for 1 day. After the completion of the reaction, the reaction solution was concentrated under reduced pressure. The resulting residue was purified with silica gel column chromatography (mobile phase: system A), to obtain methyl 2-chloro-5-(6-fluorobenzo[d]oxazol-2-yl)isonicotinate 15b (190 mg), with a yield of 62%.

MS m/z (ESI): 307.0 [M+1]

Second Step

Methyl 2-bromo-5-(6-fluorobenzo[d]oxazol-2-yl)isonicotinate

Methyl 2-chloro-5-(6-fluorobenzo[d]oxazol-2-yl)isonicotinate 15b (190 mg, 0.619 mmol) was dissolved in 50 mL of acetonitrile, added with trimethylsilyl bromide (678 mg, 4.43 mmol), and refluxed at 100° C. to perform reaction overnight. After the completion of the reaction, the reaction solution was cooled down to room temperature, and concentrated under reduced pressure. To the residue, 30 mL of ethyl acetate and 15 mL of water were added, and saturated sodium bicarbonate solution was added dropwise, to adjust the solution to pH=8, and extracted with ethyl acetate (30 mL×2). The organic phases were combined, dried over anhydrous sodium sulfate, filtered, and concentrated under reduced pressure. The resulting residue was purified with silica gel column chromatography (mobile phase: system A), to obtain methyl 2-bromo-5-(6-fluorobenzo[d]oxazol-2-yl) isonicotinate 15c (70 mg), with a yield of 32%.

MS m/z (ESI): 351.0 [M+1]

Third Step

Methyl 2-(7-fluoro-3,4-dihydrobenzo[b][1,4] oxazepine-5(2H)-yl)-5-(6-fluorobenzo[d]oxazol-2-yl)isonicotinate Under argon gas atmosphere, methyl 2-bromo-5-(6-fluorobenzo[d]oxazol-2-yl)isonicotinate 15c (70 mg, 0.20 mmol), 7-fluoro-2,3,4,5-tetrahydrobenzo[b][1,4]oxazepine 4a (40 mg, 0.24 mmol, prepared according to the disclosure of patent WO 2016142867A1), tris(dibenzylideneacetone) dipalladium (17 mg, 0.020 mmol), 4,5-bis(diphenylphosphino)-9,9-dimethylxanthene (Xantphos, 10 mg, 0.02 mmol) and cesium carbonate (195 mg, 0.60 mmol) were dissolved in 3 mL of toluene, and reacted at 90° C. for 7 hours. After the completion of the reaction, the mixture was cooled down to room temperature, and added with 30 mL of water and 50 mL of ethyl acetate. After liquid separation, the aqueous phase was extracted with ethyl acetate (50 mL). The organic phases were combined, washed with 20 mL of water, dried over anhydrous sodium sulfate, filtered, and concentrated under reduced pressure. The resulting residue was purified with silica gel column chromatography (mobile phase: system A), to obtain methyl 2-(7-fluoro-3,4-dihydrobenzo[b][1,4]oxazepine-5(2H)-yl)-5-(6-fluorobenzo[d] oxazol-2-yl)isonicotinate 15d (10 mg), with a yield of 11%.

MS m/z (ESI): 437.9 [M+1]

$^1$H NMR (400 MHz, CDC13) δ 8.88 (s, 1H), 7.58-7.55 (m, 1H), 7.20-7.17 (m 1H), 7.08-6.89 (m, 4H), 6.59 (s, 1H), 4.02 (br, 4H), 3.79 (s, 3H), 2.03 (br, 2H).

Fourth Step 2-(7-fluoro-3,4-dihydrobenzo[b][1,4]oxazepine-5 (2H)-yl)-5-(6-fluorobenzo[d]oxazol-2-yl)isonicotinic acid Methyl 2-(7-fluoro-3,4-dihydrobenzo[b][1,4]oxazepine-5 (2H)-yl)-5-(6-fluorobenzo[d]oxazol-2-yl)isonicotinate 15d (10 mg, 0.022 mmol) and sodium hydroxide (10 mg, 0.25 mmol) were dissolved in 3 mL of a mixed solvent of tetrahydrofuran and water (V:V=2:1), and reacted at room temperature overnight. After the completion of the reaction, the reaction solution was adjusted with 2N dilute hydrochloric acid to pH=2-3, and extracted with ethyl acetate (10 mL). The organic phase was dried over anhydrous sodium sulfate, filtered, and concentrated under reduced pressure. The resulting residue was separated and purified with a preparative column, to obtain 2-(7-fluoro-3,4-dihydrobenzo[b][1,4]oxazepine-5(2H)-yl)-5-(6-fluorobenzo[d]oxazol-2-yl)isonicotinic acid 15 (1.5 mg), with a yield of 15%.

MS m/z (ESI): 423.9 [M+1]

$^1$H NMR (400 MHz, $CDCl_3$) δ 9.20 (s, 1H), 7.69-7.64 (m, 2H), 7.39 (dd, J=7.8, 2.2 Hz, 1H), 7.21-7.13 (m, 2H), 7.04-6.98- (m, 2H), 4.11 (br, 4H), 2.13 (br, 2H).

Example 16

5-(6-cyanobenzo[d]oxazol-2-yl)-2-(7-fluoro-3,4-dihydrobenzo[b][1,4]oxazepine-5(2H)-yl)isonicotinic acid

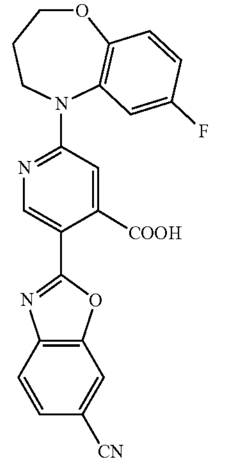

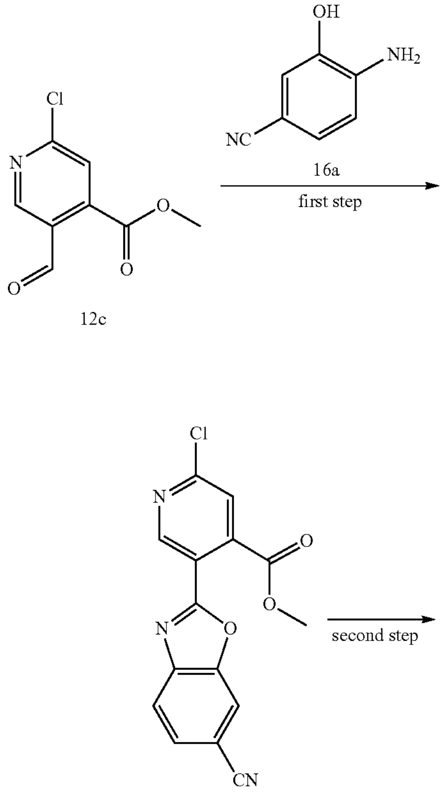

16a

12c

16b

-continued

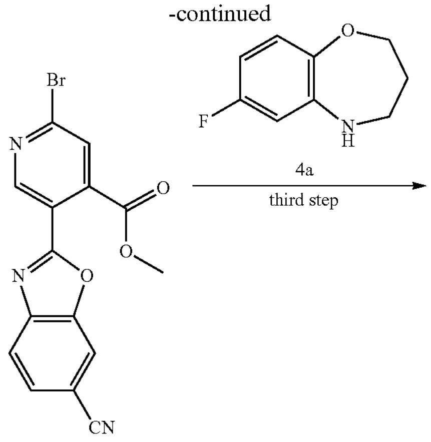

16c

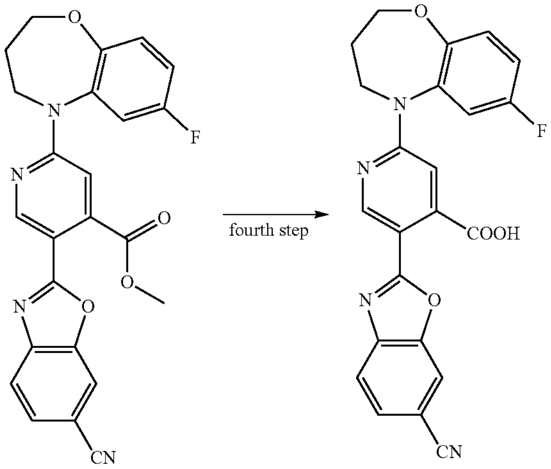

16d 16

First Step

Methyl 2-chloro-5-(6-cyanobenzo[d]oxazol-2-yl) isonicotinate

Methyl 2-chloro-5-formylisonicotinate 12c (200 mg, 1.0 mmol), and 4-amino-3-hydroxybenzonitrile 16a (134 mg, 1.0 mmol) were dissolved in 15 mL of methanol, and reacted at 85° C. overnight. The reaction solution was cooled down to room temperature, and concentrated under reduced pressure. The resulting residue was dissolved in 10 mL of dichloromethane, and added with 2,3-dichloro-5,6-dicyano-1,4-benzoquinone (227 mg, 1.0 mmol), and reacted at 35-40° C. for 1 day. After the completion of the reaction, the reaction solution was concentrated under reduced pressure. The resulting residue was purified with silica gel column chromatography (mobile phase: system A), to obtain methyl 2-chloro-5-(6-cyanobenzo[d]oxazol-2-yl)isonicotinate 16b (190 mg), with a yield of 61%.

MS m/z (ESI): 313.9 [M+1]

Second Step

Methyl 2-bromo-5-(6-cyanobenzo[d]oxazol-2-yl) isonicotinate

Methyl 2-chloro-5-(6-cyanobenzo[d]oxazol-2-yl)isonicotinate 16b (90 mg, 0.287 mmol) was dissolved in 10 mL of acetonitrile, and added with trimethylsilyl bromide (314 mg, 2.05 mmol), and reacted at 70-80° C. overnight. After the completion of the reaction, the reaction solution was cooled down to room temperature, concentrated under reduced pressure, to obtain a crude product methyl 2-bromo-5-(6-cyanobenzo[d]oxazol-2-yl)isonicotinate 16c (120 mg), which was used directly in the next step.

MS m/z (ESI): 359.8 [M+1]

Third Step

Methyl 5-(6-cyanobenzo[d]oxazol-2-yl)-2-(7-fluoro-3,4-dihydrobenzo[b][1,4]oxazepine-5(2H)-yl)isonicotinate Under nitrogen gas atmosphere, methyl 2-bromo-5-(6-cyanobenzo[d]oxazol-2-yl)isonicotinate 16c (120 mg, 0.335 mmol), 7-fluoro-2,3,4,5-tetrahydrobenzo[b][1,4]oxazepine 4a (68 mg, 0.402 mmol, prepared according to the disclosure of patent WO 2016142867A1), tris(dibenzylideneacetone) dipalladium (28 mg, 0.0335 mmol), 4,5-bis(diphenylphosphino)-9,9-dimethylxanthene (Xantphos, 16 mg, 0.0335 mmol) and cesium carbonate (328 mg, 1.005 mmol) were dissolved in 3 mL of toluene, and reacted at 95° C. overnight. After the completion of the reaction, the mixture was cooled down to room temperature, and added with 15 mL of water and 30 mL of ethyl acetate. After liquid separation, the aqueous phase was extracted with ethyl acetate (30 mL). The organic phases were combined, and washed with 20 mL of water, dried over anhydrous sodium sulfate, filtered, and concentrated under reduced pressure. The resulting residue was purified with silica gel column chromatography (mobile phase: system A), to obtain methyl 5-(6-cyanobenzo[d]oxazol-2-yl)-2-(7-fluoro-3,4-dihydrobenzo[b][1,4]oxazepine-5(2H)-yl)isonicotinate 16d (10 mg), with a yield of 6.7%.

MS m/z (ESI): 444.9 [M+1]

$^1$H NMR (400 MHz, CDCl3) δ 9.01 (s, 1H), 7.84 (m, 1H), 7.77 (d, J=8.4 Hz, 1H), 7.63 (dd, J=8.2, 1.4 Hz, 1H), 7.17-7.12 (m, 1H), 7.05-6.97 (m, 2H), 6.65 (s, 1H), 4.15-4.05 (m, 4H), 3.89 (s, 3H), 2.12 (br, 2H).

Fourth Step 5-(6-cyanobenzo[d]oxazol-2-yl)-2-(7-fluoro-3,4-dihydrobenzo[b][1,4]oxazepine-5(2H)-yl)isonicotinic acid Methyl 5-(6-cyanobenzo[d]oxazol-2-yl)-2-(7-fluoro-3,4-dihydrobenzo[b][1,4]oxazepine-5(2H)-yl)isonicotinate 16d (10 mg, 0.022 mmol) was dissolved in 3 mL of a mixed solvent of tetrahydrofuran and water (V:V=2:1), added with sodium hydroxide (20 mg, 0.5 mmol), and stirred at room temperature overnight. After the completion of the reaction, the reaction solution was adjusted with 2N dilute hydrochloric acid to pH=1-2, and extracted with ethyl acetate (5 mL×2). The organic phases were combined, dried over anhydrous sodium sulfate, filtered, and concentrated under reduced pressure. The resulting residue was separated and purified with a preparative column, to obtain 5-(6-cyano-benzo[d]oxazol-2-yl)-2-(7-fluoro-3,4-dihydrobenzo[b][1,4]oxazepine-5(2H)-yl)isonicotinic acid 16 (5 mg), with a yield of 53%.

MS m/z (ESI): 431.0 [M+1]

Example 17

5-(4-chlorobenzo[d]oxazol-2-yl)-2-(7-fluoro-3,4-dihydrobenzo[b][1,4]oxazepine-5(2H)-yl)isonicotinic acid

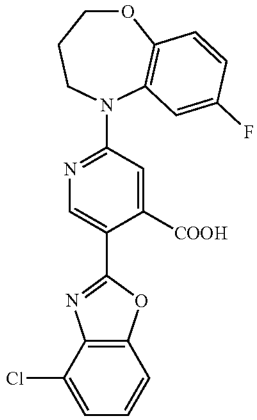

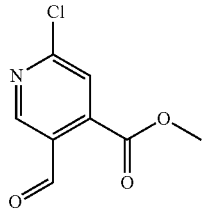

12c

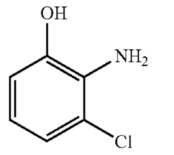

17a

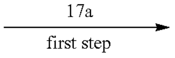

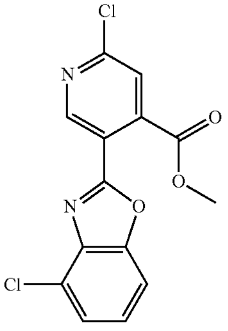

17b

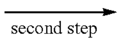

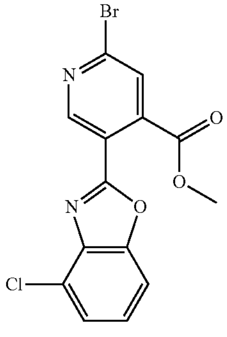

17c

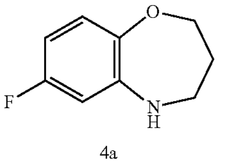

4a

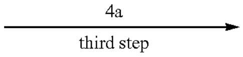

-continued

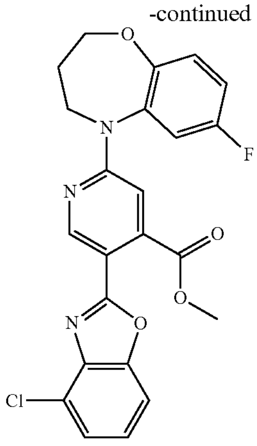

17d

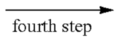

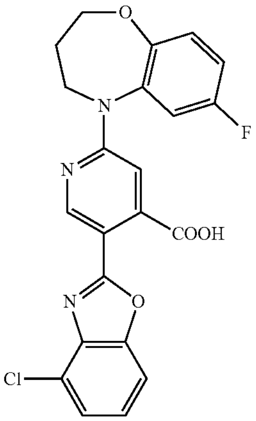

17

First Step

Methyl 2-chloro-5-(4-chlorobenzo[d]oxazol-2-yl) isonicotinate

Methyl 2-chloro-5-formylisonicotinate 12c (300 mg, 1.5 mmol), and 2-amino-3-chlorophenol 17a (237 mg, 1.65 mmol) were dissolved in 20 mL of methanol, and reacted at 85° C. for 20 hours. The reaction solution was cooled down to room temperature, and concentrated under reduced pressure. The resulting residue was dissolved in 20 mL of dichloromethane, and added with 2,3-dichloro-5,6-dicyano-1,4-benzoquinone (375 mg, 1.65 mmol), and reacted at 48° C. for 20 hours. After the completion of the reaction, the reaction solution was concentrated under reduced pressure. The resulting residue was purified with silica gel column chromatography (mobile phase: system A), to obtain methyl 2-chloro-5-(4-chlorobenzo[d]oxazol-2-yl)isonicotinate 17b (250 mg), with a yield of 52%.

MS m/z (ESI): 322.6[M+1]

Second Step

Methyl 2-bromo-5-(4-chlorobenzo[d]oxazol-2-yl) isonicotinate

Methyl 2-chloro-5-(4-chlorobenzo[d]oxazol-2-yl)isonicotinate 17b (250 mg, 0.78 mmol) was dissolved in 10 mL of acetonitrile, and added with trimethylsilyl bromide (1 mL, 5.46 mmol), and reacted at 80-85° C. overnight. After the completion of the reaction, the reaction solution was cooled down to room temperature, and concentrated under reduced pressure. To the resulting residue, 20 mL of ethyl acetate and 15 mL of water were added. The solution was added with saturated sodium bicarbonate solution dropwise to adjust it to pH=8, and extracted with ethyl acetate (30 mL×2). The organic phases were combined, dried over anhydrous sodium sulfate, filtered, and concentrated under reduced pressure. The resulting residue was purified with silica gel column chromatography (mobile phase: system A), to obtain methyl 2-bromo-5-(4-chlorobenzo[d]oxazol-2-yl)isonicotinate 17c (280 mg), with a yield of 98%.

MS m/z (ESI): 366.9 [M+1]

Third Step methyl 5-(4-chlorobenzo[d]oxazol-2-yl)-2-(7-fluoro-3,4-dihydrobenzo[b][1,4]oxazepine-5(2H)-yl)isonicotinate Under argon gas atmosphere, methyl 2-bromo-5-(4-chlorobenzo[d]oxazol-2-yl)isonicotinate 17c (280 mg, 0.76 mmol), 7-fluoro-2,3,4,5-tetrahydrobenzo[b][1,4]oxazepine 4a (153 mg, 0.92 mmol, prepared according to the disclosure of patent WO 2016142867A1), tris(dibenzylideneacetone) dipalladium (70 mg, 0.076 mmol), 4,5-bis(diphenylphosphino)-9,9-dimethylxanthene (Xantphos, 88 mg, 0.152 mmol) and cesium carbonate (498 mg, 1.53 mmol) were dissolved in 20 mL of toluene, and reacted at 95° C. overnight. After the completion of the reaction, the mixture was cooled down to room temperature, and added with 10 mL of water, and extracted with ethyl acetate (20 mL×2). The organic phases were combined, the organic phase was washed with 20 mL of saturated sodium chloride solution, dried over anhydrous sodium sulfate, filtered, and concentrated under reduced pressure. The resulting residue was purified with silica gel column chromatography (mobile phase: system A), to obtain methyl 5-(4-chlorobenzo[d]oxazol-2-yl)-2-(7-fluoro-3,4-dihydrobenzo[b][1,4]oxazepine-5(2H)-yl)isonicotinate 17d (80 mg), with a yield of 23%.

MS m/z (ESI): 453.9 [M+1]

Fourth Step 5-(4-chlorobenzo[d]oxazol-2-yl)-2-(7-fluoro-3,4-dihydrobenzo[b][1,4]oxazepine-5(2H)-yl)isonicotinic acid Methyl 5-(4-chlorobenzo[d]oxazol-2-yl)-2-(7-fluoro-3,4-dihydrobenzo[b][1,4]oxazepine-5(2H)-yl)isonicotinate 17d (80 mg, 0.176 mmol) was dissolved in 8 mL of a mixed solvent of tetrahydrofuran and water (V:V-5:3), added with sodium hydroxide (40 mg, 1.0 mmol), and stirred at room temperature overnight. After the completion of the reaction, the reaction solution was added with 2N dilute hydrochloric acid to adjust it to acidity, then added with 10 mL of water, and extracted with ethyl acetate (10 mL). The resulting organic phase was dried over anhydrous sodium sulfate, filtered, and concentrated under reduced pressure. The resulting residue was separated and purified with a preparative column, to obtain 5-(4-chlorobenzo[d]oxazol-2-yl)-2-(7-fluoro-3,4-dihydrobenzo[b][1,4]oxazepine-5(2H)-yl)isonicotinic acid 17 (16.3 mg), with a yield of 21.1%.

MS m/z (ESI): 439.9 [M+1]

$^1$H NMR (400 MHz, $CDCl_3$) δ 9.22 (s, 1H), 7.64 (s, 1H), 7.56 (d, J=8.4 Hz, 1H), 7.45-7.38 (m, 2H), 7.17-7.13 (m, 1H), 7.05-6.98 (m, 2H), 4.11 (br, 4H), 2.14 (br, 2H).

Example 18

5-(5-chlorobenzo[d]oxazol-2-yl)-2-(7-fluoro-3,4-dihydrobenzo[b][1,4]oxazepine-5(2H)-yl)isonicotinic acid

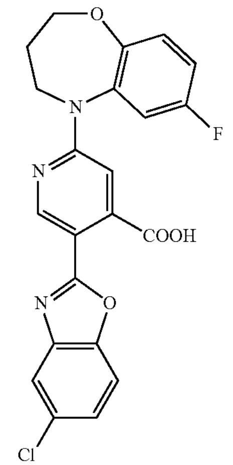

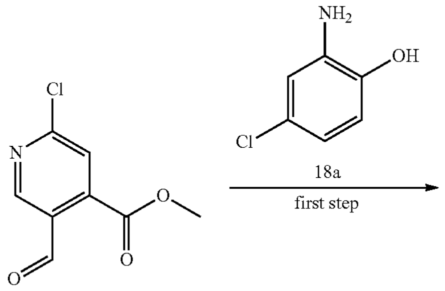

12c

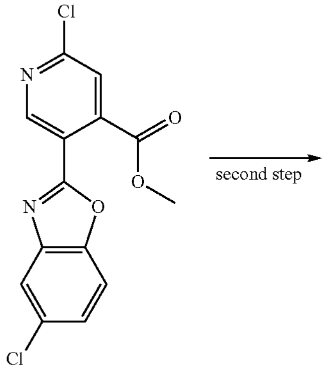

18b

-continued

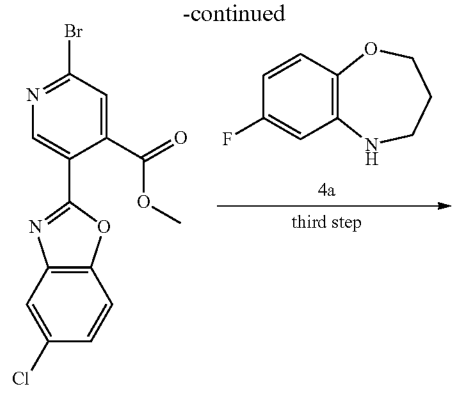

18c

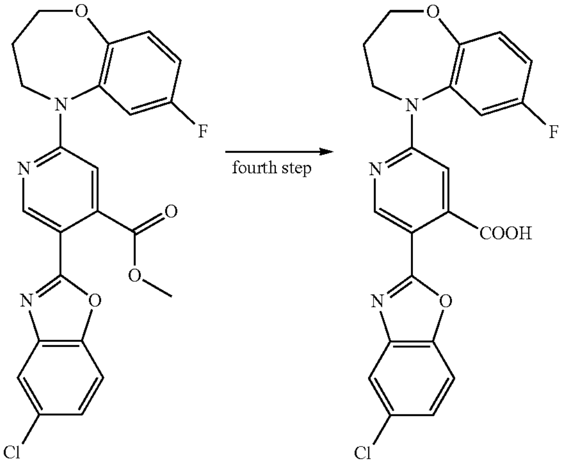

18d

18

First Step

Methyl 2-chloro-5-(5-chlorobenzo[d]oxazol-2-yl) isonicotinate

Methyl 2-chloro-5-formylisonicotinate 12c (600 mg, 3.02 mmol), and 2-amino-4-chlorophenol 18a (478 mg, 3.32 mmol) were dissolved in 15 mL of methanol, and reacted at 90° C. overnight. The reaction solution was cooled down to room temperature, and concentrated under reduced pressure. The resulting residue was dissolved in 15 mL of dichloromethane, and added with 2,3-dichloro-5,6-dicyano-1,4-benzoquinone (754 mg, 3.32 mmol), and reacted at 45° C. overnight. After the completion of the reaction, the reaction solution was concentrated under reduced pressure. The resulting residue was purified with silica gel column chromatography (mobile phase: system A), to obtain methyl 2-chloro-5-(5-chlorobenzo[d]oxazol-2-yl)isonicotinate 18b (350 mg), with a yield of 36%.

MS m/z (ESI): 323.0 [M+1]

Second Step

Methyl 2-bromo-5-(5-chlorobenzo[d]oxazol-2-yl) isonicotinate

Methyl 2-chloro-5-(5-chlorobenzo[d]oxazol-2-yl)isonicotinate 18b (350 mg, 1.08 mmol) was dissolved in 15 mL of acetonitrile, and added with trimethylsilyl bromide (1.02 mL, 7.73 mmol), and reacted at 80° C. overnight. After the completion of the reaction, the reaction solution was cooled down to room temperature, and concentrated under reduced pressure. To the residue, 20 mL of ethyl acetate and 250 mL of saturated sodium bicarbonate solution were added, resulting a solution with pH=9-10. The collected organic phase was dried over anhydrous sodium sulfate, filtered, and concentrated under reduced pressure. The resulting residue was purified with silica gel column chromatography (mobile phase: system A), to obtain methyl 2-bromo-5-(5-chlorobenzo[d]oxazol-2-yl)isonicotinate 18c (350 mg), with a yield of 95%.

MS m/z (ESI): 366.8 [M+1]

Third Step

Methyl 5-(5-chlorobenzo[d]oxazol-2-yl)-2-(7-fluoro-3,4-dihydrobenzo[b][1,4]oxazepine-5(2H)-yl) isonicotinate Under nitrogen gas atmosphere, methyl 2-bromo-5-(5-chlorobenzo[d]oxazol-2-yl)isonicotinate 18c (350 mg, 0.95 mmol), 7-fluoro-2,3,4,5-tetrahydrobenzo[b][1,4]oxazepine 4a (160 mg, 0.95 mmol, prepared according to the disclosure of patent WO 2016142867A1), tris(dibenzylideneacetone) dipalladium (87 mg, 0.095 mmol), 4,5-bis(diphenylphosphino)-9,9-dimethylxanthene (Xantphos, 110 mg, 0.19 mmol) and cesium carbonate (619 mg, 1.9 mmol) were dissolved in 20 mL of toluene, and reacted at 95° C. overnight. After the completion of the reaction, the mixture was cooled down to room temperature, added with 200 mL of water, and extracted with ethyl acetate (200 mL×2). The organic phases were combined, washed with 100 mL of saturated sodium chloride solution, dried over anhydrous sodium sulfate, filtered, and concentrated under reduced pressure. The resulting residue was purified with silica gel column chromatography (mobile phase: system A), to obtain methyl 5-(5-chlorobenzo[d]oxazol-2-yl)-2-(7-fluoro-3,4-dihydrobenzo[b][1,4]oxazepine-5(2H)-yl)isonicotinate 18d (80 mg), with a yield of 19%.

MS m/z (ESI): 454.0 [M+1]

Fourth Step 5-(5-chlorobenzo[d]oxazol-2-yl)-2-(7-fluoro-3,4-dihydrobenzo[b][1,4]oxazepine-5(2H)-yl)isonicotinic acid Methyl 5-(5-chlorobenzo[d]oxazol-2-yl)-2-(7-fluoro-3,4-dihydrobenzo[b][1,4]oxazepine-5(2H)-yl)isonicotinate 18d (80 mg, 0.176 mmol) was dissolved in 10 mL of a mixed solvent of tetrahydrofuran and water (V:V=1:1), added with potassium hydroxide (98.6 mg, 1.76 mmol), and stirred at room temperature overnight. After the completion of the reaction, the reaction solution was added with 100 mL of ethyl acetate and 100 mL of water, and adjusted with 2N dilute hydrochloric acid to a potential of hydrogen of pH=3. After liquid separation, the aqueous phase was extracted with ethyl acetate (100 mL×2), the organic phases were combined, dried over anhydrous sodium sulfate, filtered, and concentrated under reduced pressure. The resulting residue was separated and purified with a preparative column, to obtain 5-(5-chlorobenzo[d]oxazol-2-yl)-2-(7-fluoro-3,4-dihydrobenzo[b][1,4]oxazepine-5(2H)-yl)isonicotinic acid 18 (10 mg), with a yield of 14%.

MS m/z (ESI): 440.1 [M+1]

$^1$H NMR (400 MHz, DMSO-d6) δ 9.20 (s, 1H), 7.72 (s, 1H), 7.60-7.55 (m, 2H), 7.42-7.39 (m, 1H), 7.16-7.13 (m, 1H), 7.04-6.98 (m, 2H), 4.26 (br, 2H), 4.11 (br, 2H), 2.13 (br, 2H).

Example 19

5-(6-chlorobenzo[d]oxazol-2-yl)-2-(7-fluoro-3,4-dihydrobenzo[b][1,4]oxazepine-5(2H)-yl)isonicotinic acid

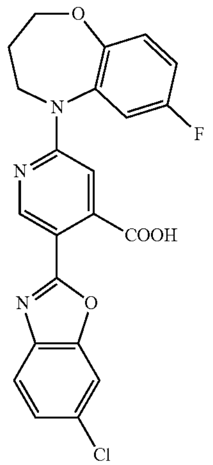

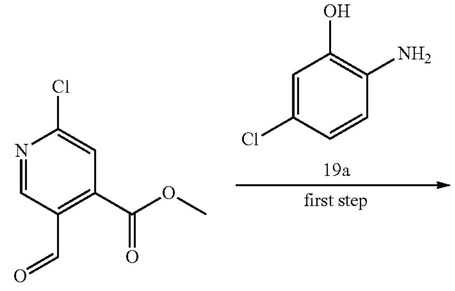

12c

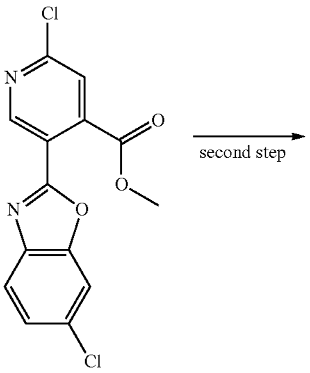

19b

-continued

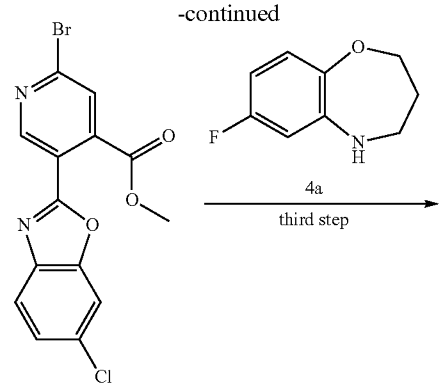

19c

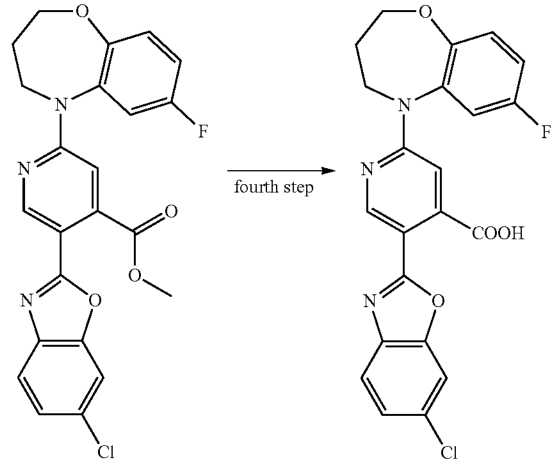

19d 19

First Step

Methyl 2-chloro-5-(6-chlorobenzo[d]oxazol-2-yl) isonicotinate

Methyl 2-chloro-5-formylisonicotinate 12c (300 mg, 1.5 mmol), and 2-amino-5-chlorophenol 19a (237 mg, 1.65 mmol) were dissolved in 15 mL of methanol, and refluxed at 80-85° C. to perform reaction overnight. The reaction solution was cooled down to room temperature, and concentrated under reduced pressure. The resulting residue was dissolved in 20 mL of dichloromethane, and added with 2,3-dichloro-5,6-dicyano-1,4-benzoquinone (375 mg, 1.65 mmol), and reacted at 48° C. overnight. After the completion of the reaction, the reaction solution was concentrated under reduced pressure. The resulting residue was purified with silica gel column chromatography (mobile phase: system A), to obtain methyl 2-chloro-5-(6-chlorobenzo[d]oxazol-2-yl) isonicotinate 19b (195 mg), with a yield of 40%.

MS m/z (ESI): 322.9 [M+1]

Second Step

Methyl 2-bromo-5-(6-chlorobenzo[d]oxazol-2-yl) isonicotinate

Methyl 2-chloro-5-(6-chlorobenzo[d]oxazol-2-yl)isonicotinate 19b (195 mg, 0.61 mmol) was dissolved in 10 mL of acetonitrile, added with trimethylsilyl bromide (1.1 mL, 8.54 mmol), and reacted at 85° C. for 6 hours. After the completion of the reaction, the reaction solution was cooled down to room temperature, and concentrated under reduced pressure. To the residue, 50 mL of ethyl acetate and 25 mL of water were added. The solution was adjusted to pH=8 by adding with saturated sodium bicarbonate solution dropwise. After liquid separation, the aqueous phase was extracted with ethyl acetate (30 mL). The organic phases were combined, dried over anhydrous sodium sulfate, filtered, and concentrated under reduced pressure. The resulting residue was purified with silica gel column chromatography (mobile phase: system A), to obtain methyl 2-bromo-5-(6-chlorobenzo[d]oxazol-2-yl)isonicotinate 19c (169 mg), with a yield of 76%.

MS m/z (ESI): 366.8 [M+1]

Third Step

Methyl 5-(6-chlorobenzo[d]oxazol-2-yl)-2-(7-fluoro-3,4-dihydrobenzo[b][1,4]oxazepine-5(2H)-yl) isonicotinate Under nitrogen gas atmosphere, methyl 2-bromo-5-(6-chlorobenzo[d]oxazol-2-yl)isonicotinate 19c (169 mg, 0.46 mmol), 7-fluoro-2,3,4,5-tetrahydrobenzo[b][1,4]oxazepine 4a (92 mg, 0.552 mmol, prepared according to the disclosure of patent WO 2016142867A1), tris(dibenzylideneacetone) dipalladium (42 mg, 0.046 mmol), 4,5-bis(diphenylphosphino)-9,9-dimethylxanthene (Xantphos, 53 mg, 0.092 mmol) and cesium carbonate (300 mg, 0.92 mmol) were dissolved in 6 mL of toluene, and reacted at 95° C. overnight. After the completion of the reaction, the mixture was cooled down to room temperature, added with 10 mL of water, and extracted with ethyl acetate (20 mL×2). The organic phases were combined, washed with 10 mL of saturated sodium chloride solution, dried over anhydrous sodium sulfate, filtered, and concentrated under reduced pressure. The resulting residue was purified with silica gel column chromatography (mobile phase: system A), to obtain methyl 5-(6-chlorobenzo[d]oxazol-2-yl)-2-(7-fluoro-3,4-dihydrobenzo[b][1,4]oxazepine-5(2H)-yl)isonicotinate 19d (100 mg), with a yield of 48%.

MS m/z (ESI): 453.9 [M+1]

Fourth Step 5-(6-chlorobenzo[d]oxazol-2-yl)-2-(7-fluoro-3,4-dihydrobenzo[b][1,4]oxazepine-5(2H)-yl)isonicotinic acid Methyl 5-(6-chlorobenzo[d]oxazol-2-yl)-2-(7-fluoro-3,4-dihydrobenzo[b][1,4]oxazepine-5(2H)-yl)isonicotinate 19d (100 mg, 0.22 mmol) was dissolved in 5 mL of tetrahydrofuran, added with 3 mL of water, then added with sodium hydroxide (40 mg, 1.0 mmol), and stirred at room temperature overnight. After the completion of the reaction, the reaction solution was added with 2N dilute hydrochloric acid to adjust it to acidity, then added with 10 mL of water, and extracted with ethyl acetate (20 mL). The resulting organic phase was dried over anhydrous sodium sulfate, filtered, and concentrated under reduced pressure. The resulting residue was separated and purified with a preparative column, to obtain 5-(6-chlorobenzo[d]oxazol-2-yl)-2-(7-fluoro-3,4-dihydrobenzo[b][1,4]oxazepine-5(2H)-yl) isonicotinic acid 19 (10.27 mg), with a yield of 10.6%.

MS m/z (ESI): 439.9 [M+1]

$^1$H NMR (400 MHz, $CDCl_3$) δ 9.20 (s, 1H), 7.67-7.63 (m, 3H), 7.42 (d, J=8.4 Hz, 1H), 7.16-7.13 (m, 1H), 7.04-6.98 (m, 2H), 4.11 (br, 4H), 2.14 (br, 2H).

Example 20

5-(7-chlorobenzo[d]oxazol-2-yl)-2-(7-fluoro-3,4-dihydrobenzo[b][1,4]oxazepine-5(2H)-yl)isonicotinic acid

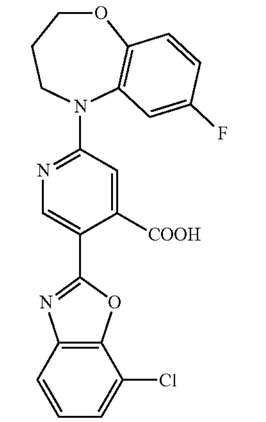

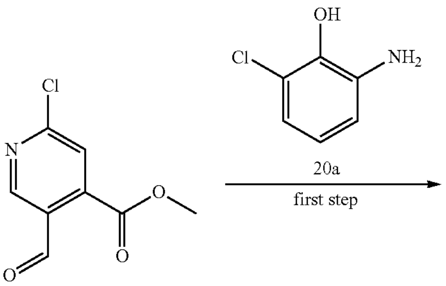

12c

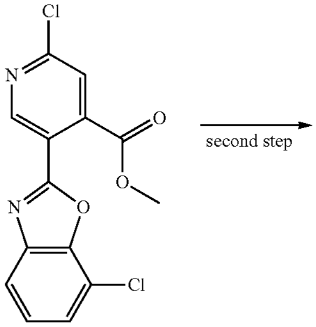

20b

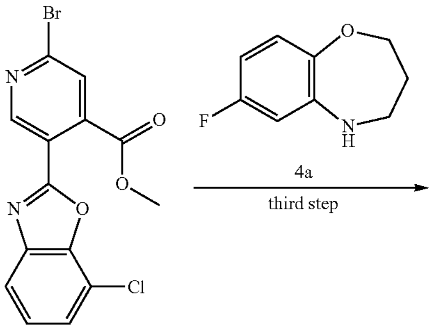

20c

-continued

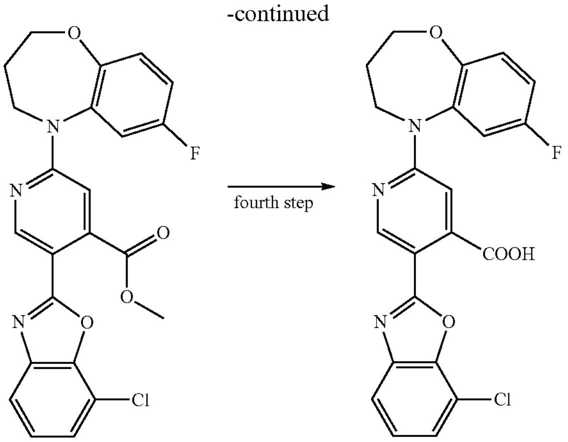

20d

20

First Step

Methyl 2-chloro-5-(7-chlorobenzo[d]oxazol-2-yl) isonicotinate

Methyl 2-chloro-5-formylisonicotinate 12c (300 mg, 1.5 mmol), and 2-amino-6-chlorophenol 20a (237 mg, 1.65 mmol) were dissolved in 15 mL of methanol, and refluxed at 80-85° C. to perform reaction overnight. The reaction solution was cooled down to room temperature, and concentrated under reduced pressure. The resulting residue was dissolved in 20 mL of dichloromethane, and then added with 2,3-dichloro-5,6-dicyano-1,4-benzoquinone (375 mg, 1.65 mmol), and reacted at 48° C. overnight. After the completion of the reaction, the reaction solution was concentrated under reduced pressure. The resulting residue was purified with silica gel column chromatography (mobile phase: system A), to obtain methyl 2-chloro-5-(7-chlorobenzo[d]oxazol-2-yl) isonicotinate 20b (110 mg), with a yield of 23%.

MS m/z (ESI): 322.6[M+1]

Second Step

Methyl 2-bromo-5-(7-chlorobenzo[d]oxazol-2-yl) isonicotinate

Methyl 2-chloro-5-(7-chlorobenzo[d]oxazol-2-yl)isonicotinate 20b (110 mg, 0.34 mmol) was dissolved in 10 mL of acetonitrile, added with trimethylsilyl bromide (0.9 mL), and reacted at 85° C. for 6 hours. After the completion of the reaction, the reaction solution was cooled down to room temperature, and concentrated under reduced pressure. To the residue, 50 mL of ethyl acetate and 25 mL of water was added. The solution was adjusted to pH=8 by adding with saturated sodium bicarbonate solution. After liquid separation, the aqueous phase was extracted with ethyl acetate (30 mL). The organic phases were combined, dried over anhydrous sodium sulfate, filtered, and concentrated under reduced pressure. The resulting residue was purified with silica gel column chromatography (mobile phase: system A), to obtain methyl 2-bromo-5-(7-chlorobenzo[d]oxazol-2-yl) isonicotinate 20c (123 mg), with a yield of 99%.

MS m/z (ESI): 366.8[M+1]

Third Step

Methyl 5-(7-chlorobenzo[d]oxazol-2-yl)-2-(7-fluoro-3,4-dihydrobenzo[b][1,4]oxazepine-5(2H)-yl) isonicotinate Under argon gas atmosphere, methyl 2-bromo-5-(7-chlorobenzo[d]oxazol-2-yl)isonicotinate 20c (123 mg, 0.335 mmol), 7-fluoro-2,3,4,5-tetrahydrobenzo[b][1,4]oxazepine 4a (67 mg, 0.401 mmol, prepared according to the disclosure of patent WO 2016142867A1), tris(dibenzylideneacetone) dipalladium (31 mg, 0.0335 mmol), 4,5-bis(diphenylphosphino)-9,9-dimethylxanthene (Xantphos, 39 mg, 0.067 mmol) and cesium carbonate (218 mg, 0.67 mmol) were dissolved in 5 mL of toluene, and reacted at 95° C. overnight. After the completion of the reaction, the mixture was cooled down to room temperature, added with 10 mL of water and 20 mL of ethyl acetate, and extracted with ethyl acetate (20 mL×2). The organic phases were combined. The resulting organic phase was washed with 10 mL of saturated sodium chloride solution, dried over anhydrous sodium sulfate, filtered, and concentrated under reduced pressure. The resulting residue was purified with silica gel column chromatography (mobile phase: system A), to obtain methyl 5-(7-chlorobenzo[d]oxazol-2-yl)-2-(7-fluoro-3,4-dihydrobenzo[b][1,4]oxazepine-5(2H)-yl) isonicotinate 20d (50 mg), with a yield of 33%.

MS m/z (ESI): 454.0 [M+1]

Fourth Step 5-(7-chlorobenzo[d]oxazol-2-yl)-2-(7-fluoro-3,4-dihydrobenzo[b][1,4]oxazepine-5(2H)-yl)isonicotinic acid Methyl 5-(7-chlorobenzo[d]oxazol-2-yl)-2-(7-fluoro-3,4-dihydrobenzo[b][1,4]oxazepine-5(2H)-yl) isonicotinate 20d (50 mg, 0.11 mmol) was dissolved in 8 mL of a mixed solvent of tetrahydrofuran and water (V:V=5:3), added with sodium hydroxide (25 mg, 0.625 mmol), and stirred at room temperature overnight. After the completion of the reaction, the reaction solution was added with 2N dilute hydrochloric acid to adjust it to acidity, added with 10 mL of water, and extracted with ethyl acetate (20 mL). The resulting organic phase was dried over anhydrous sodium sulfate, filtered, and concentrated under reduced pressure. The resulting residue was separated and purified with a preparative column, to obtain 5-(7-chlorobenzo[d]oxazol-2-yl)-2-(7-fluoro-3,4-dihydrobenzo[b][1,4]oxazepine-5(2H)-yl)isonicotinic acid 20 (3.17 mg), with a yield of 6.6%.

MS m/z (ESI): 440.1 [M+1]

$^1$H NMR (400 MHz, $CDCl_3$) δ 9.32 (s, 1H), 7.63-7.62 (m, 2H), 7.44-7.35 (m, 2H), 7.17-7.14 (m, 1H), 7.05-6.98 (m, 2H), 4.11 (br, 4H), 2.14 (br, 2H).

Example 21

5-(6-fluorobenzo[d]oxazol-2-yl)-2-(7-methoxy-3,4-dihydrobenzo[b][1,4]oxazepine-5(2H)-yl)isonicotinic acid

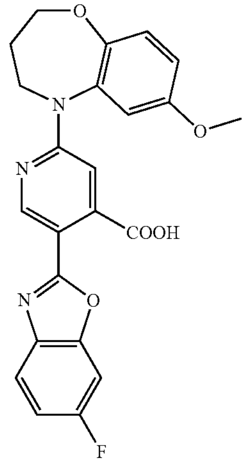

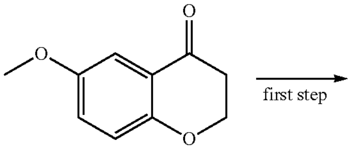

21a

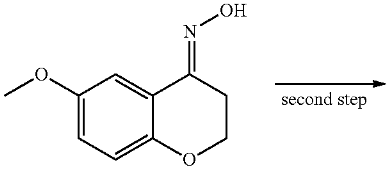

21b

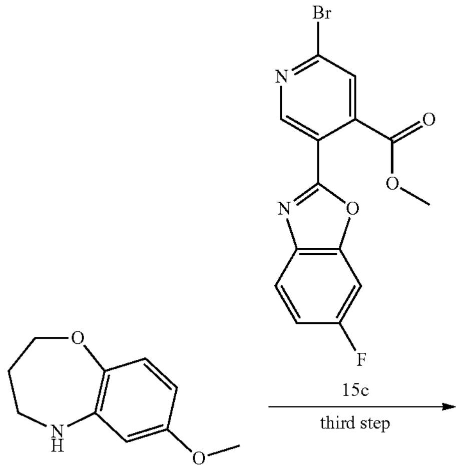

15c

21c

-continued

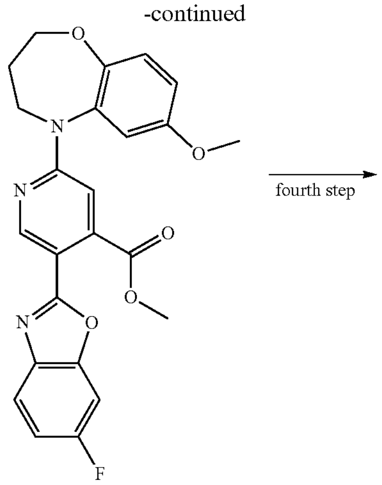

21d

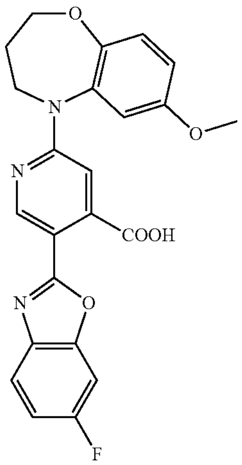

21

First Step (E)-7-methoxy-3,4-dihydrobenzo[b]oxepin-5(2H)-ketoxime 6-methoxychroman-4-one 21a (1.0 g, 6.0 mmol), hydroxylamine hydrochloride (458.7 mg, 6.0 mmol) and triethylamine (668 mg, 6.6 mmol) were dissolved in 8 mL of methanol, and refluxed at 85° C. to perform reaction for 8 hours. After the completion of the reaction, the reaction solution was concentrated under reduced pressure to remove half of methanol, and after being cooled down, it was added with 50 mL of water, stirred at room temperature for 30 minutes to precipitate solid. After filtration, the filter cake was washed with water (25 mL×2), and dried, to obtain (E)-7-methoxy-3,4-dihydrobenzo[b]oxepin-5(2H)-ketoxime 21b (1.0 g), with a yield of 82%.

MS m/z (ESI): 194.1 [M+1]

Second Step 7-methoxy-2,3,4,5-tetrahydrobenzo[b][1,4]oxazepine (E)-7-methoxy-3,4-dihydrobenzo[b]oxepin-5(2H)-ketoxime 21b (1.0 g, 5.18 mmol) was dissolved in 10 mL of dichloromethane, cooled down to 0° C., and slowly added dropwise with 50 mL of 1M solution of diisobutyl aluminum hydride in toluene. After addition, the mixture was heated up to room temperature to continue the reaction for 5 hours. After the completion of the reaction, the reaction solution was slowly added dropwise with methanol to quench the reaction in ice bath, until no more bubbles, and it was continued to stir for 10 minutes, and added with 150 mL of ethyl acetate and 100 mL of water. After liquid separation, the organic phase was collected and dried over anhydrous sodium sulfate, filtered, and concentrated under reduced pressure, to obtain 7-methoxy-2,3,4,5-tetrahydrobenzo[b][1,4]oxazepine 21c (153 mg), with a yield of 18%.

MS m/z (ESI): 180.0 [M+1]

Third Step

Methyl 5-(6-fluorobenzo[d]oxazol-2-yl)-2-(7-methoxy-3,4-dihydrobenzo[b][1,4]oxazepine-5(2H)-yl)isonicotinate Under nitrogen gas atmosphere, methyl 2-bromo-5-(6-fluorobenzo[d]oxazol-2-yl)isonicotinate 15c (300 mg, 0.85 mmol), 7-methoxy-2,3,4,5-tetrahydrobenzo[b][1,4]oxazepane 21c (153 mg, 0.85 mmol), tris(dibenzylideneacetone)dipalladium (78 mg, 0.085 mmol), 4,5-bis(diphenylphosphino)-9,9-dimethylxanthene (Xantphos, 98 mg, 0.17 mmol) and cesium carbonate (553 mg, 1.7 mmol) were dissolved in 5 mL of toluene, and reacted at 90° C. overnight. After the completion of the reaction, the mixture was cooled down to room temperature, and added with 10 mL of water and 20 mL of ethyl acetate, and extracted with ethyl acetate (20 mL×2). The organic phases were combined. The resulting organic phase was washed with 10 mL of saturated sodium chloride solution, dried over anhydrous sodium sulfate, filtered, and concentrated under reduced pressure. The resulting residue was purified with silica gel column chromatography (mobile phase: system A), to obtain methyl 5-(6-fluorobenzo[d]oxazol-2-yl)-2-(7-methoxy-3,4-dihydrobenzo[b][1,4]oxazepine-5(2H)-yl)isonicotinate 21d (80 mg), with a yield of 21%.

MS m/z (ESI): 450.1 [M+1]

Fourth Step 5-(6-fluorobenzo[d]oxazol-2-yl)-2-(7-methoxy-3,4-dihydrobenzo[b][1,4]oxazepine-5(2H)-yl)isonicotinic acid Methyl 5-(6-fluorobenzo[d]oxazol-2-yl)-2-(7-methoxy-3,4-dihydrobenzo[b][1,4]oxazepine-5(2H)-yl)isonicotinate 21d (80 mg, 0.18 mmol) was dissolved in 10 mL of a mixed solvent of tetrahydrofuran and water (V:V=1:1), added with potassium hydroxide (100.8 mg, 1.8 mmol), and stirred at room temperature overnight. After the completion of the reaction, 100 mL of ethyl acetate and 100 mL of water were added. The reaction solution was adjusted to acidity by adding with 2N dilute hydrochloric acid. After liquid separation, the aqueous phase was extracted with ethyl acetate (50 mL×2). The organic phases were combined, dried over anhydrous sodium sulfate, filtered, and concentrated under reduced pressure. The resulting residue was separated and purified with a preparative column, to obtain 5-(6-fluorobenzo[d]oxazol-2-yl)-2-(7-methoxy-3,4-dihydrobenzo[b][1,4]oxazepine-5(2H)-yl)isonicotinic acid 21 (8 mg), with a yield of 10.3%.

MS m/z (ESI): 436.1 [M+1]

Example 22

5-(6-fluorobenzo[d]oxazol-2-yl)-2-(1H-indazol-1-yl)isonicotinic acid

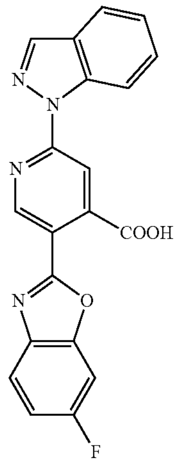

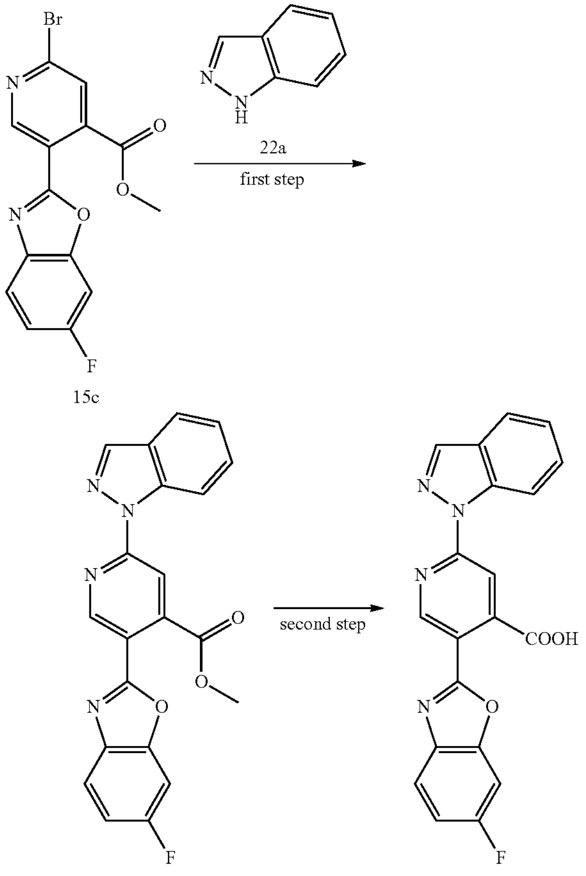

15c

22a

22b

22

First Step

Methyl 5-(6-fluorobenzo[d]oxazol-2-yl)-2-(1H-indazol-1-yl)isonicotinate

Under nitrogen gas atmosphere, methyl 2-bromo-5-(6-fluorobenzo[d]oxazol-2-yl)isonicotinate 15c (250 mg, 0.71 mmol), indazole 22a (80.4 mg, 0.68 mmol), tris(dibenzylideneacetone)dipalladium (63 mg, 0.068 mmol), 4,5-bis(diphenylphosphino)-9,9-dimethylxanthene (Xantphos, 78.7 mg, 0.136 mmol) and cesium carbonate (443 mg, 1.36 mmol) were dissolved in 10 mL of toluene, and reacted at 90° C. overnight. After the completion of the reaction, the mixture was cooled down to room temperature, added with 20 mL of water and 30 mL of ethyl acetate, and extracted with ethyl acetate (50 mL×2). The organic phases were combined, washed with 50 mL of saturated sodium chloride solution, dried over anhydrous sodium sulfate, filtered, and concentrated under reduced pressure. The resulting residue was purified with silica gel column chromatography (mobile phase: system A), to obtain methyl 5-(6-fluorobenzo[d]oxazol-2-yl)-2-(1H-indazol-1-yl)isonicotinate 22b (160 mg), with a yield of 58%.

MS m/z (ESI): 388.9 [M+1]

$^1$H NMR (400 MHz, $CDCl_3$) δ 9.23 (s, 1H), 8.88 (d, J=8.8 Hz, 1H), 8.36 (s, 1H), 8.26 (s, 1H), 7.79 (d, J=8.0 Hz, 1H), 7.72 (dd, J=8.8, 4.8 Hz, 1H), 7.58 (t, J=7.6 Hz, 1H), 7.36-7.31 (m, 2H), 7.16-7.11 (m, 1H), 4.00 (s, 3H).

Second Step 5-(6-fluorobenzo[d]oxazol-2-yl)-2-(1H-indazol-1-yl)isonicotinic acid Methyl 5-(6-fluorobenzo[d]oxazol-2-yl)-2-(1H-indazol-1-yl)isonicotinate 22b (156 mg, 0.40 mmol) was dissolved in 10 mL of a mixed solvent of tetrahydrofuran and water (V:V=1:1), and added with potassium hydroxide (224 mg, 4.0 mmol), and reacted at room temperature overnight. After the completion of the reaction, the solution was added with 100 mL of ethyl acetate and 100 mL of water, and adjusted to a pH=3 with 2N dilute hydrochloric acid solution. After liquid separation, the aqueous phase was extracted with ethyl acetate (50 mL×2). The resulting organic phases were combined, dried over anhydrous sodium sulfate, filtered, and concentrated under reduced pressure. The resulting residue was separated and purified with a preparative column, to obtain 5-(6-fluorobenzo[d]oxazol-2-yl)-2-(1H-indazol-1-yl) isonicotinic acid 22 (80 mg), with a yield of 53%.

MS m/z (ESI): 375.0 [M+1]

$^1$H NMR (400 MHz, DMSO-d6) δ 9.17 (s, 1H), 8.81 (d, J=8.8 Hz, 1H), 8.60 (s, 1H), 8.28 (s, 1H), 7.96 (d, J=8.0 Hz, 1H), 7.90 (dd, J=8.8, 5.2 Hz, 1H), 7.83 (dd, J=8.4, 2.4 Hz, 1H), 7.66 (t, J=8.0 Hz, 1H), 7.41 (t, J=7.6 Hz, 1H), 7.37-7.32 (m, 1H).

Example 23

2-(6-fluoro-2,3-dihydro-4H-benzo[b][1,4]oxazin-4-yl)-5-(6-fluorobenzo[d]oxazol-2-yl)isonicotinic acid

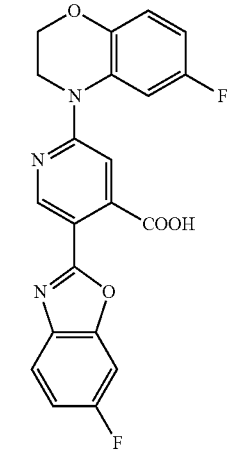

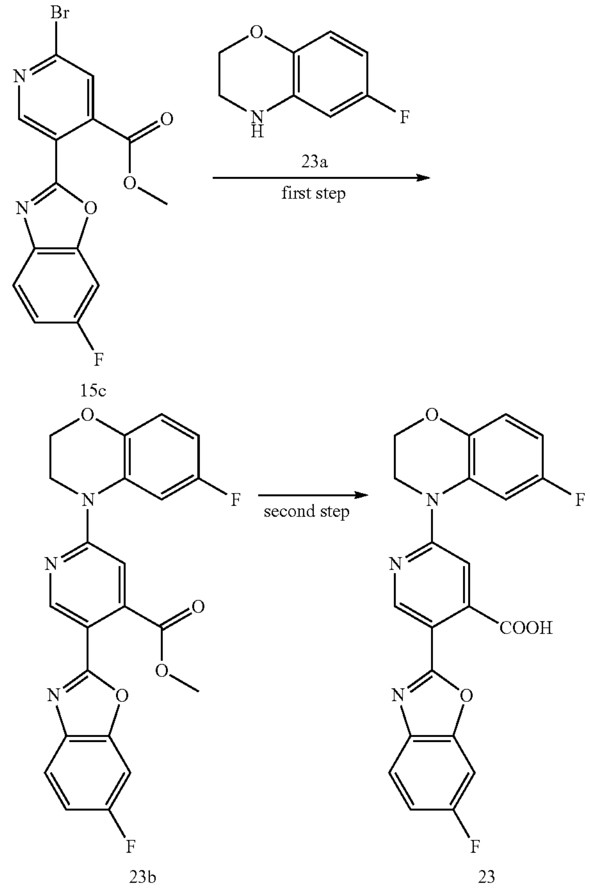

First Step

Methyl 2-(6-fluoro-2,3-dihydro-4H-benzo[b][1,4]oxazin-4-yl)-5-(6-fluorobenzo[d]oxazol-2-yl)isonicotinate Under nitrogen gas atmosphere, methyl 2-bromo-5-(6-fluorobenzo[d]oxazol-2-yl)isonicotinate 15c (250 mg, 0.68 mmol), 6-fluoro-3,4-dihydro-2H-benzo[b][1,4]oxazine 23a (107 mg, 0.68 mmol), tris(dibenzylideneacetone)dipalladium (63 mg, 0.068 mmol), 4,5-bis(diphenylphosphino)-9,9-dimethylxanthene (Xantphos, 78.7 mg, 0.136 mmol) and cesium carbonate (443.1 mg, 1.36 mmol) were dissolved in 20 mL of toluene, and reacted at 85° C. overnight. After the completion of the reaction, the mixture was cooled down to room temperature, added with 20 mL of water and 30 mL of ethyl acetate, and extracted with ethyl acetate (30 mL×2). The organic phases were combined, washed with 30 mL of saturated sodium chloride solution, dried over anhydrous sodium sulfate, filtered, and concentrated under reduced pressure. The resulting residue was purified with silica gel column chromatography (mobile phase: system A), to obtain methyl 2-(6-fluoro-2,3-dihydro-4H-benzo[b][1,4]oxazin-4-yl)-5-(6-fluorobenzo[d]oxazol-2-yl)isonicotinate 23b (140 mg), with a yield of 48%.

MS m/z (ESI): 424.0 [M+1]

Second Step 2-(6-fluoro-2,3-dihydro-4H-benzo[b][1,4]oxazin-4-yl)-5-(6-fluorobenzo[d]oxazol-2-yl)isonicotinic acid Methyl 2-(6-fluoro-2,3-dihydro-4H-benzo[b][1,4]oxazin-4-yl)-5-(6-fluorobenzo[d]oxazol-2-yl)isonicotinate 23b (140 mg, 0.33 mmol) was dissolved in 10 mL a mixed solvent of tetrahydrofuran and water (V:V=1:1), and added with potassium hydroxide (93 mg, 1.65 mmol), and reacted at room temperature overnight. After the completion of the reaction, the solution was added with 100 mL of ethyl acetate and 100 mL of water, and adjusted to a pH=3 with 2N dilute hydrochloric acid. After liquid separation, the aqueous phase was extracted with ethyl acetate (50 mL×2). The organic phases were combined, dried over anhydrous sodium sulfate, filtered, and concentrated under reduced pressure. The resulting residue was separated and purified with a preparative column, to obtain 2-(6-fluoro-2,3-dihydro-4H-benzo[b][1,4]oxazin-4-yl)-5-(6-fluorobenzo[d]oxazol-2-yl)isonicotinic acid 23 (85 mg), with a yield of 63%.

MS m/z (ESI): 410.0 [M+1]

$^1$H NMR (400 MHz, DMSO-d6) δ 9.27 (s, 1H), 8.31 (s, 1H), 7.73 (dd, J=8.8, 4.4 Hz, 1H), 7.41 (dd, J=7.6, 2.4 Hz, 1H), 7.29-7.20 (m, 2H), 6.92 (dd, J=9.2, 5.6 Hz, 1H), 6.82-6.77 (m, 1H), 4.34 (t, J=4.8 Hz, 2H), 4.23 (t, J=4.8 Hz, 2H).

Example 24

5-(benzo[d]oxazol-2-yl)-2-(3,4-dihydroquinoline-1(2H)-yl)isonicotinic acid

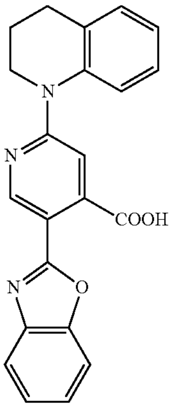

-continued

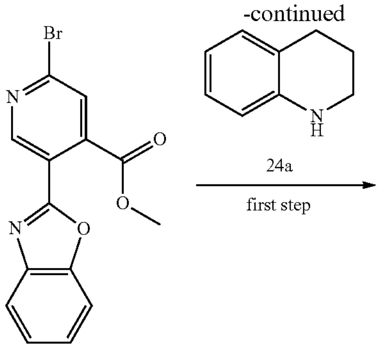

12e

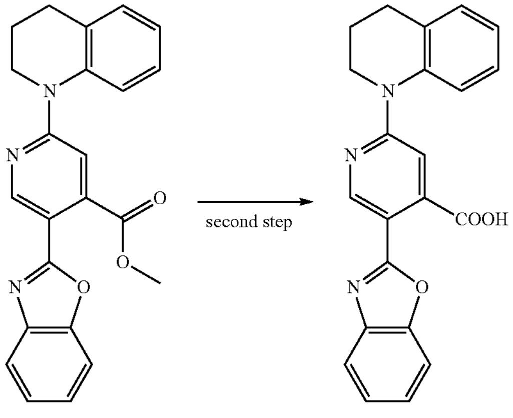

24b 24

First Step

Methyl 5-(benzo[d]oxazol-2-yl)-2-(3,4-dihydroquinoline-1(2H)-yl)isonicotinate

Under nitrogen gas atmosphere, methyl 5-(benzo[d]oxazol-2-yl)-2-bromoisonicotinate 12e (120 mg, 0.36 mmol), 1,2,3,4-tetrahydroquinoline 24a (58 mg, 0.43 mmol), tris(dibenzylideneacetone)dipalladium (33 mg, 0.036 mmol), 4,5-bis(diphenylphosphino)-9,9-dimethylxanthene (Xantphos, 42 mg, 0.072 mmol) and cesium carbonate (352 mg, 1.08 mmol) were dissolved in 3 mL of toluene, and reacted at 89-95° C. overnight. After the completion of the reaction, the mixture was cooled down to room temperature, and added with 20 mL of water and 30 mL of ethyl acetate, and extracted with ethyl acetate (30 mL×2). The organic phases were combined, washed with 30 mL of saturated sodium chloride solution, dried over anhydrous sodium sulfate, filtered, and concentrated under reduced pressure. The resulting residue was purified with silica gel column chromatography (mobile phase: system A), to obtain methyl 5-(benzo[d]oxazol-2-yl)-2-(3,4-dihydroquinoline-1(2H)-yl)isonicotinate 24b (20 mg), with a yield of 14.6%.

MS m/z (ESI): 386.1 [M+1]

Second Step 5-(benzo[d]oxazol-2-yl)-2-(3,4-dihydroquinoline-1(2H)-yl)isonicotinic acid Methyl 5-(benzo[d]oxazol-2-yl)-2-(3,4-dihydroquinoline-1(2H)-yl)isonicotinate 24b (20 mg, 0.05 mmol) was dissolved in 8 mL of methanol, added with 1.8 mL of water, and then added with sodium hydroxide (10 mg, 0.25 mmol), and reacted at room temperature overnight. After the completion of the reaction, the solution was added with 10 mL of ethyl acetate and 10 mL of water, and adjusted to a pH=2-3 with 2N dilute hydrochloric acid. After liquid separation, the aqueous phase was extracted with ethyl acetate (30 mL). The organic phases were combined, dried over anhydrous sodium sulfate, filtered, and concentrated under reduced pressure. The resulting residue was separated and purified with a preparative column, to obtain 5-(benzo[d]oxazol-2-yl)-2-(3,4-dihydroquinoline-1(2H)-yl)isonicotinic acid 24 (10 mg), with a yield of 54%.

MS m/z (ESI): 372.0[M+1]

$^1$H NMR (400 MHz, CDCl3) δ 9.28 (s, 1H), 8.27 (s, 1H), 7.75-7.73 (m, 1H), 7.67-7.65 (m, 1H), 7.48-7.41 (m, 3H), 7.23-7.21 (m, 2H), 7.11 (t, J=7.4 Hz, 1H), 4.07 (t, J=6.4 Hz, 2H), 2.80 (d, J=6.4 Hz, 2H), 2.10-2.01 (m, 2H).

Biological Evaluation

Test Example 1 Test of the Antagonistic Activity of the Compound of the Present Disclosure on the Binding of Human $AT_2R$ Ligand Angiotensin II Type 2 Receptor ($AT_2R$) is involved in neuron differentiation and regeneration, cell proliferation and angiogenesis, and maintenance of bone mass. $AT_2R$ inhibitors can be used for the treatment of pain and abnormal nerve regeneration diseases, inhibit the proliferation of tumor cells and increase bone mass. The following method uses the $AT_2$ ligand binding test to study the degree of antagonism of the compounds of the present disclosure to $AT_2R$.

1. Reagents and Consumables

| | manufacturer | catalog No. |
|---|---|---|
| materials and reagents | | |
| Tag-lite Angiotensin AT2 labeled Cells, ready-to-use (transformed & labeled), 200 tests* (384-well small volume white plate, 20 ul) | Cisbio | C1TT1AT2 |
| Angiotensin AT2 Receptor red agonist Fluorescent Ligand, 5000 test (384-well small volume plate, 20 ul) | Cisbio | L0007RED |
| Tag-lite Buffer (5X concentrate), 100 mL | Cisbio | LABMED |
| Angiotensin II human (CAS: 4474-91-3) DRVYIHPF, 10 mg, MW: 1046.18 | MedChem Express | HY-13948 |
| consumables | | |
| 384-well low volume plate (40 plates/box) | Greiner | 784075 |
| Echo qualified 384-well polypropylidene microplate, clear, flat bottom (100 plates/case) | LABCYTE | P-05525 |
| 384-well round bottom, no lid, non-sterile, polypropylidene (100 plates/case) | Corning | 3657 |
| 96-well conical btm PP Plt nature RNASE/Dnase-free plate (120 plates/case) | ThermoFisher | 249944 |

2. Reagent Preparation (1) 10 mM of angiotensin II human: 10 mg of Angiotensin II human (purity 99.09%) was dissolved in 0.947 mL of deionized water, aliquoted and stored at −80° C.;

(2) Preparation of compound stock solution

According to standard methods, all compounds were dissolved in dimethyl sulfoxide and prepared as a 10 mM stock solution.

(3) Tag-lite angiotensin receptor red agonist: 8600 nM stock solution was aliquoted and stored at −80° C.;

(4) 1× Tag-Lite Buffer (TLB): 5×TLB was diluted with deionized water to 1×.

3. Experimental Steps (1) An appropriate amount of 1×TLB was prepared and mixed well for later use;

(2) The test compound were diluted 5 times with a total of 10 concentration gradients;

(3) 160 nL/well of each compound diluted in step (2) was transferred to a working plate (3657, Corning), and centrifuged at 200 g for 1 minute at room temperature;

(4) 40 μl 1×TLB was added to the above working plate, centrifuged at 200 g for 1 minute at room temperature, shaked on a shaker for 15 minutes to mix, and centrifuged at 200 g for 1 minute at room temperature for later use (the working concentration of the compound was 4×);

(5) 1×TLB was used to dilute Tag-lite angiotensin receptor red agonist (8600 nM stock solution) to 12 nM for later use;

(6) 5 mL of 1×TLB was taken into a 15 mL centrifuge tube;

(7) A bottle of Tb-labeled-$AT_2R$ cell was frozen and thawed in a 37° C. water bath until the ice was completely melted (1-2 minutes);

(8) The frozen and thawed cells were quickly transferred to the 1×TLB in step (6), mixed gently, and centrifuged at 1200 g for 5 minutes at room temperature;

(9) After supernatant was gently aspirated out, the cells was resuspended using 1 mL of 1×TLB and mixed well, then added with 1.7 mL of 1×TLB. After being mixed well, it was kept at room temperature for later use;

(10) To all test wells, 10 μL of cells were added, and centrifuged for 3 seconds at room temperature at 200 g; 5 μL of the compound working solution 4× in step (4) was added to the corresponding wells; and 5 μL of 4× Tag-lite angiotensin receptor red agonist diluted in step (5) was added to all test wells;

(11) The reaction plate was centrifuged at room temperature for 1 minute at 200 g; after standing at room temperature for 1 hour, it was centrifuged at room temperature for 1 minute at 200 g; the data was collected using Envision HTRF enzyme reader; and $IC_{50}$ was calculated using a nonlinear fitting equation.

(12) In the same way, the same method was adopted to test $IC_{50}$ of the antagonistic activity of the compounds of the present disclosure on $AT_1R$, except that Tb-labeled-$AT_1R$ cells were used instead of Tb-labeled-$AT_2R$ cells.

4. Experimental Results $IC_{50}$ tested for the $AT_2R$ antagonistic activity of the compounds of the present disclosure are shown in the following table.

| compound No. | $IC_{50}$ (nM)/$AT_2R$ | $IC_{50}$ (μM)/$AT_1R$ |
|---|---|---|
| olodanrigan | 49 | >10 |
| 4 | 37 | >10 |
| 5 | 10 | >10 |
| 6 | 26 | >10 |
| 8 | 28 | >10 |
| 12 | 12 | >10 |
| 14 | 4.1 | >10 |
| 15 | 2.3 | >10 |
| 16 | 7.5 | >10 |
| 17 | 13 | >10 |
| 18 | 4.7 | >10 |
| 19 | 2.3 | >10 |

Conclusions:

(1) The compounds of the present disclosure have significant antagonistic activity against $AT_2R$;

(2) The compounds of the present disclosure have an antagonistic $IC_{50}$>10 μM for $AT_1R$, and have no antagonistic activity for $AT_1R$;

Therefore, the compounds of the present disclosure are highly selective for $AT_2R$ antagonism.

Test Example 2. Study on the Metabolic Stability of the Compounds of the Present Disclosure in Rat Liver Microsomes 1. Experimental Purposes The purpose of this experimental study is to study the metabolic stability of the compounds of the present disclosure in rat liver microsomes.

2. Reagent Information

| Name | Lot number | Supplier |
|---|---|---|
| rat liver microsomes | 5118007 | Corning (US) |
| Midazolam maleate | 171265-201402 | National Institute for Food and Drug Control |
| NADPH | 20595626 | Roche (Switzerland) |
| potassium dihydrogen phosphate | 20150428 | Sinopharm Chemical Reagent Co., Ltd. |
| dipotassium phosphate | 20150312 | Sinopharm Chemical Reagent Co., Ltd. |
| magnesium chloride ($MgCl_2$) | F20090916 | Sinopharm Chemical Reagent Co., Ltd. |
| verapamil hydrochloride | 100223-200102 | National Institute for Food and Drug Control |
| glibenclamide | 100135-201105 | National Institute for Food and Drug Control |
| DMSO | 1427C108 | Amresco (US) |
| methanol | QADG3H | Honeywell (US) |
| acetonitrile | S13A1H | Honeywell (US) |
| formic acid | A1819048 | Shanghai Aladdin Biochemical Technology Co., Ltd. |

3. Experimental Program

The test compounds were co-incubated with rat liver microsomes, and the coenzyme NADPH was added to initiate the reaction. At 0, 5, 15, 30, and 60 minutes, 20 μL of incubation solution was taken out and transferred to 200 μL of acetonitrile containing internal standard to stop the reaction. After protein precipitation, it was centrifuged at 3,700 rpm for 10 minutes. The supernatant was taken and analyzed by LC-MS/MS method after being diluted at 1:1 with water. According to the elimination half-life of the test compound in the incubation system, the in vitro clearance rate was calculated. Midazolam was used as the internal reference compound and incubated for 2 copies in parallel. The incubation conditions are summarized in the following table:

| | |
|---|---|
| liver microsomes | 0.5 mg · $mL^{-1}$ (test compounds); 0.2 mg · $mL^{-1}$ (midazolam) |
| incubation buffer | phosphoric acid buffer (100 mM, pH 7.4) |
| initial concentration of test compound incubation | 1 μM |
| final volume of incubation system | 0.2 mL |
| incubation time | 0, 5, 15, 30, 60 min (compounds of the present disclosure) 0, 5, 20 min (midazolam) |

-continued

| | |
|---|---|
| magnesium chloride | 3 mM |
| NADPH | 1 mM |
| parallel reaction | 2 copies in parallel |

4. Data Analysis

The ratio of analyte/internal standard peak area ($A_{analyte}/A_{IS}$) was obtained from the instrument, and the remaining percentage (% Control) was calculated as the ratio of $A_{analyte}/A_{IS}$ in the non-zero time point sample to the zero time point sample. Ln (% Control) versus incubation time was plotted and subjected to a linear fitting. The clearance constant (k, min-) and clearance half-life ($T_{1/2}$, min) of the test compounds were calculated by the following equations.

$$k = -\text{slope}$$

$$T_{1/2} = 0.693/k$$

4. Experimental Results

The related parameters of the stability of the compounds of the present disclosure in rat liver microsomes are shown in the following table:

| compound No. | half-life/($T_{1/2}$, min) |
|---|---|
| olodanrigan | 96.3 |
| 4 | 185 |
| 12 | 288 |
| 14 | 600 |
| 15 | 160 |
| 16 | 598 |

Conclusion: Compared with olodanrigan, the compounds of the present disclosure have a significantly prolonged half-life, and the stability in rat liver microsomes is significantly improved.

Test Example 3. Study on Oral Pharmacokinetics of the Compounds of the Present Disclosure in SD Rats 1. Experimental Purposes SD rats were taken as the test animals. The LC/MS/MS method was used to determine the intravenous injection or intragastric administration of the compounds of the present disclosure in rats, and to determine the drug concentration in plasma at different time points to study the pharmacokinetic characteristics of the compounds of the present disclosure in rats.

2. Experimental Scheme 2.1 Experimental Drugs and Animals

Experimental drugs: Olodanrigan, compounds 12, 14, 15 and 16 of the present disclosure;

Animals: 30 healthy adult Sprague Dawley (SD) male rats, purchased from Weitong Lihua Experimental Animal Technology Co. Ltd., production license number: 11400700271077.

2.2 Drug Formulation and Administration

Intravenous Injection Group:

An appropriate amount of samples were weighed, and added with DMA, solutol HS 15 (30%, w/v) and normal saline respectively, and then subjected to ultrasound and filtered through PTFE membrane to make a 0.2 mg/mL solution.

Oral Intragastric Administration Group:

An appropriate amount of samples were weighed, added with 0.5% sodium carboxymethyl cellulose (CMC-Na) (containing 0.5% Tween 80), and ultrasonically prepared into a 1 mg/mL suspension.

30 healthy adult male SD rats were fasted overnight, and given tail vein injection (dose: 1 mg/kg) and intragastric administration (dose: 10 mg/kg) respectively, and fed 4 hours after administration.

2.3 Sample Collection

About 0.2 mL of blood was collected from the jugular vein before administration and at 0.083 hours, 0.25 hours, 0.5 hours, 1 hour, 2 hours, 4 hours, 8 hours, 12 hours, and 24 hours after administration, and heparin sodium was used for anticoagulation. The blood samples were collected on ice and centrifuged to separate the plasma (centrifugation conditions: 1500 g, 10 minutes). The collected plasma was stored at −40 to −20° C. before analysis.

2.4 Pretreatment of Sample

10 μL of plasma sample was taken and added with 400 μL of acetonitrile (comprising internal standard working solution which contained verapamil 5 ng/mL and glibenclamide 50 ng/mL). It was vortexed for 10 minutes, centrifuge at 3700 rpm for 10 minutes. 70 μL of the supernatant was taken and added with 70 μL of water, and vortexed for 10 minutes. 2 μL of the mixed solution was taken and injected into LC-MS/MS for sample analysis.

3. Pharmacokinetic Parameter Results

The pharmacokinetic parameters of the compounds of the present disclosure and the positive control are shown in the following table.

| | pharmacokinetic parameters | | | | | |
|---|---|---|---|---|---|---|
| Example No. | mode of administration, dosage of administration | drug concentration in blood, $C_{max}$ (ng/mL) | area under curve $AUO_{0-\infty}$ (ng · h/mL) | half-life $T_{1/2}$(h) | residence time MRT(h) | bioavailability F(%) |
| olodanrigan | oral (mg/kg) | 470 ± 197 | 1483 ± 715 | 1.5 ± 0.3 | 2.6 ± 1.0 | 12.1 |
| | injection (1 mg/kg) | N/A | 1230 ± 96 | 1.6 ± 0.3 | 0.92 ± 0.16 | |
| 12 | oral (3 mg/kg) | 8650 ± 6017 | 40400 ± 14272 | 4.7 ± 0.3 | 6.1 ± 0.5 | 83.1 |
| | injection (1 mg/kg) | N/A | 16200 ± 3530 | 8.1 ± 2.1 | 7.3 ± 1.5 | |
| 14 | oral (3 mg/kg) | 14300 ± 5128 | 43400 ± 11173 | 3.6 ± 0.2 | 4.7 ± 0.3 | 104.8 |
| | injection (1 mg/kg) | N/A | 13800 ± 1370 | 4.7 ± 0.4 | 4.5 ± 0.2 | |
| 15 | oral (3 mg/kg) | 7050 ± 2638 | 32400 ± 6514 | 4.2 ± 0.4 | 5.2 ± 0.4 | 89.9 |
| | injection (1 mg/kg) | N/A | 12100 ± 751 | 4.5 ± 0.4 | 4.5 ± 0.4 | |
| 16 | oral (mg/kg) | 5250 ± 315 | 25800 ± 6100 | 3.7 ± 0.4 | 5.5 ± 0.4 | 41.3 |
| | injection (1 mg/kg) | N/A | 20800 ± 1740 | 3.3 ± 0.2 | 3.2 ± 0.3 | |

The invention claimed is:

1. A compound represented by general formula (I):

(I)

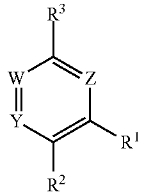

wherein W, Y and Z are each independently selected from $CR^n$ and N, and there are at most 2 N atoms contained among W, Y, and Z;

$R^1$ is selected from —$COOR^a$ and tetrazolyl;

$R^2$ is selected from 8- to 10-membered heteroaryl and —$NR^bR^c$, wherein the heteroaryl is optionally further substituted with one or more substituents selected from $R^d$;

$R^3$ is selected from —$NR^eR^f$ and the group

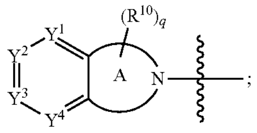

;

$Y^1$, $Y^2$, $Y^3$ and $Y^4$ are each independently selected from $CR^j$ and N, and there are at most 3 N atoms contained among $Y^1$, $Y^2$, $Y^3$ and $Y^4$;

ring A is selected from 6- to 8-membered monocyclic heterocyclyl and 5-membered heteroaryl, wherein the monocyclic heterocyclyl contains one or more N, O or $S(O)_n$ therein, and the 6- to 8-membered heterocycle is optionally further substituted by one or more $R^{10}$;

$R^a$ is selected from hydrogen atom and alkyl, wherein the alkyl is optionally further substituted with one or more halogens;

$R^b$ is the group:

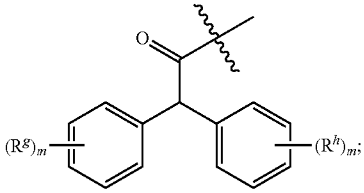

;

$R^c$ is alkyl;

$R^e$ is selected from hydrogen atom and alkyl, wherein the alkyl is optionally further substituted with one or more substituents selected from hydroxyl, alkoxy and halogen;

$R^f$ is selected from -L-$R^k$,

L is selected from $C_{1-6}$ alkylene;

wherein the $C_{1-6}$ alkylene is substituted or unsubstituted, when the $C_{1-6}$ alkylene is substituted, the $C_{1-6}$ alkylene is substituted by one or more groups selected from the following: alkyl, alkenyl, alkynyl, alkoxy, alkylthio, alkylamino, halogen, mercapto, hydroxyl, nitro, cyano, cycloalkyl, heterocyclyl, aryl, heteroaryl, cycloalkoxy, heterocycloalkoxy, cycloalkylthio, heterocycloalkylthio, amino, haloalkyl, hydroxyalkyl, carboxyl, carboxylic ester groups, —C(O)$R^4$, —C(O)O$R^4$, —OC(O)$R^4$, —N$R^5R^6$, —C(O)N$R^5R^6$, —$SO_2NR^5R^6$ and —N$R^5$C(O)$R^6$;

$R^g$ and $R^h$ are each independently selected from hydrogen atom, alkyl, alkoxy, halogen and cyano, wherein the alkyl or alkoxy is optionally further substituted with one or more halogen or alkoxy;

$R^k$ is selected from aryl and heteroaryl, wherein the aryl or heteroaryl is optionally further substituted with one or more $R^m$;

$R^d$, $R^j$, $R^m$, $R^n$ and $R^{10}$ are the same or different, and are each independently selected from hydrogen atom, hydroxyl, halogen, nitro, cyano, alkyl, alkoxy, cycloalkyl, heterocyclyl, aryl, heteroaryl, —C(O)$R^4$, —C(O)O$R^4$, —OC(O)$R^4$, —N$R^5R^6$, —C(O)N$R^5R^6$, —$S(O)_nNR^5R^6$ and —N$R^5$C(O)$R^6$, wherein the alkyl, alkoxy, cycloalkyl, heterocyclyl, aryl or heteroaryl is optionally further substituted with one or more substituents selected from hydroxyl, halogen, nitro, cyano, alkoxy, cycloalkyl, heterocyclyl, aryl, heteroaryl, =O, —C(O)$R^4$, —C(O)O$R^4$, —OC(O)$R^4$, —N$R^5R^6$, —C(O)N$R^5R^6$, —$SO_2NR^5R^6$ and —N$R^5$C(O)$R^6$;

$R^4$, $R^5$ and $R^6$ are each independently selected from hydrogen atom, hydroxyl, halogen, nitro, cyano, alkyl, alkoxy, cycloalkyl, heterocyclyl, aryl and heteroaryl, wherein the alkyl, alkoxy, cycloalkyl, heterocyclyl, aryl or heteroaryl is optionally further substituted with one or more substituents selected from hydroxyl, halogen, nitro, cyano, alkyl, alkoxy, cycloalkyl, heterocyclyl, aryl, heteroaryl, —C(O)$R^7$, —C(O)O$R^7$, —OC(O)$R^7$, —N$R^8R^9$, —C(O)N$R^8R^9$, —$SO_2NR^8R^9$ and —N$R^8$C(O)$R^9$;

or, $R^5$ and $R^6$, together with the N atom connected thereto, form a 4- to 8-membered heterocyclyl, wherein the 4- to 8-membered heterocycle contains one or more N, O or $S(O)_n$, and the 4- to 8-membered heterocycle is optionally further substituted with one or more substituents selected from hydroxyl, halogen, nitro, cyano, alkyl, alkoxy, cycloalkyl, heterocyclyl, aryl, heteroaryl, =O, —C(O)$R^7$, —C(O)O$R^7$, —OC(O)$R^7$, —N$R^8R^9$, —C(O)N$R^8R^9$, —$SO_2NR^8R^9$ and —N$R^8$C(O)$R^9$;

$R^7$, $R^8$ and $R^9$ are each independently selected from hydrogen, alkyl, cycloalkyl, heterocyclyl, aryl and heteroaryl, wherein the alkyl, cycloalkyl, heterocyclyl, aryl or heteroaryl is optionally further substituted with one or more substituents selected from hydroxyl, halogen, nitro, cyano, alkyl, alkoxy, cycloalkyl, heterocyclyl, aryl, heteroaryl, carboxyl and carboxylic ester groups;

m is selected from 0, 1, 2, 3, 4 and 5;

n is selected from 0, 1 and 2; and q is 0, 1, 2, 3, 4 or 5;

a stereoisomer, a tautomer or a pharmaceutically acceptable salt thereof.

2. A compound represented by general formula (II) or a stereoisomer, a tautomer or a pharmaceutically acceptable salt thereof, (II)

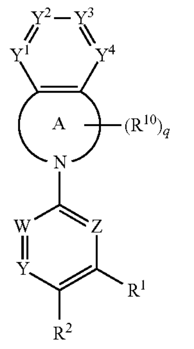

wherein W, Y and Z are each independently selected from CH and N, and there is at most 1 N atom contained among W, Y, and Z;

$Y^1$, $Y^2$, $Y^3$ and $Y^4$ are each independently selected from $CR^j$ and N, and there is at most 1 N atom contained among $Y^1$, $Y^2$, $Y^3$ and $Y^4$;

ring A is selected from 6- to 8-membered monocyclic heterocyclyl, wherein the monocyclic heterocyclyl contains one or more N, O or $S(O)_n$ therein, and the 6- to 8-membered heterocycle is optionally further substituted with one or more $R^{10}$;

$R^{10}$ are the same or different, and are each independently selected from halogen, alkyl, alkoxy and =O, wherein the alkyl or alkoxy is optionally further substituted with halogen;

$R^j$ are the same or different, and are each independently selected from hydrogen atom, alkyl, alkoxy and halogen, wherein the alkyl or alkoxy is optionally further substituted with halogen;

q is 0, 1, 2 or 3;

$R^1$ is selected from —COO$R^a$ and tetrazolyl;

$R^2$ is selected from 8- to 10-membered heteroaryl and —N$R^bR^c$, wherein the heteroaryl is optionally further substituted with one or more substituents selected from $R^d$;

$R^a$ is selected from hydrogen atom and alkyl, wherein the alkyl is optionally further substituted with one or more halogens;

$R^b$ is the group:

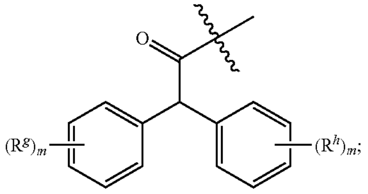

$R^c$ is alkyl;

$R^d$ is selected from hydrogen atom, hydroxyl, halogen, nitro, cyano, alkyl, alkoxy, cycloalkyl, heterocyclyl, aryl, heteroaryl, —C(O)$R^4$, —C(O)O$R^4$, —OC(O)$R^4$, —N$R^5R^6$, —C(O)N$R^5R^6$, —$S(O)_nNR^5R^6$ and —N$R^5$C(O)$R^6$, wherein the alkyl, alkoxy, cycloalkyl, heterocyclyl, aryl or heteroaryl is optionally further substituted with one or more substituents selected from hydroxyl, halogen, nitro, cyano, alkoxy, cycloalkyl, heterocyclyl, aryl, heteroaryl, =O, —C(O)$R^4$, —C(O)O$R^4$, —OC(O)$R^4$, —N$R^5R^6$, —C(O)N$R^5R^6$, —$SO_2NR^5R^6$ and —N$R^5$C(O)$R^6$;

$R^4$, $R^5$ and $R^6$ are each independently selected from hydrogen atom, hydroxyl, halogen, nitro, cyano, alkyl, alkoxy, cycloalkyl, heterocyclyl, aryl and heteroaryl, wherein the alkyl, alkoxy, cycloalkyl, heterocyclyl, aryl or heteroaryl is optionally further substituted with one or more substituents selected from hydroxyl, halogen, nitro, cyano, alkyl, alkoxy, cycloalkyl, heterocyclyl, aryl, heteroaryl, —C(O)$R^7$, —C(O)O$R^7$, —OC(O)$R^7$, —N$R^8R^9$, —C(O)N$R^8R^9$, —$SO_2NR^8R^9$ and —N$R^8$C(O)$R^9$;

or, $R^5$ and $R^6$, together with the N atom connected thereto, form a 4- to 8-membered heterocyclyl, wherein the 4- to 8-membered heterocycle contains one or more N, O or $S(O)_n$, and the 4- to 8-membered heterocycle is optionally further substituted with one or more substituents selected from hydroxyl, halogen, nitro, cyano, alkyl, alkoxy, cycloalkyl, heterocyclyl, aryl, heteroaryl, =O, —C(O)$R^7$, —C(O)O$R^7$, —OC(O)$R^7$, —N$R^8R^9$, —C(O)N$R^8R^9$, —$SO_2NR^8R^9$ and —N$R^8$C(O)$R^9$;

$R^7$, $R^8$ and $R^9$ are each independently selected from hydrogen, alkyl, cycloalkyl, heterocyclyl, aryl and heteroaryl, wherein the alkyl, cycloalkyl, heterocyclyl, aryl or heteroaryl is optionally further substituted with one or more substituents selected from hydroxyl, halogen, nitro, cyano, alkyl, alkoxy, cycloalkyl, heterocyclyl, aryl, heteroaryl, carboxyl and carboxylic ester groups;

$R^g$ and $R^h$ are each independently selected from hydrogen atom, alkyl, alkoxy, halogen and cyano, wherein the alkyl or alkoxy is optionally further substituted with one or more halogen or alkoxy;

m is selected from 0, 1, 2, 3, 4 and 5; and n is selected from 0, 1 and 2.

3. The compound or the stereoisomer, the tautomer or the pharmaceutically acceptable salt thereof according to claim 1, which is a compound represented by general formula (III) or a stereoisomer, a tautomer or a pharmaceutically acceptable salt thereof, (III)

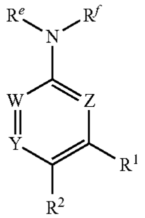

wherein W, Y and Z are each independently selected from CH and N, and there is at most 1 N atom contained among W, Y, and Z;

$R^e$ is selected from hydrogen atom and alkyl;

$R^f$ is selected from -L-$R^k$,

L is selected from $C_{1-6}$ alkylene;

wherein the $C_{1-6}$ alkylene is substituted or unsubstituted, when the $C_{1-6}$ alkylene is substituted, the $C_{1-6}$ alkylene is substituted by one or more groups selected from the following: alkyl, alkenyl, alkynyl, alkoxy, alkylthio, alkylamino, halogen, mercapto, hydroxyl, nitro, cyano, cycloalkyl, heterocyclyl, aryl, heteroaryl, cycloalkoxy, heterocycloalkoxy, cycloalkylthio, heterocycloalkylthio, amino, haloalkyl, hydroxyalkyl, carboxyl, carboxylic ester groups, —C(O)$R^4$, —C(O)O$R^4$, —OC(O)$R^4$, —N$R^5R^6$, —C(O)N$R^5R^6$, —$SO_2NR^5R^6$ and —N$R^5$C(O)$R^6$;

$R^k$ is selected from aryl; wherein the aryl is optionally further substituted with one or more substituents selected from halogen, alkyl and alkoxy; wherein the alkyl or alkoxy is optionally further substituted with one or more halogen; and $R^1$ and $R^2$ are defined as described in claim 1.

4. The compound or the stereoisomer, the tautomer or the pharmaceutically acceptable salt thereof according to claim 1, wherein $R^2$ is selected from the groups:

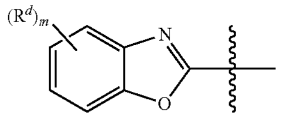
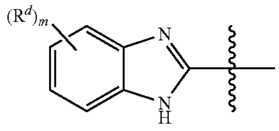
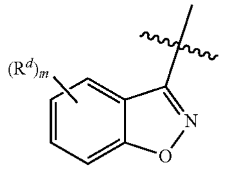
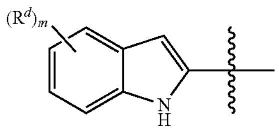
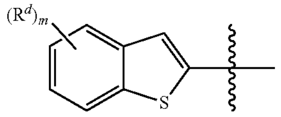
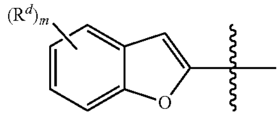
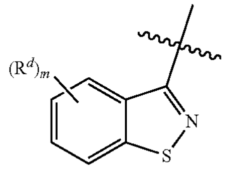
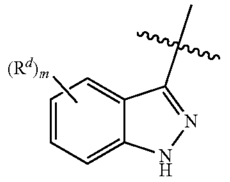
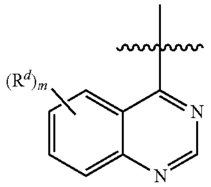
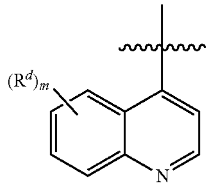
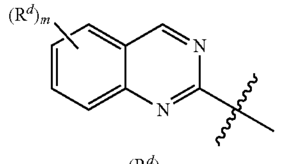
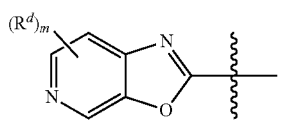
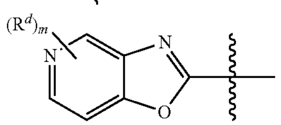
or
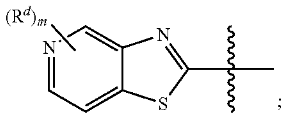
;

$R^d$ are the same or different, and are each independently selected from hydrogen atom, alkyl, cyano, alkoxy and halogen, wherein the alkyl or alkoxy is optionally further substituted with halogen; and m is 0, 1, 2, 3 or 4.

5. The compound or the stereoisomer, the tautomer or the pharmaceutically acceptable salt thereof according to claim 1, wherein $R^2$ is the group:

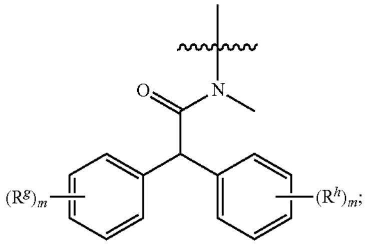

and $R^g$, $R^h$ and m are defined as described in claim 1.

6. The compound or the stereoisomer, the tautomer or the pharmaceutically acceptable salt thereof according to claim 1, wherein $R^2$ is selected from the groups:

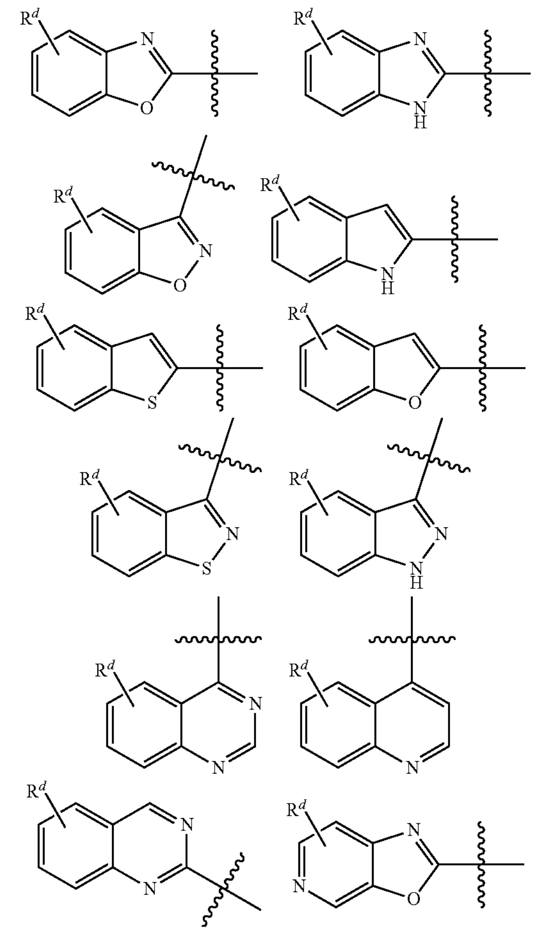

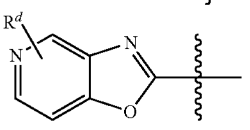

or

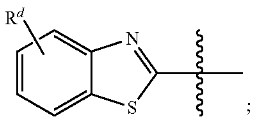

;

and $R^d$ is selected from hydrogen atom, fluorine, chlorine, cyano, methyl, ethyl, isopropyl, difluoromethyl, trifluoromethyl and trifluoromethoxy.

7. The compound or the stereoisomer, the tautomer or the pharmaceutically acceptable salt thereof according to claim 5, wherein $R^g$ and $R^h$ are each independently selected from hydrogen atom, fluorine, chlorine, cyano, methyl, ethyl, isopropyl, difluoromethyl, trifluoromethyl and trifluoromethoxy; and m is 1.

8. The compound or the stereoisomer, the tautomer or the pharmaceutically acceptable salt thereof according to claim 2, wherein

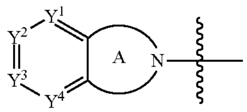

is selected from the groups:

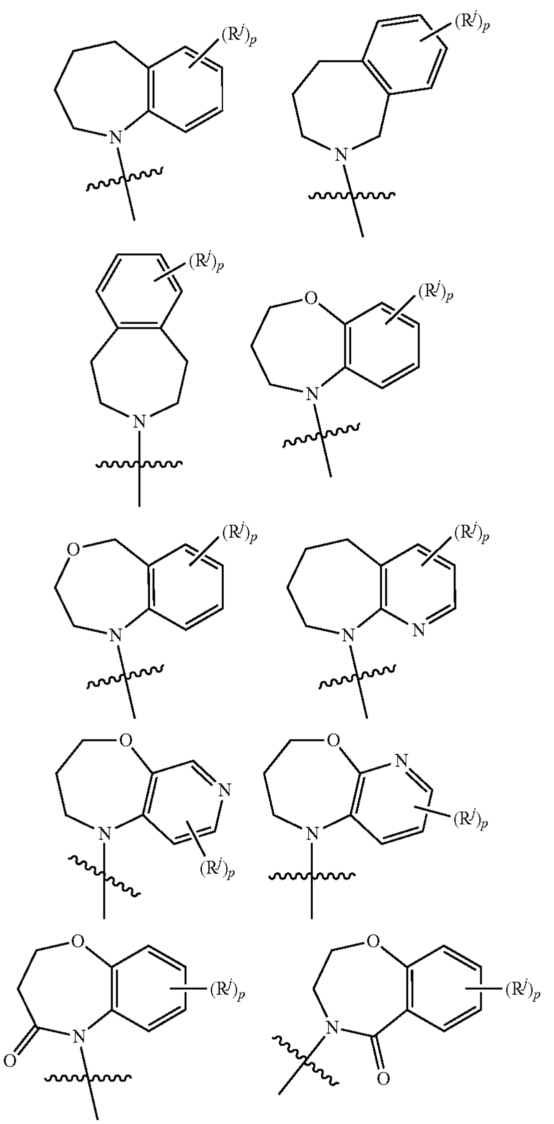

-continued

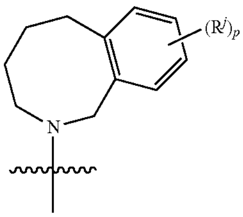
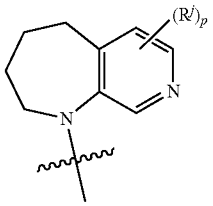
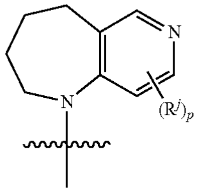
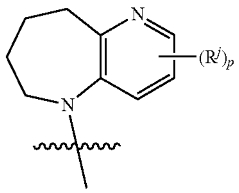
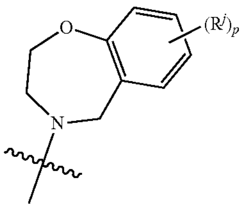
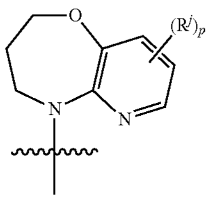
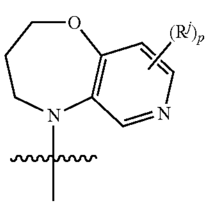
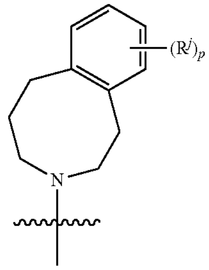
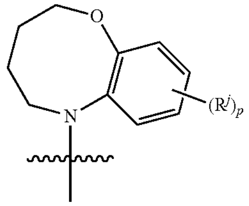
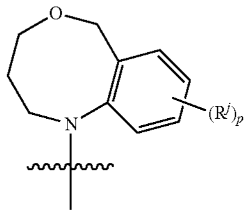
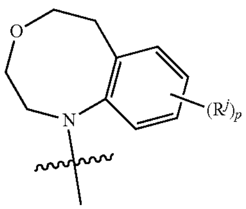
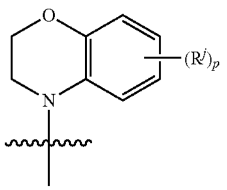

or

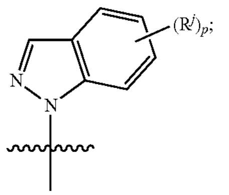

$R^j$ are the same or different, and are each independently selected from hydrogen atom, alkyl, alkoxy and halogen, wherein the alkyl or alkoxy is optionally further substituted with halogen; and p is 0, 1, 2, 3 or 4.

9. The compound or the stereoisomer, the tautomer or the pharmaceutically acceptable salt thereof according to claim 1, wherein the compound is selected from:

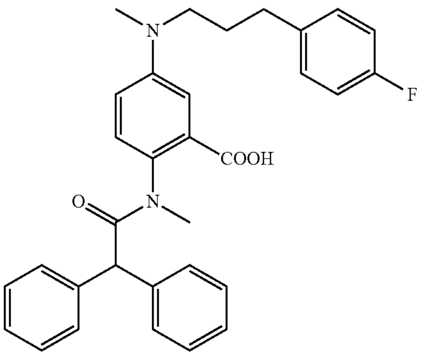
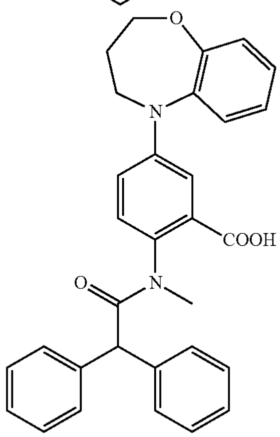
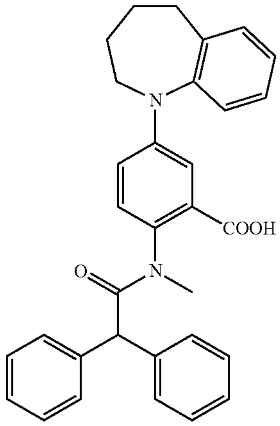
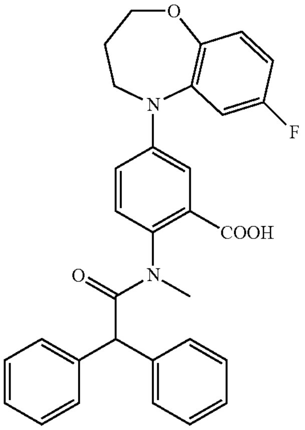

-continued
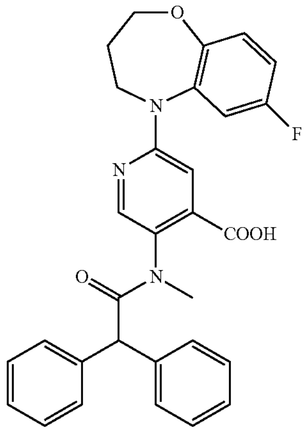
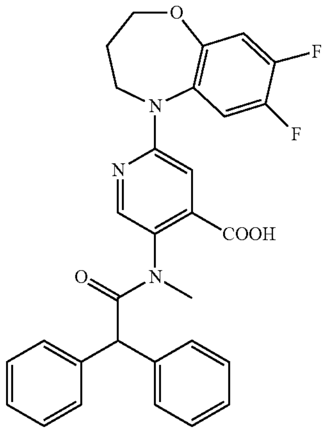
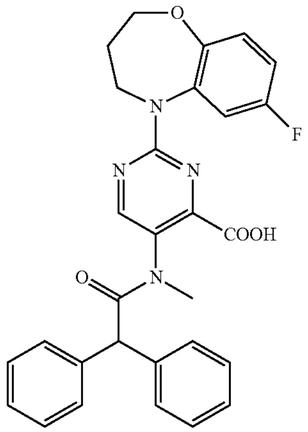
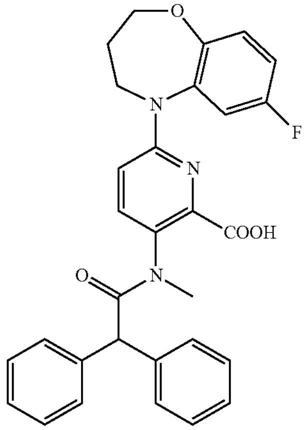
-continued
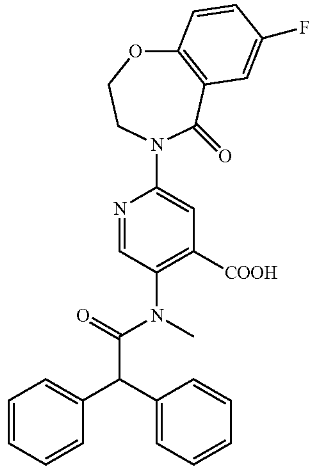
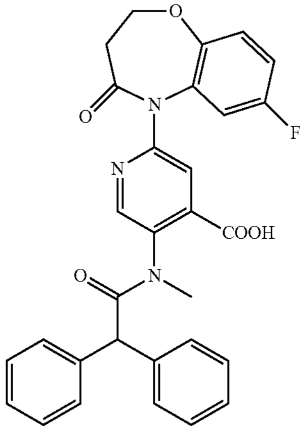
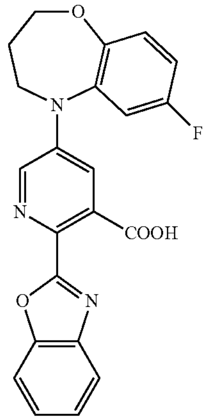
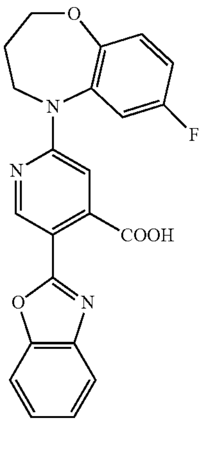
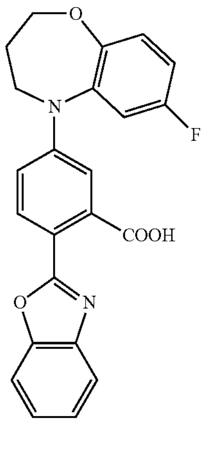

-continued
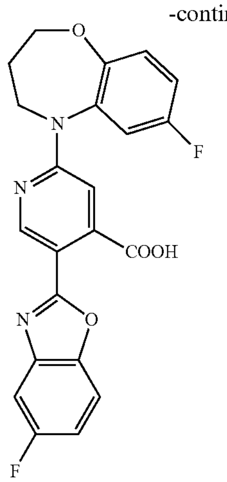
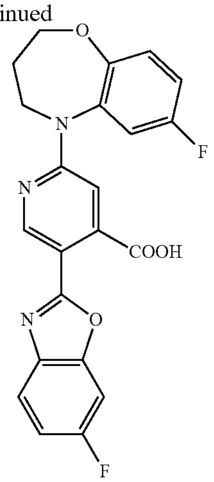
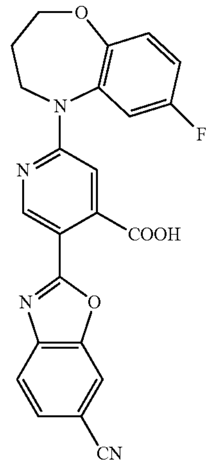
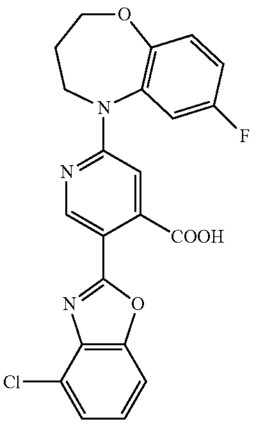
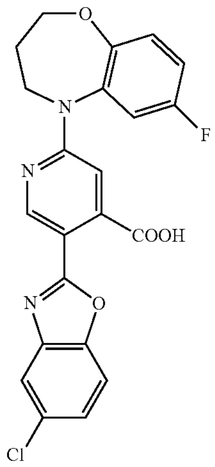
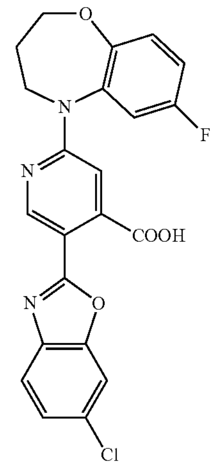
-continued
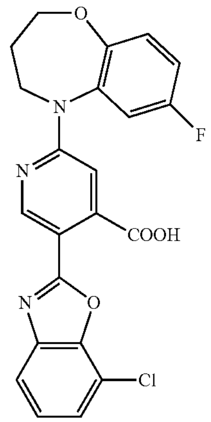
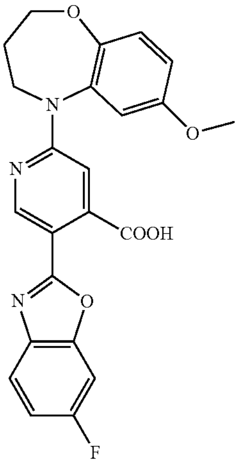
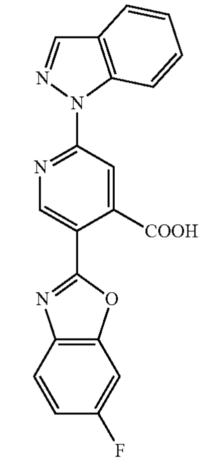
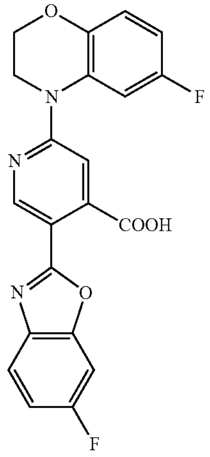
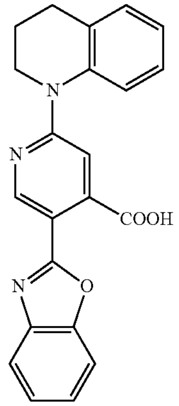
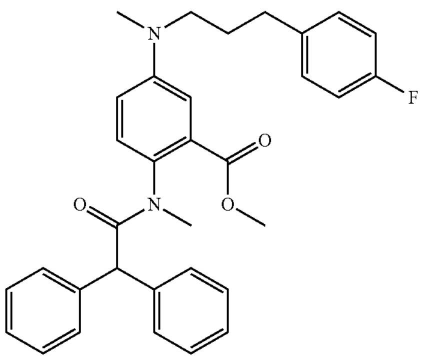

-continued
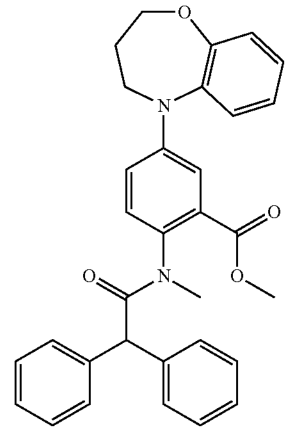
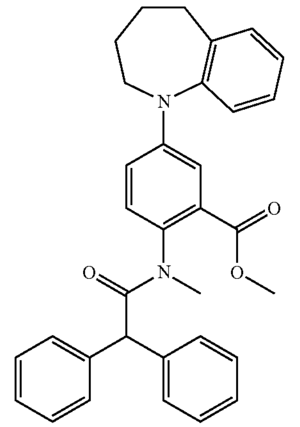
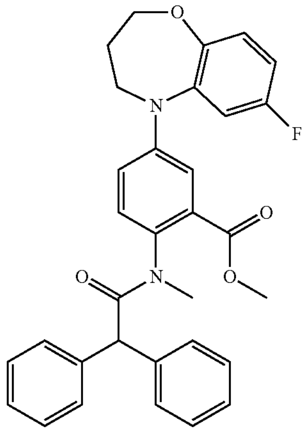
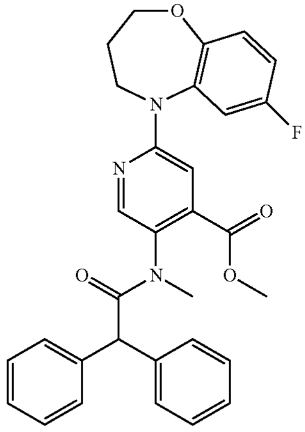
-continued
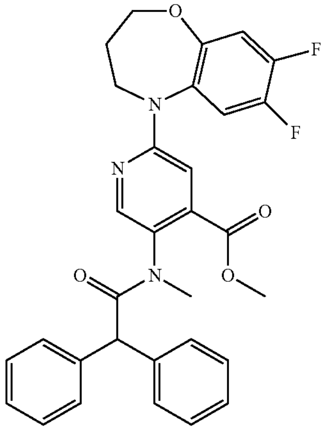
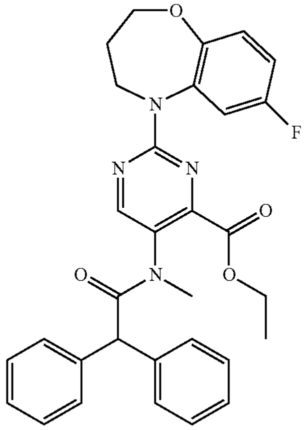
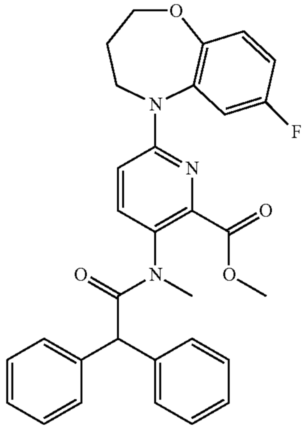

-continued
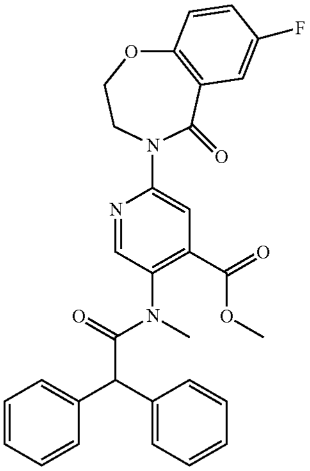
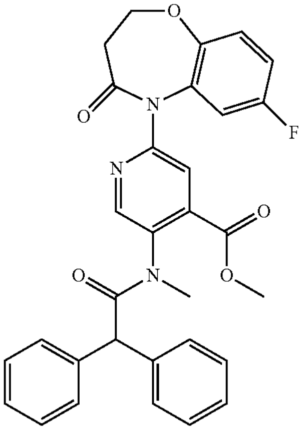
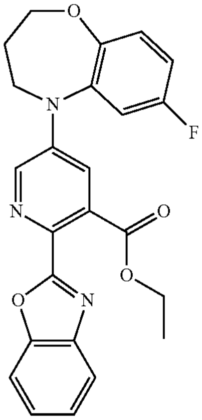
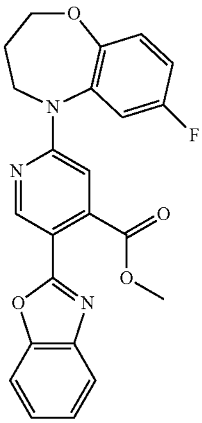
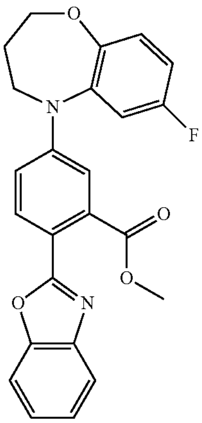
-continued
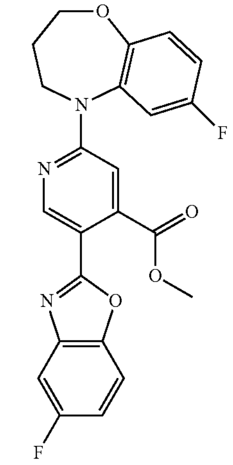
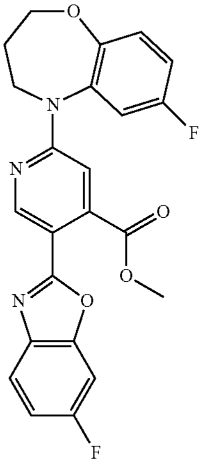
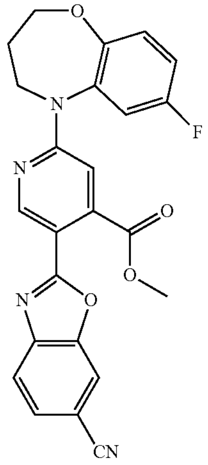
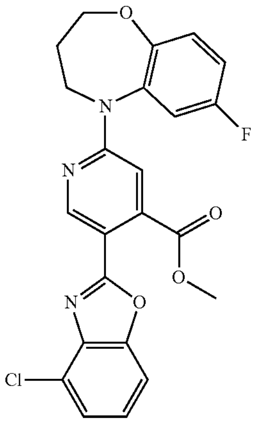
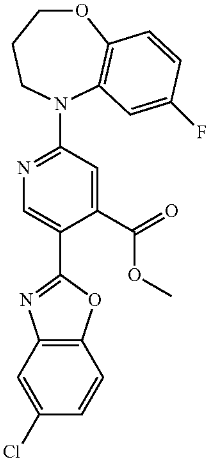
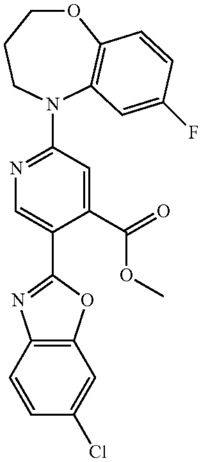

-continued

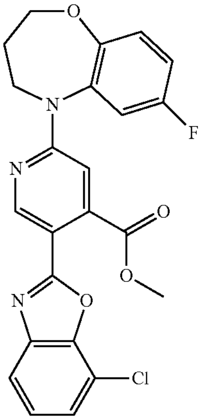

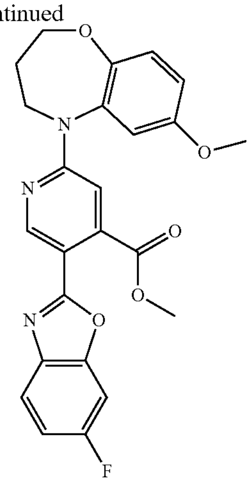

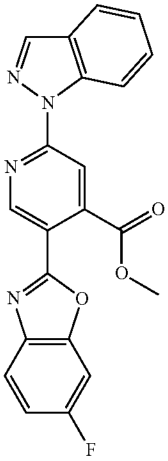

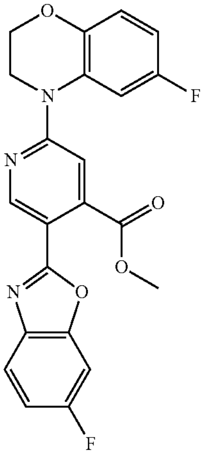

or

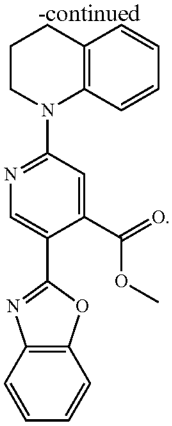

10. A pharmaceutical composition, comprising an effective dose of the compound or the stereoisomer, the tautomer or the pharmaceutically acceptable salt thereof according to claim 1, and a pharmaceutically acceptable carrier, excipient or combinations thereof.

11. The compound or the stereoisomer, the tautomer or the pharmaceutically acceptable salt thereof according to claim 1, wherein $R^e$ is methyl; or L is propylidene.

12. The compound or the stereoisomer, the tautomer or the pharmaceutically acceptable salt thereof according to claim 3, wherein $R^e$ is selected from hydrogen atom and methyl; or L is propylidene; or the aryl for $R^k$ is phenyl.

13. The compound or the stereoisomer, the tautomer or the pharmaceutically acceptable salt thereof according to claim 7, wherein $R^g$ and $R^h$ are each independently a hydrogen atom or fluorine.

* * * * *